US006994969B1

(12) United States Patent
Zabeau et al.

(10) Patent No.: US 6,994,969 B1
(45) Date of Patent: Feb. 7, 2006

(54) DIAGNOSTIC SEQUENCING BY A COMBINATION OF SPECIFIC CLEAVAGE AND MASS SPECTROMETRY

(75) Inventors: Marc Zabeau, Ghent (BE); Patrick Stanssens, Nazareth (BE)

(73) Assignee: Methexis Genomics, N.V., Zwijnaarde (BE)

( * ) Notice: Subject to any disclaimer, the term of this patent is extended or adjusted under 35 U.S.C. 154(b) by 0 days.

(21) Appl. No.: 10/018,453

(22) PCT Filed: Apr. 30, 2000

(86) PCT No.: PCT/EP00/03904

§ 371 (c)(1),
(2), (4) Date: Oct. 30, 2001

(87) PCT Pub. No.: WO00/66771

PCT Pub. Date: Nov. 9, 2000

Related U.S. Application Data

(60) Provisional application No. 60/131,984, filed on Apr. 30, 1999.

(51) Int. Cl.
*C12Q 1/68* (2006.01)
*C12P 19/34* (2006.01)
*C07H 21/02* (2006.01)
*C07H 21/04* (2006.01)
*C07H 21/00* (2006.01)

(52) U.S. Cl. .................. 435/6; 435/91.1; 435/91.2; 435/91.51; 536/23.1; 536/24.3; 536/24.33; 536/25.3

(58) Field of Classification Search .............. 435/6, 435/91.53, 172.3, 320.1, 91.1, 91.2, 91.51, 435/183; 436/173, 94, 174, 518; 935/76, 935/77, 6; 536/24.3, 23.1, 24.33, 25.3
See application file for complete search history.

(56) References Cited

U.S. PATENT DOCUMENTS

| 5,210,412 | A |  | 5/1993  | Levis et al. .............. 250/288 |
| 5,453,247 | A |  | 9/1995  | Beavis et al. ............ 422/68.1 |
| 5,547,835 | A |  | 8/1996  | Köster ...................... 435/6 |
| 5,580,733 | A |  | 12/1996 | Levis et al. ............... 435/6 |
| 5,849,542 | A |  | 12/1998 | Reeve et al. ............ 435/91.1 |
| 5,851,765 | A |  | 12/1998 | Köster ...................... 435/6 |
| 5,869,240 | A |  | 2/1999  | Patterson ................. 435/6 |
| 5,869,242 | A |  | 2/1999  | Kamb ...................... 435/6 |
| 6,107,039 | A | * | 8/2000  | Hanna ..................... 435/6 |
| 6,475,807 | B1 | * | 11/2002 | Geysen et al. ............ 436/518 |

FOREIGN PATENT DOCUMENTS

| EP | 0 103 677 | 3/1984 |
| EP | 0 534 858 | 3/1993 |
| WO | WO 94/21663 | 9/1994 |
| WO | WO 96/29431 | 9/1996 |
| WO | WO 96/36986 | 11/1996 |
| WO | WO 97/33000 | 9/1997 |
| WO | WO 98/03684 | 1/1998 |
| WO | WO 98/12355 | 3/1998 |
| WO | WO 98/20166 | 5/1998 |
| WO | WO 98/40520 | 9/1998 |
| WO | WO 98/45700 | 10/1998 |
| WO | WO 98/54571 | 12/1998 |

OTHER PUBLICATIONS

New England BioLabs Catalog, T4 DNA polymerase, T7 RNA polymerase, pp. 74-75, 1996/1997.*
Aurup et al., *Biochemistry*, 31: 9636-9641 (1992).
Bachem et al., *The Plant Journal*, 9: 745-753 (1996).
Bonnin et al., *J. Mol. Biol.*, 290: 241-251 (1999).
Cannistraro et al., *Eur. J. Biochem.*, 181: 363-370 (1989).
Clayton et al., *Curr. Opin. Microbiol.*, 1: 562-566 (1998).
Conrad et al., *Nucleic Acids Res.*, 23: 1845-1853 (1995).
Contreras et al., *FEBS Lett.*, 16: 281-283 (1971).
Crain et al., *Curr. Opin. in Biotechnol.*, 9: 25-34 (1998).
Eckstein, *Ann. Rev. Biochem.*, 54: 367-402 (1985).
Eng et al., *Nature Biotechnol.*, 15: 422-426 (1997).
Fleischmann et al., *Science*, 269: 496-512 (1995).
Gao et al., *Proc. Natl. Acad. Sci. USA*, 94: 407-411 (1997).
Gish et al., *Nucleic Acids Symp. Ser.*, pp. 253-256 (1987).
Gish et al., *Science*, 240: 1520-1522 (1988).
Hahner et al., *Nucleic Acids Res.*, 25: 1957-1964 (1997).
Hertogs et al., *Animicrob. Agents Chemother.*, 42: 269-276 (1998).

(Continued)

*Primary Examiner*—Kenneth R. Horlick
*Assistant Examiner*—Frank Lu
(74) *Attorney, Agent, or Firm*—Marshall, Gerstein & Borun LLP

(57) ABSTRACT

The present invention is in the field of nucleic acid-based diagnostic assays. More particularly, it relates to methods useful for the "diagnostic sequencing" of regions of sample nucleic acids for which a prototypic or reference sequence is already available (also referred to as "re-sequencing"), or which may be determined using the methods described herein. This diagnostic technology is useful in areas that require such re-sequencing in a rapid and reliable way: (i) the identification of the various allelic sequences of a certain region/gene, (ii) the scoring of disease-associated mutations, (iii) the detection of somatic variations, (iv) studies in the field of molecular evolution, (v) the determination of the nucleic acid sequences of prokaryotic and eukaryotic genomes, (vi) identifying one or more nucleic acids in one or more biological samples', (vii) and determining the expression profile of genes in a biological sample and other areas.

54 Claims, 19 Drawing Sheets

OTHER PUBLICATIONS

Isola et al., *Anal. Chem.*, 71: 2266-2269 (1999).
Ivanova et al., *Nucleic Acids Res.*, 23: 2954-2958 (1995).
Kikuya Kato, *Nucleic Res.*, 23: 3685-3690 (1995).
Köster et al., *Nature Biotechnol.*, 14: 1123-1128 (1996).
Landegren et al., *Genome Res.*, 8: 769-776 (1998).
Lander et al., *Science*, 265: 2037-2048 (1994).
Lee et al.; *Proc. Natl. Acad. Sci. USA*, 92: 8303-8307 (1995).
Liang et al., *Science*, 257: 967-971 (1992).
Limbach, *Mass Spectrom. Rev.*, 15: 297-336 (1996).
Lipshutz et al., *Curr. Opin. in Struct. Biol.*, 4: 376-380 (1994).
Little et al., *J. Am. Chem. Soc.*, 116: 4893-4897 (1994).
Loverix et al., *Nature Struct. Biol.*, 5: 365-368 (1998).
Marotta et al., *Biochemistry*, 12: 2901-2904 (1973).
Maxam et al., *Proc. Natl. Acad. Sci. USA*, 74: 560-564 (1977).
Meador et al., *Eur. J. Biochem.*, 187: 549-553 (1990).
Milligan et al., *Nucleic Acids Res.*, 15: 8783-8798 (1987).
Murray, *J. Mass Spectrom*, 31: 1203-1215 (1996).
Nickerson et al., *Nature Genet.*, 19: 233-240 (1998).
Nordhoff et al., *J. Mass Spectrom.*, 30: 99-112 (1995).
Pieles et al., *Nucleic Acids Res.*, 21: 3191-3196 (1993).
Prashar et al., *Proc. Natl. Acad. Sci. USA*, 93: 659-663 (1996).
Richterich et al., *Nucleic Acids Res.*, 23: 4922-4923 (1995).
Risch et al., *Science*, 273: 1516-1517 (1996).
Sanger et al., *Proc. Natl. Acad. Sci. USA*, 74: 5463-5467 (1977).
Schena et al., *Science*, 270: 467-470 (1995).
Schinazi et al., *Int. Antivir. News*, 4: 95-107 (1996).
Simoncsits et al., *Nature*, 269: 833-836 (1977).
Smith, *Nature Biotechnol.*, 14: 1084-1087 (1996).
Sousa et al., *EMBOL J.* 14: 4609-4621 (1995).
Stevens, *J. Bacteriol.*, 164: 57-62 (1985).
Steyaert, *Eur. J. Biochem.*, 274: 1-11 (1997).
Vos et al., *Nucleic Acids Res.*, 23: 4407-4414 (1995).
Wodicka et al., *Nature Biotechnol.*, 15: 1359-1367 (1997).

* cited by examiner

```
                GTAAAACGAC GGCCAGTGAA TTGTAATACG ACTCACTATA  (SEQ ID NO: 2)
->
GGGCGAATTC GAGCTCGGTA CCCGGGGATC CTCTAGAGTC GACCTGCAGG        100
CATGCAAGCT TGAGTATTCT ATAGTGTCAC CTAAATAGCT TGGCGTAATC      (118)
ATGGTCATAG CTGTTTCCTG TGTGAAATTG TTATCCGCTC ACAATTCCAC        200
ACAACATACG AGCCGGAAGC ATAAAGTGTA AAGCCTGGGG TGCCTAATGA        300
GTGAGCTAAC TCACATTAAT TGCGTTGCGC TCACTGCCCG CTTTCCAGTC
GGGAAACCTG TCGTGCCAGC TGCATTAATG AATCGGCCAA CGCGCGGGGA        400
GAGGCGGTTT GCGTATTGGG CGCTCTTCCG CTTCCTCGCT CACTGACTCG
CTGCGCTCGG TCGTTCGGCT GCGGCGAGCG GTATCAGCTC ACTCAAAGGC        500
GGTAATACGG TTATCCACAG AATCAGGGGA TAACGCAGGA AAGAACATGT
GAGCAAAAGG CCAGCAAAAG GCCAGGAACC GTAAAAAGGC CGCGTTGCTG        600
GCGTTTTTCC ATAGGCTCCG CCCCCCTGAC GAGCATCACA AAAATCGACG
CTCAAGTCAG AGGTGGCGAA ACCCGACAGG ACTATAAAGA TACCAGGCGT        700
TTCCCCCTGG AAGCTCCCTC GTGCGCTCTC CTGTTCCGAC CCTGCCGCTT
ACCGGATACC TGTCCGCCTT TCTCCCTTCG GGAAGCGTGG CGCTTTCTCA        800
TAGCTCACGC TGTAGGTATC TCAGTTCGGT GTAGGTCGTT CGCTCCAAGC
TGGGCTGTGT GCACGAACCC CCCGTTCAGC CCGACCGCTG CGCCTTATCC        900
GGTAACTATC GTCTTGAGTC CAACCCGGTA AGACACGACT TATCGCCACT
GGCAGCAGCC ACTGGTAACA GGATTAGCAG AGCGAGGTAT GTAGGCGGTG
CTACAGAGTT CTTGAAGTGG TGGCCTAACT ACGGCTACAC TAGAAGAACA
GTATTTGGTA TCTGCGCTCT GC (SEQ ID NO: 3)                      (972)
```

FIGURE 5

TAATACGACT CACTATAGGG CGACTTCACG AAGACGGTGA AACTGTTGGA TCCAATTCTT ACCCACACAA

ATACAACAAC TACGAAGGTT TTGATTCTC TGTGAGCTCT CCCTACTACG AATGCCTAT C (SEQ ID NO: 4)

TAATACGACT CACTATAGGG CGAATTCGTA GTAGGGAGAG CTCACAGAGA AATCAAAACC TTCGTAGTTG

TTGTATTTGT GTGGGTAAGA ATTGGATCCA ACAGTTTCAC CGTCTTCGTG AAGTTTATAT CCGG (SEQ ID NO: 5)

FIGURE 7A

| | | |
|---|---|---|
| reference | GGA.TCC.AAT.TCT.TAC.CCA.CAC.AAA.TAC.AAC.AAC.TAC.GAA.GGT.TTT | (SEQ ID NO: 6) |
| mutant #1 | GGA.TCC.AAT.TCT.TTC.CCA.CAC.AAA.TAC.AAC.AAC.TAC.GAA.GGT.TTT | (SEQ ID NO: 7) |
| mutant #2 | GGA.TCC.AAT.TCT.TAC.CCA.CAC.AAA.TAC.AAC.AAG.TAC.GAA.GGT.TTT | (SEQ ID NO: 8) |
| mutant #3 | GGA.TCC.AAT.TCT.TAC.CCA.CAC.AAA.TAC.AAC.AAC.TAC.GAT.GGT.TTT | (SEQ ID NO: 9) |
| mutant #4 | GGA.TCC.AAT.TCT.TAC.CCA.CAC.AAA.TAC.AAC.AAC.TAC.GCA.GGT.TTT | (SEQ ID NO: 10) |
| mutant #5 | GGA.TCC.AAT.TCT.TAC.CCA.CAC.AAA.TAC.AAC.ACG.TAC.GAA.GGT.TTT | (SEQ ID NO: 11) |
| mutant #6 | GGA.TCC.AAT.TCT.TAC.CCA.CAC.GAG.TAC.AAC.AAC.TAC.GAA.GGT.TTT | (SEQ ID NO: 12) |
| mutant #7 | GGA.TCC.GGG.TCT.TAC.CCA.CAC.AAA.TAC.AAC.AAC.TAC.GAA.GGT.TTT | (SEQ ID NO: 13) |
| mutant #8 | GGA.TCC.AAT.TCT.TAC.CCA.CAC.AAA.TAC.AAG.AAT.TTC.GAA.GGT.TTT | (SEQ ID NO: 14) |

FIGURE 7B

SEQUENCE LISTING

<160> NUMBER OF SEQ ID NOS: 30

<210> SEQ ID NO 1
<211> LENGTH: 120
<212> TYPE: DNA
<213> ORGANISM: Homo sapiens
<220> FEATURE:
<223> OTHER INFORMATION: exon 5 of human p53

<400> SEQUENCE: 1
tactcccctg ccctcaacaa gatgttttgc caactggcca agacctgccc tgtgcagctg      60
tgggttgatt ccacaccccc gcccggcacc cgcgtccgcg ccatggccat ctacaagcag     120

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: pGEM3-Zf(+) derived nucleotide

<400> SEQUENCE: 2
gtaaaacgac ggccagtgaa ttgtaatacg actcactata                            40

<210> SEQ ID NO 3
<211> LENGTH: 972
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: pGEM3-Zf(+) derived nucleotide

<400> SEQUENCE: 3
gggcgaattc gagctcggta cccggggatc ctctagagtc gacctgcagg catgcaagct      60
tgagtattct atagtgtcac ctaaatagct tggcgtaatc atggtcatag ctgtttcctg     120
tgtgaaattg ttatccgctc acaattccac acaacatacg agccgaagc ataaagtgta     180 aagcctgggg tgcctaatga gtgagctaac tcacattaat tgcgttgcgc tcactgcccg     240
ctttccagtc gggaaacctg tcgtgccagc tgcattaatg aatcggccaa cgcgcgggga     300
gaggcggttt gcgtattggg cgctcttccg cttcctcgct cactgactcg ctgcgctcgg     360
tcgttcggct gcggcgagcg gtatcagctc actcaaaggc ggtaatacgg ttatccacag     420
aatcagggga taacgcagga aagaacatgt gagcaaaagg ccagcaaaag gccaggaacc     480
gtaaaaaggc cgcgttgctg gcgtttttcc ataggctccg ccccccctgac gagcatcaca     540 aaaatcgacg ctcaagtcag aggtggcgaa acccgacagg actataaaga taccaggcgt     600
ttccccctgg aagctccctc gtgcgctctc ctgttccgac cctgccgctt accggatacc     660
tgtccgcctt tctcccttcg ggaagcgtgg cgctttctca tagctcacgc tgtaggtatc     720
tcagttcggt gtaggtcgtt cgctccaagc tgggctgtgt gcacgaaccc cccgttcagc     780
ccgaccgctg cgccttatcc ggtaactatc gtcttgagtc aacccggta agacacgact     840 tatcgccact ggcagcagcc actggtaaca ggattagcag agcgaggtat gtaggcggtg     900
ctacagagtt cttgaagtgg tggcctaact acggctacac tagaagaaca gtatttggta     960
tctgcgctct gc                                                        972

```
<210> SEQ ID NO 4
<211> LENGTH: 131
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: PCR products and transcripts

<400> SEQUENCE: 4
taatacgact cactataggg cgacttcacg aagacggtga aactgttgga tccaattctt      60
acccacacaa atacaacaac tacgaaggtt ttgatttctc tgtgagctct ccctactacg     120
aatggcctat c                                                         131

<210> SEQ ID NO 5
<211> LENGTH: 134
<212> TYPE: DNA
<213> ORGANISM: Artificial Sequence
<220> FEATURE:
<223> OTHER INFORMATION: PCR products and transcripts
<220> FEATURE:
<223> OTHER INFORMATION: Description of Artificial Sequence: synthetic

<400> SEQUENCE: 5
taatacgact cactataggg cgaattcgta gtagggagag ctcacagaga aatcaaaacc      60
ttcgtagttg ttgtatttgt gtgggtaaga attggatcca acagtttcac cgtcttcgtg    120
aagtttatat ccgg                                                      134

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: reference nucleotide

<400> SEQUENCE: 6
ggatccaatt cttacccaca caaatacaac aactacgaag gtttt                     45

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: mutant 1

<400> SEQUENCE: 7
ggatccaatt ctttcccaca caaatacaac aactacgaag gtttt                     45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: mutant 2

<400> SEQUENCE: 8
ggatccaatt cttacccaca caaatacaac aagtacgaag gtttt                     45

<210> SEQ ID NO 9
```

```
<211> LENGTH: 45
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: mutant 3

<400> SEQUENCE: 9
ggatccaatt cttacccaca caaatacaac aactacgatg gtttt          45

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: mutant 4

<400> SEQUENCE: 10
ggatccaatt cttacccaca caaatacaac aactacgtag gtttt          45

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: mutant 5

<400> SEQUENCE: 11
ggatccaatt cttacccaca caaatacaac acgtacgaag gtttt          45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: mutant 6

<400> SEQUENCE: 12
ggatccaatt cttacccaca ccagtacaac aactacgaag gtttt          45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: mutant 7

<400> SEQUENCE: 13
ggatccgcgt cttacccaca caaatacaac aactacgaag gtttt          45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: mutant 8

<400> SEQUENCE: 14
```

```
ggatccaatt cttacccaca caaatacaag aatttcgaag gtttt            45

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 15
ctagcccccg atc                                               13

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 16
ccggatataa acttcacgaa gacgg                                  25

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 17
gataggccat tcgtagtagg gagagc                                 26

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 18
taatacgact cactataggg cgacttcacg aagacgg                     37

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 19
taatacgact cactataggg cgaattcgta gtagggagag c                41

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: synthetic
<220> FEATURE:
<223> OTHER INFORMATION: reference fragment

<400> SEQUENCE: 20
gtagttgttg tatttgtgtg ggtaagaatt ggatc                       35

<210> SEQ ID NO 21
```

```
<211> LENGTH: 15
<212> TYPE: RNA
<213> ORGANISM: Artificial Sequence
<220> FEATURE:
<223> OTHER INFORMATION: Description of Artificial Sequence: synthetic
<220> FEATURE:
<223> OTHER INFORMATION: polymorphic 15-mer fragment

<400> SEQUENCE: 21
aaaucaaaac cuucg                                                      15

<210> SEQ ID NO 22
<211> LENGTH: 10
<212> TYPE: DNA
<213> ORGANISM: Artificial Sequence
<220> FEATURE:
<223> OTHER INFORMATION: RNAse-A digestion products
<220> FEATURE:
<223> OTHER INFORMATION: Description of Artificial Sequence: synthetic

<400> SEQUENCE: 22
ttgagtattc                                                            10

<210> SEQ ID NO 23
<211> LENGTH: 10
<212> TYPE: DNA
<213> ORGANISM: Artificial Sequence
<220> FEATURE:
<223> OTHER INFORMATION: RNAse-A digestion products
<220> FEATURE:
<223> OTHER INFORMATION: Description of Artificial Sequence: synthetic

<400> SEQUENCE: 23
acccggggat                                                            10

<210> SEQ ID NO 24
<211> LENGTH: 15
<212> TYPE: DNA
<213> ORGANISM: Artificial Sequence
<220> FEATURE:
<223> OTHER INFORMATION: RNAse-A digestion products
<220> FEATURE:
<223> OTHER INFORMATION: Description of Artificial Sequence: synthetic

<400> SEQUENCE: 24
gaaggttttg atttc                                                      15

<210> SEQ ID NO 25
<211> LENGTH: 12
<212> TYPE: DNA
<213> ORGANISM: Artificial Sequence
<220> FEATURE:
<223> OTHER INFORMATION: RNAse-A digestion products
<220> FEATURE:
<223> OTHER INFORMATION: Description of Artificial Sequence: synthetic

<400> SEQUENCE: 25
acccacacaa at                                                         12

<210> SEQ ID NO 26
<211> LENGTH: 12
<212> TYPE: DNA
<213> ORGANISM: Artificial Sequence
<220> FEATURE:
<223> OTHER INFORMATION: RNAse-A digestion products
<220> FEATURE:
<223> OTHER INFORMATION: Description of Artificial Sequence: synthetic

<400> SEQUENCE: 26
```

```
cacgaagacg gt                                                            12

<210> SEQ ID NO 27
<211> LENGTH: 14
<212> TYPE: DNA
<213> ORGANISM: Artificial Sequence
<220> FEATURE:
<223> OTHER INFORMATION: RNAse-A digestion products
<220> FEATURE:
<223> OTHER INFORMATION: Description of Artificial Sequence: synthetic

<400> SEQUENCE: 27
gtgaagttta tatc                                                          14

<210> SEQ ID NO 28
<211> LENGTH: 14
<212> TYPE: DNA
<213> ORGANISM: Artificial Sequence
<220> FEATURE:
<223> OTHER INFORMATION: RNAse-A digestion products
<220> FEATURE:
<223> OTHER INFORMATION: Description of Artificial Sequence: synthetic

<400> SEQUENCE: 28
gtagtaggga gagc                                                          14

<210> SEQ ID NO 29
<211> LENGTH: 10
<212> TYPE: DNA
<213> ORGANISM: Artificial Sequence
<220> FEATURE:
<223> OTHER INFORMATION: RNAse-A digestion products
<220> FEATURE:
<223> OTHER INFORMATION: Description of Artificial Sequence: synthetic

<400> SEQUENCE: 29
agggagagct                                                               10

<210> SEQ ID NO 30
<211> LENGTH: 11
<212> TYPE: DNA
<213> ORGANISM: Artificial Sequence
<220> FEATURE:
<223> OTHER INFORMATION: RNAse-A digestion products
<220> FEATURE:
<223> OTHER INFORMATION: Description of Artificial Sequence: synthetic

<400> SEQUENCE: 30
cacagagaaa t                                                             11
```

DIAGNOSTIC SEQUENCING BY A COMBINATION OF SPECIFIC CLEAVAGE AND MASS SPECTROMETRY

This application claims the benefit Provisional Application No. 60/131,984, filed Apr. 30, 1999.

FIELD OF INVENTION

The present invention is in the field of nucleic acid-based diagnostic assays. More particularly, it relates to methods useful for the "diagnostic sequencing" of regions of sample nucleic acids for which a prototypic or reference sequence is already available (also referred to as 're-sequencing'), or which may be determined using the methods described herein. This diagnostic technology is useful in areas that require such re-sequencing in a rapid and reliable way: (i) the identification of the various allelic sequences of a certain region/gene, (ii) the scoring of disease-associated mutations, (iii) the detection of somatic variations, (iv) studies in the field of molecular evolution, (v) the determination of the nucleic acid sequences of prokaryotic and eukaryotic genomes; (vi) identifying one or more nucleic acids in one or more biological samples; (vii) and determining the expression profile of genes in a biological sample and other areas.

BACKGROUND OF INVENTION

Complete reference genome sequences for a number of model organisms as well as humans are currently available or are expected to become available in the near future. A parallel challenge is to characterize the type and extent of variation in the sequences of interest because it underlies the heritable differences among individuals and populations. In humans, the vast majority of sequence variation consists of nucleotide substitutions referred to as single nucleotide polymorphisms (SNPs). DNA sequencing is the most sensitive method to discover polymorphisms [Eng C. and Vijg J. et al., *Nature Biotechnol.* 15: 422–426 (1997)]. A growing panel of such sequence variants, together with powerful methods to monitor them [Landegren U. et al., *Genome Res.* 8: 769–776 (1998)], is useful in linkage studies to identify even the most subtle disease susceptibility loci [Lander E. and Schork N., *Science* 265: 2037–2048 (1994); Risch N. and Merikangas K., *Science* 273: 1516–1517 (1996)]. Also, the identification of all (functional) allelic variants will require the re-sequencing of particular regions in a large number of samples [Nickerson D. et al., *Nature Genet.* 19: 233–240 (1998)]. Although a number of methods to monitor known SNPs have been developed [Landegren U. et al., *Genome Res.* 8: 769–776 (1998)], re-sequencing is likely to be routinely applied to secure diagnoses of patients. Indeed, in a significant number of disease-associated genes that have been surveyed thus far, literally hundreds or even thousands of different mutations have been identified and catalogued. Consequently, sequence determination represents the ultimate level of resolution and may be the preferred method to monitor which mutation or combination of mutations, out of a large number of mutations of known clinical relevance, is present.

It would appear that the field of biomedical genetics will rely heavily on sequencing technology. Hence, there is a need for advanced sequencing methods that are time- and cost-competitive, and at the same time accurate and robust. Recent developments in this area include improvements to the basic dideoxy chain termination sequencing method [Sanger et al. *Proc. Natl. Acad. Sci. USA* 74: 5463–5467 (1977); reviewed by Lipshutz R. and Fodor S. et al., *Current Opinion in Structural Biology* 4: 376–380 (1994)], as well as new approaches that are based on entirely new paradigms. Two such novel approaches are sequencing-by-hybridization (SBH) [Drmanac R. et al., *Science* 260: 1649–1652 (1993)] and pyro-sequencing [Ronaghi M. et al., *Science* 281: 363–365 (1998); Ronaghi M. et al., *Anal. Biochem.* 242: 84–89 (1996)]. While the concepts of these approaches have been experimentally validated, their ultimate acceptance and usage may depend on the type of application —e.g. de novo sequencing, re-sequencing, and genotyping of known SNPs.

Recently, progress has also been made in the use of mass spectroscopy (MS) to analyze nucleic acids [Crain, P. F. and McCloskey, J. A., *Current Opinion in Biotechnology* 9: 25–34 (1998), and references cited therein]. One promising development has been the application of MS to the sequence determination of DNA and RNA oligonucleotides [Limbach P., *Mass Spectrom. Rev.* 15: 297–336 (1996); Murray K., *J. Mass Spectrom.* 31: 1203–1215 (1996)]. MS and more particularly, matrix-assisted laser desorption/ionization MS (MALDI MS) has the potential of very high throughput due to high-speed signal acquisition and automated analysis off solid surfaces. It has been pointed out that MS, in addition to saving time, measures an intrinsic property of the molecules, and therefore yields a significantly more informative signal [Koster H. et al., *Nature Biotechnol.*, 14: 1123–1128 (1996)].

Sequence information can be derived directly from gas-phase fragmentation [see for example Nordhoff E. et al., *J. Mass Spectrom.*, 30:99–112 (1995); Little D. et al., *J. A. Chem. Soc.*, 116: 4893–4897 (1994); Wang B. et al., WO 98/03684 and WO 98/40520; Blocker H. et al., EP 0 103 677; Foote S. et al., WO 98/54571]. In contrast, indirect methods measure the mass of fragments obtained by a variety of methods in the solution phase, i.e., prior to the generation of gas phase ions. In its simplest form, mass analysis replaces the gel-electrophoretic fractionation of the fragment-ladder (i.e., a nested set of fragments that share one common endpoint) generated by the sequencing reactions. The sequencing reactions need not necessarily be base-specific because the base-calling may also be based on accurate mass measurement of fragments that terminate at successive positions and that differ from one another by one nucleotide residue. The fragment-ladder can be generated by the Sanger method [Köster H. et al., *Nature Biotechnol.*, 14: 1123–1128 (1996); Reeve M. A., Howe R. P., Schwarz T., U.S. Pat. No. 5,849,542; Köster H., U.S. Pat. No. 5,547,835; Levis R. and Romano L., U.S. Pat. No. 5,210,412 and U.S. Pat. No. 5,580,733; Chait B. and Beavis R., U.S. Pat. No. 5,453,247], by base-specific partial RNA digestion [Hahner S. et al., *Nucleic Acids Res.*, 25: 1957–1964 (1997); Köster H., WO 98/20166] or by chemical cleavage [Isola N. et al., *Anal. Chem.*, 71: 2266–2269 (1999); references cited in Limbach P., *Mass Spectrom. Rev.*, 15: 297–336 (1996)]. An alternative method consists of analyzing the ladder generated by exonuclease digestion from either the 3'- or 5'-end [Pieles U. et al., *Nucleic Acids Res.*, 21: 3191–3196 (1993); Köster H., U.S. Pat. No. 5,851,765; Engels J. et al., WO 98/45700; Tarr G. and Patterson D., WO 96/36986; Patterson D., U.S. Pat. No. 5,869,240].

A severe limitation of both the direct and indirect MS methodologies under the current performance conditions is the poor applicability to chain lengths beyond ~30–50 nucleotides. As a consequence, it has been suggested that the prospects for MS lie with DNA diagnostic assays, rather than large-scale sequencing [Smith L., *Nature Biotechnol.*, 14: 1084–1087 (1996)]. Given the fact that MS represents an exquisite means to analyze short nucleotide fragments, the various MS-based processes that have been described for nucleic acid based diagnostic purposes generally involve the derivation and analysis of such relatively short fragments [see for example Koster H., WO 96/29431; Koster H. et al., WO 98/20166; Shaler T. et al., WO 98/12355; Kamb A., U.S. Pat. No. 5,869,242; Monforte J. et al., WO 97/33000; Foote S. et al., WO 98/54571].

Some of the MS-based assays have been used for the scoring of defined mutations or polymorphisms. Other processes derive multiple oligonucleotide fragments and yield a 'mass-fingerprint' so as to analyze a larger target nucleic acid region for mutations and/or polymorphisms. The latter MS analyses are however considerably less informative in that they are essentially restricted to the detection of sequence variations. The methods cannot be applied to diagnostic sequencing of nucleic acids, where the term diagnostic sequencing means the unequivocal determination of the presence, the nature and the position of sequence variations. At best, the measurements confirm the base composition of small fragments whose masses are determined with sufficient accuracy to reduce the number of possible compositional isomers. Also, it will be realized that only certain changes in composition (as revealed by shifts in the mass spectrum) can be unambiguously assigned to a polymorphism or mutation. A match between the spectrum of the interrogated sequence and a reference-spectrum obtained from wild-type sequence or sequences known to contain a given polymorphism, is assumed to indicate that the interrogated nucleic acid region is wild-type or incorporates the previously known polymorphisms, thereby disregarding certain other possible interpretations.

While most methods in the art do yield sequence-related information, they do not disclose that a combination of several different mass spectra, obtained after complementary digestion reactions, allows for the effective survey of a nucleic acid region and provides an unambiguous assignment of both known as well as previously unknown sequence variations that occur relative to a reference nucleic acid with a known nucleotide sequence.

In view of the limitations of the methods described above, the art would clearly benefit from a new procedure for the diagnostic sequencing of nucleic acids that would overcome the shortcomings of the processes discussed above.

In comparison with conventional sequencing technology, i.e., the gel-electrophoretic analysis of fragment ladders, the methods of the present invention are more suited for the simultaneous analysis of multiple target sequences. In general, each particular sequence or sequence variant is associated with a distinct set of mass peaks. Consequently, the sequencing reactions according to the methods of the present invention lend themselves readily to (i) multiplexing (i.e., the analysis of two or more target non-contiguous target regions from a single biological sample), (ii) the analysis of heterozygous samples, as well as (iii) pooling strategies (i.e., the simultaneous sequencing of the analogous regions derived from two or more different biological samples).

Because of the multiplex capacity, the present methods can be adapted as a tool for the genome-wide discovery and scoring of polymorphisms (e.g., SNPs) useful as markers in genetic linkage studies. The unambiguous identification/diagnosing of a number of variant positions is less demanding than full sequencing and, consequently, a considerable number of target genomic loci can be combined and analyzed at the same time, especially when their lengths are kept relatively small. The number of markers that can be scored in parallel will depend on the level of genetic diversity in the species of interest and on the precise method used to prepare and analyze the target nucleic acids, but may typically be in the order of a few tens to up to 100 with current MS capabilities. The addition of multiplexing to the high-precision and high-speed characteristics of MS constitutes a new marker technology that enables the large-scale and cost-effective scoring of several (tens of) thousands of markers. Some aspects of the application of the present methods to genome-wide genotyping are described in Example 5.

Sequencing reactions according to the methods of the present invention yield, in principle, a discrete set of fragments for each individual sequence or sequence variant whereas conventional sequence ladders stack on top of one another. Therefore, such sequences or sequence variants can be analyzed even when present as a lesser species. This is a useful quality for the analysis of clinical samples which are often genetically heterogeneous because of the presence of both normal and diseased cells or in itself (e.g., cancerous tissue, viral quasi-species). Additionally, the ability to detect mutations at a low ratio of mutant over wild-type allele makes it practicable to pool individual biological samples, a strategy which should permit a more cost-effective search for genomic sequence variations in a population.

The present invention rests in part on the insight that integration of the data obtained in a set of complementary fingerprints produced by an appropriate set of complementary cleavage reactions of the invention represents a level of characterization of a sample nucleic acid essentially equal to sequence determination. The present invention is also directed to the use of cleavage protocols that result in the generation of cleavage products that range from mono- and dinucleotides to fragments of a few tens of nucleotides that are particularly suited for analysis by MS. At the same time, the present method is distinct from the other fragmentation processes that are limited to screening target nucleic acids for a wide range of potential mutations. According to the present invention, a combination of several different mass spectra, obtained after complementary digestion reactions, coupled with systematic computational analysis allows the survey of a selected target nucleic acid or region thereof and leads to the unambiguous assignment of both known and previously unknown sequence variations. In certain aspects of the present invention, knowledge of the reference sequence in combination with the methods disclosed herein allows modeling of the experimental approach, anticipation of potential ambiguities, and the design of an adequate resolution.

SUMMARY OF INVENTION

The present invention is directed to a mass spectroscopic method for detecting or analyzing a particular nucleic acid sequence. The present invention is useful for de novo sequencing or re-sequencing nucleic acid in a rapid and reliable way which permits, for example, the identification of the various allelic sequences of a certain region/gene, the identification and scoring of disease-associated mutations, the detection of somatic variations, determining genetic diversity in molecular evolution, and the determination of the genomic sequences e.g., of viral and bacterial isolates. The present invention is also useful for identification of all nucleic acid molecules in one or more biological samples including for expression profiling i.e., identification of all the mRNA species that are expressed in a given cell at a given time, by rapidly determining the sequence of the mRNA that is expressed.

In one embodiment, the present invention is directed to methods for sequence analysis of one or more target nucleic acids for which a known reference nucleic acid sequence is available. In this method, one or more target nucleic acids are derived from one or more biological samples, and a reference nucleic acid are each subjected to complementary cleavage reactions, and the products of the cleavage reactions are analyzed by mass spectroscopic methods. The mass spectra of the one or more target nucleic acids are then compared with the mass spectra of the reference nucleic acid sequence, and the nucleotide sequence of the one or more target nucleic acids is deduced by systematic computational analysis.

In one aspect of this embodiment, multiple targets, such as cDNA clones, are prepared from the mRNA of the same biological sample, and are separately analyzed as above in parallel experiments. In a second aspect, multiple targets are derived from the same biological sample and are analyzed simultaneously, for example in genome-wide genotyping.

The one or more target nucleic acids may be selected from the group consisting of a single stranded DNA, a double stranded DNA, a cDNA, a single stranded RNA, a double stranded RNA, a DNA/RNA hybrid, and a DNA/RNA mosaic nucleic acid.

In a second embodiment, the one or more target nucleic acids are selected from the group consisting of an amplified nucleic acid fragment, a cloned nucleic acid fragment, and a series of non-contiguous DNA fragments from the genome. In one aspect of this invention, the amplified one or more target nucleic acids are derived by one or more consecutive amplification procedures selected from the group consisting of in vivo cloning, the polymerase chain reaction (PCR), reverse transcription followed by the polymerase chain reaction (RT-PCR), strand displacement amplification (SDA), and transcription based processes.

In a preferred embodiment, the amplified nucleic acid fragments are RNA transcripts generated from one or more target nucleic acids or a reference nucleic acid by a process comprising the steps of: (a) amplifying the one or more target nucleic acids or the reference nucleic acid using one or more primers corresponding to a region that is complementary to the one or more target nucleic acids or the reference nucleic acid and encoding an expression control sequence using any one of the amplification procedures described above, and (b) generating RNA transcripts from the amplified one or more target nucleic acids or reference nucleic acid using one or more RNA polymerases that recognize the transcription control sequence on the target or reference nucleic acid. The RNA generated by the above process is then subjected to complementary cleavage reactions to generate nucleic acid fragments, which are then analyzed by MS. The transcription control sequence may be selected from the group consisting of an eukaryotic transcription control sequence, a prokaryotic transcription control sequence, and a viral transcription control sequence. The prokaryotic transcription control sequence may be selected from the group consisting of T3, T7, and SP6 promoters. The cognate RNA polymerases may be either a wild-type or a mutant form capable of incorporating non-canonical substrates with a 2'-substituent other than a hydroxyl group.

In a third embodiment, the one or more target nucleic acids are amplified using modified nucleoside triphosphates. The mass modified nucleoside triphosphates may be selected from the group consisting of a mass modified deoxynucleoside triphosphate, a mass modified dideoxynucleoside triphosphate, and a mass modified ribonucleoside triphosphate. The mass modified nucleoside triphosphate may be modified on the base, the sugar, and/or the phosphate moiety, and are introduced through an enzymatic step, chemically, or a combination of both. In one aspect the modification may consist of 2'-substituents other than a hydroxyl group on transcript subunits. In another aspect, the modification may consist of phosphorothioate internucleoside linkages or phosphorothioate internucleoside linkages further reacted with an alkylating reagent. In yet another aspect, the modification may consist of a methyl group on C5 of the uridine-5'-monophosphate subunits. Such modifications may alter the specificity of cleavage by certain reagents, and/or the mass of the cleavage products, and/or the length of the cleavage products.

In one aspect of the invention, the one or more target nucleic acids and reference nucleic acid are subjected to complementary cleavage reactions using enzymatic cleavage, chemical cleavage, and/or physical cleavage reactions. In a preferred embodiment, the one or more target nucleic acids and the reference nucleic acid are subjected to enzymatic cleavage reaction using one or more enzymes selected from the group consisting of endonucleases and exonucleases. In a more preferred embodiment, the target nucleic acid is a double-stranded RNA and the endonuclease used is a ribonuclease. The ribonuclease may be selected the G-specific T. ribonuclease, the A-specific $U_2$ ribonuclease, the A/U specific phyM ribonuclease, the U/C specific ribonuclease A, the C-specific chicken liver ribonuclease (RNaseCL3), and cusativin. In one aspect of this preferred embodiment, the target nucleic acid is a phosphorothioate-modified single-stranded DNA or RNA and the endonuclease is nuclease P1.

In another aspect, the mass spectroscopical analysis of the nucleic acid fragments is performed using a mass spectrometer selected from the group consisting of Matrix-Assisted Laser Desorption/Ionization-Time-of-flight (MALDI-TOF), Electrospray-Ionization (ESI), and Fourier Transform-Ion Cyclotron Resonance (FT-ICR). In a preferred embodiment the mass spectrometer used for the analysis of the cleavage fragments is MALDI-TOF.

In a fifth embodiment, the method of the present invention can be used for diagnosing nucleic acid sequence variations in one or more target nucleic acids derived from a biological sample, for which a known reference nucleic acid sequence is available. In this method, one or more target nucleic acids derived from a biological sample, and a reference nucleic acid whose sequence has been predetermined are subjected to complementary cleavage reactions, and the products of the cleavage reactions are analyzed by mass spectroscopic methods. The mass spectra of the one or more target nucleic acids is then compared with the mass spectra of the reference nucleic acid, and the nucleotide sequence variations in the one or more target nucleic acids is then deduced by systematic computational analysis of the sequence variations between the one or more target nucleic acids and the reference nucleic acid. A variety of acid sequence variations including deletions, substitutions and/or insertions in a target nucleic acid can be determined using the method of the present invention.

In a sixth embodiment, the method of the present invention can be used for scoring known nucleotide sequence variations in one or more target nucleic acids derived from a biological sample, for which a known reference nucleic acid sequence is available. In this embodiment, one or more target nucleic acids derived from a biological sample, and a reference nucleic acid are subjected to complementary cleavage reactions, and the products of the cleavage reactions are analyzed by mass spectroscopic methods. The mass spectra of the one or more target nucleic acid is then compared with the mass spectra of the reference nucleic acid sequence, and the nucleotide sequence variations/mutations in the one or more target nucleic acids are scored by comparing the nucleic sequence between the one or more target nucleic acid and reference nucleic acid by systematic computational analysis.

In a seventh embodiment, the method of the present invention can be used for determining the nucleotide sequence (de novo sequencing) of one or more target nucleic acids derived from a biological sample for which no reference sequence is available. In this method, target nucleic acid, derived from a biological sample is subjected to complementary cleavage reactions, and the products of the cleavage reactions are analyzed by mass spectroscopic methods. The mass spectra of the one or more target nucleic acids coupled with a systematic computational analysis is then used to deduce the sequence of the one or more target nucleic acids.

In an eighth embodiment, the method of the present invention can be used for genome-wide genotyping of one or more known or unknown target nucleic acids. In this method, one or more target nucleic acids, derived from a biological sample, are amplified and then subjected to complementary cleavage reactions. In one aspect, multiple targets are derived from a single sample and are analyzed simultaneously. The products of the cleavage reactions are then analyzed by mass spectroscopic methods. The mass spectra of the one or more known or unknown target nucleic acid is compared with the mass spectra of a reference nucleic acid. This comparison is then used to infer the genotype of an organism from which the biological sample is derived and to determine therefrom the genetically relevant nucleic acid sequence variations of the one or more known or unknown nucleic acids.

In a ninth embodiment, the method of the present invention can be used to identify one or more target nucleic acids in one or more biological samples. In this method, one or more target nucleic acids, derived from a biological sample, are amplified and then subjected to complementary cleavage reactions. In one aspect, multiple targets are derived from a single sample and are analyzed simultaneously. The products of the cleavage reactions are then analyzed by mass spectroscopic methods. The identity of one or more target nucleic acids is deduced by comparing the mass spectra of the one or more known or unknown target nucleic acid with each other or by comparison with a plurality of mass spectra of reference nucleic acids.

In one aspect, the method of the present invention can be used for expression profiling, i.e. identifying the various mRNA expressed in one or more biological samples.

Also encompassed by the present invention is a kit for sequence analysis of one or more target nucleic acids using mass spectroscopy, the kit comprising a container having one or more sets of reference nucleic acids for which the nucleotide sequence is known, one or more nucleic acid cleaving agents, and computer algorithm/software for comparing the mass spectra of the one or more target nucleic acids with the mass spectra of the reference nucleic acid and deducing therefrom the nucleic acid sequence of the one or more target nucleic acids. In one embodiment, the nucleic acid cleaving agent in the kit is a chemical agent. In an alternate embodiment, the nucleic acid cleaving agent is an enzyme selected from a group of enzymes consisting of endonucleases and exonucleases. In a preferred embodiment, the endonuclease is a ribonuclease selected from the group consisting of the G-specific T. ribonuclease, the A-specific $U_2$ ribonuclease, the A/U specific phyM ribonuclease, the U/C specific ribonuclease A, the C-specific chicken liver ribonuclease (RNaseCL3), and cusativin.

DESCRIPTION OF DRAWINGS

FIG. 5 (SEQ ID NO: 2 and SEQ ID NO: 3) is a graphic representation of the pGEM3-Zf(+) derived nucleotide sequences used as a model in Examples 2 and 4. The regions corresponding to the PCR primers are underlined. Two PCR products (158 and 1012 base-pairs long) were generated. Both amplification products encompass the phage T7 promoter site; the transcription initiation site is indicated with an arrow. The numbering refers to the respective transcripts (118 and 972 nucleotides).

FIG. 7A (SEQ ID NO: 4 and SEQ ID NO: 5) is a graphical representation of PCR products and transcripts used for diagnostic sequencing of the RNase-T1 coding region. Two parallel amplification reactions were performed with either the upstream or downstream primer tagged to the T7 promoter. The amplification products allow the transcription of the (+; upper sequence) or (−; lower sequence) strand. The underlined region shows the appended T7 promoter site. An arrow indicates the transcription initiation site.

FIG. 7B (SEQ ID NO: 6 through SEQ ID NO: 14) shows the position and nature of a number of single, double, and triple mutations in RNase-T1 (reference denotes the wild-type coding region).

DETAILED DESCRIPTION OF INVENTION

Figure 1A:
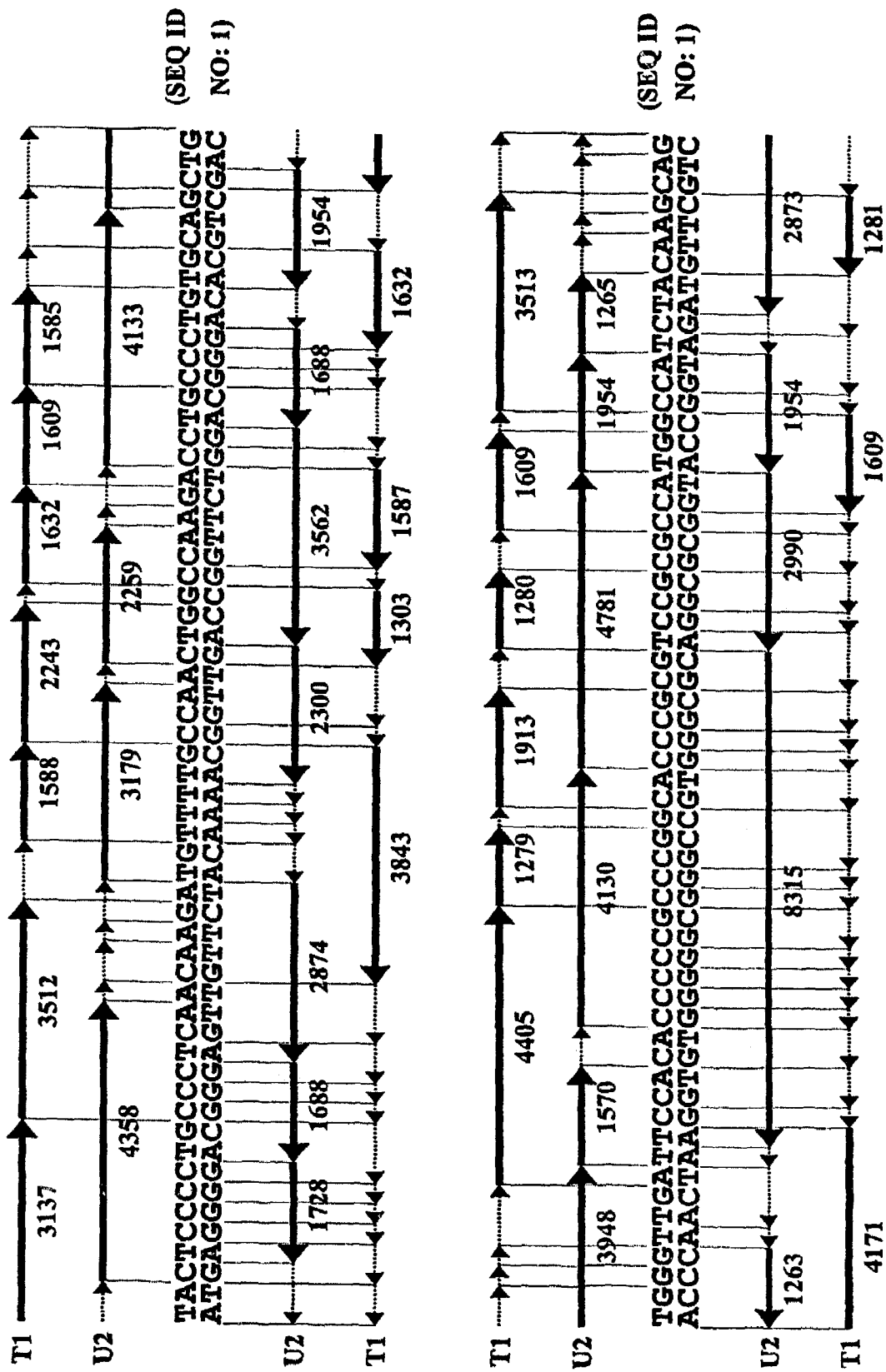
FIG. 1A (SEQ ID NO: 1) graphically represents the first 120 nucleotides of exon 5 of human p53 as well as the fragments that would result from cleavage of the (+) and (−) strand transcript after G (RNase-T1) or A (RNase-U2). The dotted and full arrows correspond to the resulting $\leq$3-mer and $\geq$4-mer cleavage products. The arrows from left to right represent fragments from the (+) strand, while the arrows from right to left represent fragments from the (−) strand. The numbers indicate the neutral molecular masses of the $\geq$4-mer ribonucleotide fragments. The calculation assumes that all fragments contain 5'-hydroxyl and 3'-phosphate groups.

With current capabilities in mass spectroscopy, it is impractical to sequence nucleic acids greater than ~50 bases in length. Consequently, an impractical and cumbersome number of independent sequencing reactions is necessary to cover the thousands of bases of a gene or other genetic region of interest. The methods of the present invention described below overcome this limitation. At the same time, the present method is distinct from the other fragmentation processes that are limited to screening target nucleic acids for a wide range of potential mutations. Indeed, the appropriate choice of complementary cleavage reactions as described herein allows the determination of the exact location and nature of a genetic variation. Also, it is demonstrated herein that computational protocols are an integral part of the described method. The methods and algorithms are required to deduce, on the basis of the reference sequence(s), the relation between (i) the spectral changes associated with one or more cleavage reactions of a given nature, and (ii) the uniquely defined sequence variations.

Sequencing reactions according to the methods of the present invention can be multiplexed, i.e. used for the simultaneous analysis of multiple non-contiguous target regions [supra]. Therefore, the methods can be adapted as a tool for the genome-wide discovery and/or scoring of polymorphisms (e.g. SNPs) useful as markers in genetic linkage studies. Indeed, it will be recognized that the unambiguous identification/diagnosing of a number of variant positions is less demanding than full sequencing and that consequently a considerable number of target genomic loci can be combined and analyzed in parallel, especially when their lengths are kept relatively small. The number of markers that can be scored in parallel will depend on the level of genetic diversity in the species of interest and on the precise method used to prepare and analyze the target nucleic acids, but may typically be in the order of a few tens to up to 100 or more with current MS capabilities. The addition of multiplexing to the high-precision and high-speed characteristics of MS constitutes a new marker technology that enables the large-scale and cost-effective scoring of several (tens of) thousands of markers. Some aspects of the application of the present methods to genome-wide genotyping are described in Example 5.

The present invention provides a mass spectroscopy (MS) based nucleic acid sequencing method that overcomes some of the drawbacks inherent in the prior art. In contrast to the previously described methods, the methods of the present invention do not require the generation of a ladder, i.e. an ordered set of nested nucleic acid fragments characterized by a common end. Rather, the disclosed methods rely on a combination of complementary fragmentation reactions and the analytical resolution power of MS to improve mass resolution and mass accuracy. The present invention is directed to the use of enzymatic cleavage protocols that result in the generation of cleavage products that range from mono- and dinucleotides to fragments of a few tens of nucleotides. that are particularly suited for analysis by MS. According to the present invention, a combination of several different mass spectra, obtained after complementary digestion reactions, coupled with systematic computational analysis allows the survey of a selected nucleic acid or region thereof and leads to the unambiguous assignment of both known and previously unknown sequence variations.

The present invention is also directed to methods for the diagnostic sequencing (also referred to as re-sequencing) of all or part of a sample nucleic acid, i.e. the determination of the presence, the nature and the location of the sequence variations that occur relative to a related known reference sequence. The sequence variations may either be previously identified or hitherto unknown. Diagnostic sequencing according to the present invention may focus on particular positions in a nucleic acid sequence, e.g. when scoring previously known mutations or polymorphisms.

The term "mapping", as used herein, will be understood to include both the characterization, i.e. determination of the nature, and the position of the sequence variations.

The terms "target DNA", "target sequence", "target nucleic acid" and the like, as used herein, refer to the sequence region which is to be sequenced or re-sequenced entirely or in part as well as to the nucleic acid material that is actually subjected to one or more complementary cleavage reactions.

The terms "reference nucleic acid sequence", "related sequence", "previously known sequence", and the like, refer to a nucleic acid region, the sequence of which has previously been determined which corresponds to the target. The reference and target sequences may be found to be identical or may differ. The reference sequence need not derive from the same species. In many applications, several different sequence variants will be available as reference. The differences between a target sequence and its reference sequence may be simple (e.g., single nucleotide substitutions, deletions and insertions; microsatellite polymorphisms) or complex (e.g., substitution, insertion, and deletion of multiple nucleotides). In certain situations, one may not know in advance to what reference sequence, if any, the target nucleic acid corresponds. In such situations the interrogated target sequence typically corresponds to a portion of a (much) larger reference sequence and/or to one out of a plurality of different references.

The terms "unambiguous", "unique", "unequivocal", and the like, are used to indicate that only a single sequence variation or combination of sequence variations can explain the observed mass spectral changes.

The terms "complementary (cleavage) reactions", "complementary cleavages" and the like, as used herein, refer to target nucleic acid digestions characterized by varying specificity [e.g., stringent or relaxed mono- and di-nucleotide specificity; digestion with a combination of reagents; partial cleavage] and/or to digestion alternative forms of the target sequence [e.g., the complementary (+) and (−) strands; incorporation of modified subunits; analysis of variable portions of the target sequence].

The terms "transcript" and "transcription", as used herein, refer to the synthesis of a nucleic acid polymer by means of an RNA polymerase. In addition to canonical subunits (having a 2′-OH group), a transcript may incorporate non-canonical substrates (having any other substituent than a hydroxyl group at the 2′-position). Canonical and non-canonical substrates may contain additional modifications.

The term "genotyping," as used herein, refers to determining the genetic constitution, which is the particular set of alleles inherited by the organism as a whole, or the type of allele found at a particular locus of interest.

The term "expression profiling," as used herein, refers to method(s) for determining the mRNA expression profile of a given cell or a population of cells at a given time under a given set of conditions.

Nucleotides are designated as follows. A ribonucleoside triphosphate is referred to as NTP or rNTP; N can be A, G, C, U or $m^5U$ to denote specific ribonucleotides. Likewise, deoxynucleoside triphosphate substrates are indicated as dNTPs, where N can be A, G, C, T, or U. Throughout the text, monomeric nucleotide subunits are denoted as A, G, C, or T with no particular reference to DNA or RNA. When necessary, the nature of the nucleoside monophosphates is clarified by the use of more specific abbreviations such as U, $m^5U$, CMP, and UMP to refer to ribonucleotides and dC, dU, dCMP, dUMP and dTMP to indicate deoxynucleotides. Note that T is not an alternative designation for $m^5U$.

Sequencing via Non-Ordered Sets of Specific Cleavage Fragments

The methods of the present invention allow the interrogation every position in a given target sequence without creating a fragment-ladder, i.e. a nested set of fragments that share one common endpoint. The method comprises, in part, subjecting one or more target nucleic acids to a set of complementary mononucleotide- and/or dinucleotide-specific cleavages, the products of which are analyzed by mass spectroscopy (MS). A preferred method according to the invention includes the specific cleavage of the one or more target nucleic acids at each nucleotide by way of two or more separate reactions. The digestion products obtained in mononucleotide- and dinucleotide-specific cleavage reactions such as those described herein range from mononucleotides to fragments of a few tens of nucleotides and are particularly well suited for analysis by MS. This aspect of the invention overcomes the technical limitation of the short read lengths encountered when analyzing fragment-ladders under the current MS performance. The mass spectra obtained with the methods do not provide a simple readout of the sequence. Computational approaches provided herein allow the comparative analysis of the obtained spectra with those known or predicted for the related reference sequence.

The ability to detect and map sequence variants based on the non-ordered set of cleavage fragments according to the present invention resides in part in the combination of the various complementary site-specific reactions. For example, one cleavage scheme useful in the practice of the present invention makes use of the mononucleotide-specific ribonuclease-T1 (RNase-T1, G-specific) and RNase-U2 (A-specific; the limited specificity of this enzyme is recognized and will be dealt with below). Both purines (A/G) and pyrimidines (C/T) in a target nucleic acid can be examined by cleaving an RNA copy of the two complementary strands of a target nucleic acid with both enzymes. MS analysis of the fragments generated by only a single mononucleotide-specific reaction would detect the presence of most sequence variations but only a minority of the mutations—in essence those affecting the nucleotide that is recognized—would also be localized. Since the methods of the present invention examine each of the four bases in a given sequence, each of the twelve possible nucleotide substitutions result in the loss of one cleavage site and the concomitant gain of another cleavage site. This principle is illustrated in Table I for the RNase-T1 and RNase-U2 cleavage reactions on the two complementary transcripts of a hypothetical target nucleic acid. Transitions affect both the RNase-T 1 and RNase-U2 cleavage patterns of either the (+) or the (−) strand. As can be seen in Table 1, all transversions change the cleavage pattern of both strands of the transcript: they affect either one of the RNase digests on both strands, or the T1 digest of one strand and the U2 digest of the complementary strand. In addition to altering two cleavage patterns, each single nucleotide substitution also affects the molecular mass of one fragment in each of the remaining two digestion reactions (Table I). In conclusion, complementary cleavage reactions of the present invention results in a high degree of built-in redundancy. Each nucleotide substitution is potentially associated with a maximum of ten differences (data points) with respect to the reference spectrum. The loss and gain of a cleavage site are associated with both the disappearance and appearance of three peaks; two additional peaks undergo a shift as a result of a mass difference. In practice, the 1 Da mass difference between C and U(T) may result in the loss of a significant amount of information (Table I). More particularly, in G- and A-specific cleavage reactions, the C/U transitions may go unnoticed while the observed mass difference may not be unambiguously assigned to a certain transversion. However, in preferred methods of the present invention directed to the analysis of RNA target sequences the method makes use of C and/or U analogs that exhibit more favorable mass differences, thus allowing the unambiguous assignment of the mass difference to a particular transversion. Example 1 and Table I illustrate that 5-methyluridine is an example of such a useful analog [$m^5U$; R. I. Chemical, Orange, Calif.; see also to Hacia J. et al., *Nucleic Acids Res.* 26: 4975–4982 (1998) for the incorporation of $m^5UTP$ during in vitro transcription reactions].

Figure 1B:
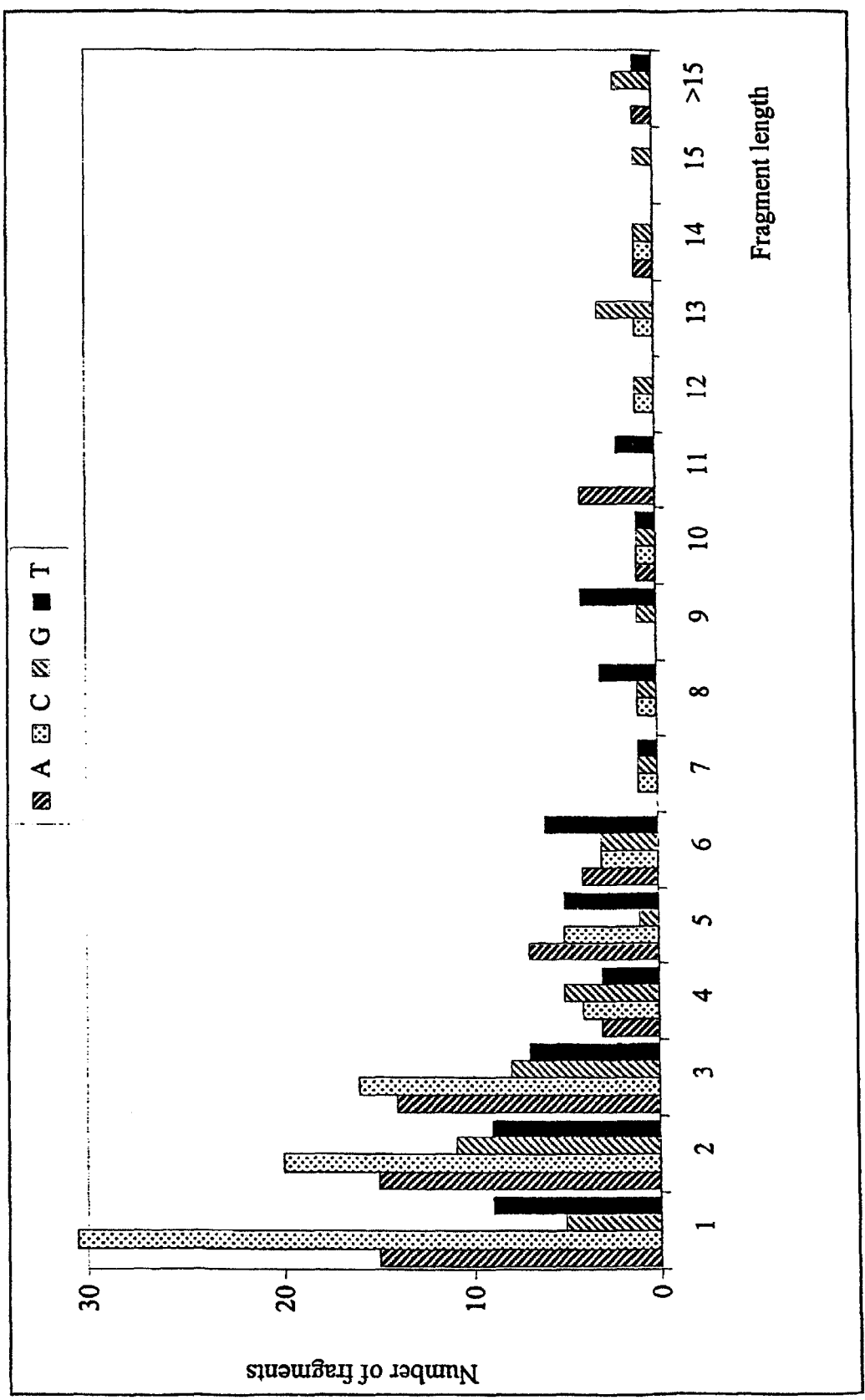
FIG. 1B shows the size distribution of the products that result from base-specific cleavage of a 245 nucleotides long exemplary sequence.

FIG. 1A shows, by way of example, a 120-nucleotide segment of exon 5 of the p53 gene as well as a graphical representation of the digestion products generated by RNase-T1 and RNase-U2 on an RNA copy of each strand. FIG. 1B displays the size distribution of the base-specific digestion fragments derived from another exemplary sequence and illustrates that mono-, di- and tri-nucleotides are considerably more numerous than the larger digestion products. This distribution is expected for mononucleotide specific cleavage reactions that generate fragments with an average length of four nucleotides. Contrary to the size distribution, the number of different molecular masses that oligonucleotides can assume rapidly increases with the size of the fragment. Because of the constrained composition of digestion products (e.g. only one G in the case of RNase-T1), the number of molecular masses of mono-, di- and tri-nucleotides is limited to 1, 3 and 6, respectively. Consequently, mono-, di- and tri-nucleotides are often non-informative in the methods of the present invention because their number exceeds the limited mass space. FIG. 1A illustrates that in certain parts of the target sequence one of the cleavage reactions produces many small fragments due to an over-representation of the recognized nucleotide and, consequently, yields virtually no information. However using the method of the present invention, this problem is minimized by the complementary nature of the four reactions which ensures that the fragments derived from the same region by the other digestions (interrogating under-represented nucleotides) are correspondingly larger. This indicates a basic attribute of the methods of the present invention. Each of the four cleavage reactions yields information about a particular mutational alteration (see Table I) and, in general, the redundancy in this information enables the identification of the mutation (nature and location) even when part of the information is missing from the spectra as described above.

The methods of the present invention are therefore largely, yet not completely, sequence-independent and permits the re-sequencing of virtually any variation. Computer simulations of diagnostic sequencing by the present methods, more particularly those involving digestion of RNA copies of each strand with the RNases T1 and U2, have shown that for target sequences of up to three hundred base-pairs ~90% or more of all possible single nucleotide substitutions are associated with $\geq 4$ data points. Fewer than 1% of the substitutions do not result in spectral changes. More than 95% of all possible single nucleotide substitutions give rise to unique spectral changes and can therefore be unambiguously identified (see Example 1 and FIGS. 3 and 4).

In summary, deduction of the sequence according to the methods of the present invention is based on the integration of the information that resides in a complementary set of 'mass-fingerprints' as well as the previous knowledge about a related reference sequence. The relationship between this multitude of data allows inferring the presence, nature and position of sequence variations in an unambiguous way. It is illustrative of the method that the derivation of the sequence is not critically dependent on the accuracy, i.e., the absolute values of the mass measurements. It is rather the coherent ensemble of mass-shifts and appearances/disappearances of cleavage sites that uniquely define the sequence. The computer simulations, described herein, assumed a resolution of 5 Da or 0.1%, a figure which is well above what can be achieved with state-of-the-art equipment. Also, it should be pointed out that the determination of the correct base composition is limited anyway to short fragments, even in the case of high-precision measurements [e.g., 5-mers in the case of unrestrained sequences and if the measurement has an accuracy of 0.01% or better; Limbach P., *Mass Spectrom. Rev.* 15: 297–336 (1996)]. Other methods in the art, which involve the accurate mass determination to assign the correct base composition to one or more fragments, will generally permit the detection of most sequence variations but not their unequivocal mapping. In these experiments it is generally assumed that a certain experimental observation relates to one particular previously known sequence variation, ignoring the fact that alternative sequence variations can explain the same result.

The present invention encompasses several additional embodiments and aspects described hereinafter and certain other embodiments will be readily apparent to one of ordinary skill in the art.

Target Nucleic Acid Preparation and Fragmentation (a) Derivation of Target Nucleic Acid and Approaches to Cleaving with Base-Specificity Nucleic acid molecules can be isolated from a particular biological sample using any of a number of procedures, which are well-known in the art, the particular isolation procedure chosen being appropriate for the particular biological sample. To obtain an appropriate quantity of isolated target nucleic acid on which to perform the methods of the present invention, amplification of the target nucleic acid may be necessary. Examples of appropriate amplification procedures for use in the invention include but are not limited to: cloning [Sambrook et al., *Molecular Cloning: A Laboratory Manual*, Cold Spring Harbor Laboratory Press (1989)], polymerase chain reaction (PCR) [Newton C. R. and Graham A., PCR, BIOS Publishers (1994)] and variations such as RT-PCR [Higuchi et al., *Bio/Technology* 11: 1026–1030 (1993)] and allele-specific amplification (ASA), strand displacement amplification (SDA) [Terrance Walker G. et al., *Nucleic Acids Res.* 22: 2670–77 (1994)], and transcription based processes.

One embodiment of the present invention is directed to methods for sequencing (re-sequencing, etc.) Nucleic acid comprising the digestion of an RNA copy of each strand of the target nucleic acid with the RNases T1 and U2. One of the advantages of the method is the use of RNA, which exhibits higher sensitivity and better stability in MALDI-MS compared to DNA [Hahner S. et al., *Nucleic Acids Res.* 25: 1957–1964 (1997)]. Typically, the first stage of this aspect of the invention involves the amplification of the target nucleic acid by PCR or reverse-transcription followed by PCR. (RT-PCR) This can be achieved with a pair of dedicated primers that incorporate promoter sequences as non-annealing 5'-extensions. In a second stage, these promoters are used for the specific transcription of the adjacent sequences including the target sequences. Preferably, the promoter sequences are small and permit the in vitro transcription by a single subunit cognate RNA polymerase such as those deriving from bacteriophage T7, T3 and SP6. Preferred for use in this aspect of the invention are C and/or U analogs that can be incorporated during transcription and that exhibit favorable mass differences [e.g. m$^5$U; supra]. The use of PCR primers that carry different promoter sequences permits the generation of an RNA copy of both strands in two parallel strand-specific transcription reactions. Both strands may also be transcribed from the same promoter sequence: this requires two parallel amplification reactions with only one promoter tagged primer. Alternatively, the in vitro transcripts may also be produced from sequences cloned in special purpose vectors such as the pGEM-type vectors available from Promega (Madison, Wis.) which contain appropriate promoters. The third step further comprises the treatment of the resultant RNA transcripts with one or more complementary mononucleotide-specific RNases (e.g RNase-T1 and RNase-U2), such that each desired position in the target sequence is interrogated. The final step in the process consists of the mass-spectrometric analysis of the RNA fragments resulting from the complementary cleavage reactions and the comparison of the spectra obtained with those of the known reference sequence.

Alternative schemes to prepare target nucleic acid obtained from a biological sample and to subject the target sequence to a set of complementary mononucleotide-specific cleavage reactions are also within the scope of the invention. The target nucleic acid can be DNA, cDNA, any type of RNA, DNA/RNA hybrid, or of mosaic RNA/DNA composition [depending on the ratio of ribo- and deoxyribonucleoside triphosphates (rNTP/dNTP) in the synthesis reaction; Sousa R. and Padilla R., *EMBO J.* 14: 4609–4621 (1995); Conrad F. et al., *Nucleic Acids Res.* 23: 1845–1853 (1995)]. The target sequence may also include modifications that are either introduced during or after enzymatic synthesis.

In general, different forms of each target sequence will be prepared so as to be able to perform a complementary set of mono-specific cleavage reactions. The cleavage reactions may be performed enzymatically and/or chemically. The mononucleotide-specificity of the digestion reactions may reside in the cleaving agent (e.g RNase T1), in the structure of the target nucleic acid, or in a combination of both. For example, RNase A (specific for both C- and U-residues) can be made monospecific by modifications of the substrate sequence that block the ribonucleolytic action at C or U residues. RNase A cleavage at U residues can in theory be prevented by chemical modification [Simoncsits A. et al., *Nature* 269: 833–836 (1977)]. The enzymatic incorporation of nucleotide analogs, most notably those modified at the 2'-hydroxyl group of the ribose is particularly preferred in the practice of the invention. A variety of such analogs have been demonstrated to be substrates for T7 RNA polymerase; e.g. 2'-fluoro, 2'-amino [Aurup H. et al., *Biochemistry* 31: 9636–9641 (1992)], 2'-O-methyl [Conrad F. et al., *Nucleic Acids Res.* 23: 1845–1853 (1995)], as well as 2'-deoxy NTPs [Sousa R. and Padilla R., *EMBO J.* 14: 4609–4621 (1995); Conrad F. et al., *Nucleic Acids Res.* 23: 1845–1853 (1995)]. The above strategy may also be used to improve the specificity of certain RNases such as RNase U2 which is said to cleave GpN phosphodiester bonds in extensive digests [Brownlee G., in "*Laboratory Techniques in Biochemistry and Molecular Biology*" (Work T. S. and Work E., eds.), North-Holland, Amsterdam, pp 199–200 (1972)]. Mosaic DNA/RNA target sequences that incorporate only one specific rNTP and that can be obtained quite efficiently with particular mutant polymerases [Sousa R. and Padilla R., *EMBO J.* 14: 4609–4621 (1995); Gao G. et al., *Proc. Natl. Acad. Sci. USA* 94: 407–411 (1997); Bonnin A. et al., *J. Mol. Biol.* 290: 241–251 (1999)], may allow mono-specific cleavages by alkaline treatment or by digestion with a non-specific RNase such as RNase-I [Meador J. et al., *Eur. J. Biochem.* 187: 549–553 (1990)].

Alternative strategies to obtain selective cleavage of target sequences make use of phosphorothioate chemistry. DNA and RNA polymers with phosphorothioate internucleoside linkages in the Rp stereo-configuration are readily synthesized [see Eckstein F., *Ann. Rev. Biochem.* 54: 367–402 (1985) and references cited therein]. Such phosphorothioate linkages can be specifically hydrolyzed following alkylation [Gish G. and Eckstein F., *Nucleic Acids Symp. Ser.* pp 253–256 (1987); Gish G. and Eckstein F., *Science* 240: 1520–1522 (1988)]. Mono-nucleotide specific fragmentation according to this aspect of the invention would require the synthesis of targets making use of one particular α-thio nucleotide triphosphate substrate. Some nucleases (e.g. nuclease P1) cannot hydrolyze Rp phosphorothioate diesters; indirect selective cleavage (at a natural phosphodiester) may thus be obtained with target sequences that incorporate three different αS-dNTPs (or αS-rNTPs).

(b) Alternative complementary reactions

Figure 4:
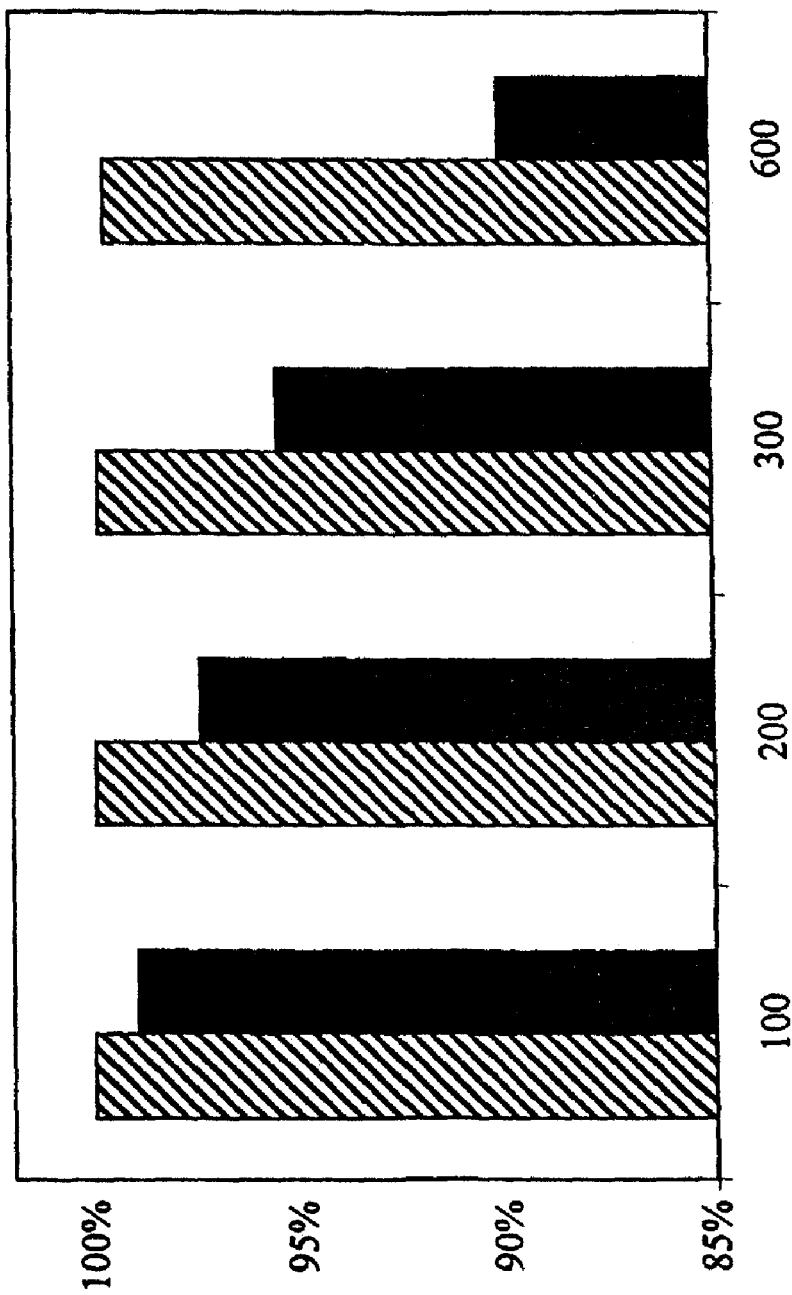
FIG. 4 summarizes the results of the mutational simulation analysis of 1.200 base-pair sequence of HIV and shows the percentages of the single nucleotide substitutions that can be detected (hatched bars) and mapped unambiguously (filled bars) as a function of the length of the interrogated segments.

The performance of the present sequencing methods will be understood by those skilled in the art to be dependent on the following interrelated factors: (1) the length of the region to be sequenced, (2) the resolution of the MS analysis, and (3), to some extent, the sequence itself. The longer the region of interest and, consequently, the larger the number of digestion products, the more important the resolution becomes. Also, the length of the region to be sequenced is directly proportional to the number of single nucleotide substitutions that cannot be unambiguously mapped on the basis of the four base-specific fragmentation patterns only (Example 1; FIG. 4). Some sequence motifs are intrinsically difficult to sequence. An example of such a sequence is $CTAGC_1C_2C_3C_4C_5GATC$ (SEQ ID NO: 15), where mutations at $C_1$ and $C_2$ cannot be discriminated from the same type of mutations at $C_5$ and $C_4$, respectively. Another such sequence is $GAG_1A_2G_3A_4GA$, where $G_1$->A cannot be discriminated from the $G_3$->A mutation; similarly, $A_2$->G and $A_4$->G cannot be distinguished. Finally, the four mono-nucleotide specific cleavages may also be insufficient to analyze complex sequence variations (see discussion below). Most preferably, therefore, the practicing of the present invention includes a computer-aided simulation of the re-sequencing strategy of the intended region. Such simulation and analysis will reveal possible problematic positions in the sequence and can be used to assess the usefulness of certain additional complementary cleavage reactions as countermeasures to overcome such sequencing difficulties.

One such measure consists of dividing the target region and deriving two or more (partially overlapping) segments (e.g., amplicons) from the sample nucleic acid rather than sequencing the target region as a whole. In addition to setting the length, this allows to exert some control over the composition. This would abrogate problems arising when the region of interest contains a duplicated segment. A second measure consists of carrying out one or more alternative or additional reactions involving target fragments that incorporate one or more modified nucleotides that exhibit different molecular masses such as is described above. Those of skill in the art will know of the existence of a wealth of mass-modified nucleotide analogs, many of which are useful and can be reconciled with the enzymatic procedures of the present method. The nucleotide analogs will differentially affect the masses of many of the digestion products and will therefore yield a significantly different spectrum that may reveal the required information. The analogs U and $m^5U$ [supra] exemplify this. Simulation studies (which model the present invention) have indicated that the use of U resolves certain sequence ambiguities observed with $m^5U$ (data not shown), while overall the latter nucleotide analog results in considerably fewer sequence ambiguities (see Example 1).

Another option consists of performing one or more additional reactions on the complementary strand. Compared to, for example, a G-specific cleavage of one strand, the C-reaction of the complementary sequence will yield a different set of fragments characterized by other mass differences. The effect of including reactions on the complementary strand of the target sequence is therefore similar to the use of nucleotide analogs.

Still another alternative provided by the present invention and which is useful in obviating the potential problems exemplified above includes using reactions with alternative specificities of cleavage. For example, partial base-specific cleavage can be achieved by changing the reaction conditions or by use of a specially prepared target wherein the cleavable and uncleavable (e.g. 2'-modified; supra) forms of one particular nucleotide occur randomly. Alternatively, instead of partial base-specific cleavages, one or more specific digestions characterized by a greater stringency can be performed (e.g. dinucleotide- or relaxed dinucleotide-specificity; see below). The digestion of the target sequence, in double stranded DNA form, with restriction enzymes is still another alternative provided by the present invention. Double digestion (i.e. a combination of two base-specific cleavages) of target nucleic acid alone or in combination with other digestion methods of the present invention also represents an informative alternative within the scope of the present invention.

Another informative option within the scope of the present invention involves the analysis of truncated target sequences. More specifically, cleavage of chain terminated sequences prepared, for example, by incorporation of a particular 3'-deoxy nucleotide substrate, will yield spectra that contain additional fragments when compared to the spectrum of the full target nucleic acid and will consequently provide additional information that will, in certain cases, allow a more unambiguous indemnification of sequence variation. This approach will be particularly useful for the characterization of lengthy digestion products or regions containing complex sequence variations.

(c) Alternative Complementary Reactions: Cleavage Characterized by a Greater than Mononucleotide Specificity In still another of its embodiments, the method of the present invention also includes nucleolytic processes that are characterized by a dinucleotide- or a relaxed dinucleotide-specificity. Such stringency of cleavage will facilitate the analysis of longer target sequences because the size distribution of the resultant digestion products is even better suited for analysis by MS than fragments with an average length of 4 nucleotides that are generated by mononucleotide-specific cleavage. Useful in this aspect of the invention are, for example, restriction endonuclease reagents capable of cutting DNA at dinucleotide sequences such as those described by Mead D. et al., WO 94/21663 (PCT/US94/03246). RNases that preferentially hydrolyze pyrimidine-adenosine (CA and UA) bonds have also been identified which are useful in the practice of the present invention [*E. coli* RNase-M, Cannistraro V. and Kennell D., *Eur. J. Biochem.* 181: 363–370 (1989); as in an endoribonuclease isolated from *Saccharomyces cerevisiae*, Stevens A. et al., *J. Bacteriol.* 164: 57–62 (1985); and as is the *Enterobacter* sp. C-ribonuclease, described by Marotta C. et al., *Biochemistry* 12: 2901–2904 (1973)]. As disclosed and exemplified in the present invention, the specificity of these enzymes can, if need be, essentially be restricted to CA- or UA-bonds by the use of target nucleic acids that incorporate dUMP (or dTMP) on the one hand and dCMP on the other hand.

Stringent or relaxed dinucleotide-specific cleavage may also be engineered through the enzymatic and chemical modification of the target nucleic acid. By way of non-limiting example, transcripts of the nucleic acid of interest may be synthesized with a mixture of regular and α-thio-substrates and the phosphorothioate internucleoside linkages may subsequently be modified by alkylation using reagents such as an alkyl halide (e.g. iodoacetamide, -iodoethanol) or 2,3-epoxy-1-propanol. The phosphotriester bonds formed by such modification are not expected to be substrates for RNases. Using this procedure, a mono-specific RNase, such as RNase-T1, can be made to cleave any three, two or one out the four possible GpN bonds depending on which substrates are used in the α-thio form for target preparation. The repertoire of dinucleotide-specific reagents useful in the practice of the present invention may be further expanded by using additional RNases, such as RNase-U2 and RNase-A. In the case of RNase-A, the specificity may be restricted to CpN or UpN dinucleotides through the enzymatic incorporation of the 2'-modified form of the appropriate substrates as described above. For example, to make RNase-A specific for CpG dinucleotides, a transcript (target) is prepared using the following substrates: αS-dUTP, αS-CTP, αS-ATP, and GTP. Thus, using the indicated methods described herein, it is possible to engineer all 16 dinucleotide specificities. However, not all dinucleotide-specific reagents described herein would be required if the complementary strand of the target nucleic acid is included in the analysis.

The strategy outlined above makes it possible to prevent cleavage within homopolymer tracts (stretches of A's, G's, C's or T's) by an RNase that is made specific (or is made specific as described above) for the repeated nucleotide. Indeed, incorporation of a particular αS-NTP, followed by alkylation, will selectively prevent cleavage within repeated stretches of that nucleotide, allowing cleavage to occur at the 3'-side of the last nucleotide in the repeat. Simulation studies, similar to those described in Example 1, have identified this as a particularly useful strategy. Sequence analysis by digestion of the two complementary strands with RNase-T1 and RNase-U2 yielded a 5- to 10-fold reduction in the number of ambiguous mutations when αS-GMP and αS-AMP were incorporated in the respective transcripts. These studies also suggest that the selective blockage of cleavage within repeats is accompanied by a relatively small increase in the average length of the digestion products, thereby resulting in considerably less loss of information.

Those of skill in the art will also readily recognize variations or alternatives in certain aspects of the fragmentation methods described herein. Such alternatives or variations encompassed by the present invention include but are not limited to:

1. the use of other or additional RNases (alone or in combination) having similar or alternative specificities;
2. the use of mutant or chemically modified RNases with useful characteristics vis-a-vis the methods of the present invention [see for example, Loverix S. et al., *Nature Struct. Biol.* 5: 365–368 (1998) for an RNase T1 mutant that prefers the phosphorothioate analog over the natural phosphodiester substrate; see also Contreras R. and Fiers W., *FEBS Lett.* 16: 281–283 (1971) for the production of limited digests with a chemically modified RNase];
3. the use of other nucleotide analogs that exhibit different masses and/or reactivities, including nucleotides that incorporate alternative isotopes; and
4. alternative specific fragmentation methods, either chemical [Maxam A. and Gilbert W., *Proc. Natl. Acad. Sci. USA* 74: 560–564 (1977); Richterich P. et al., *Nucleic Acids Res.* 23: 4922–4923 (1995)], or enzymatic.

Multiplex Reactions

In another embodiment, the methods of the present invention are directed to the simultaneous sequence determination of at least two non-contiguous regions in a sample nucleic acid. In contrast to traditional sequencing methods that generate a fragment-ladder (i.e. a nested set of fragments that share a common endpoint), the strategies outlined herein are equally useful for multiplex sequencing. Multiplex sequencing, according to the present invention, generally involves the co-amplification of selected regions of target nucleic acids. This can be achieved by using sets of dedicated primer pairs which flank or are co-terminal with a target nucleic acid to be amplified. Alternatively, the preparation of the multiple target nucleic acids comprises the concomitant amplification of restriction fragments derived from the sample nucleic acid. Some approaches are illustrated and exemplified in Example 5. A special case of multiplex sequencing consists of the simultaneous analysis of the two complementary strands of a double stranded target nucleic acid.

In yet another embodiment, the methods of the present invention can be used for the simultaneous sequence determination of the corresponding target region(s) of at least two biological samples. A sequence variation in one out of a pool of analogous target nucleic acids may go unnoticed when analyzing conventional sequence ladders by means of gel electrophoresis. With the present methods, a sequence variation will, as a rule, yield one or more distinct peaks in the various complementary mass spectra. This feature should allow the detection of mutations at a significantly lower ratio of mutant to wild-type allele and therefore permit the analysis of larger pools. The ability to pool renders the present methods useful for the discovery of sequence variations across particular target regions in a given population. For this application, typically 5–10 samples may be combined. In case the mutations have previously been identified, considerably more samples, e.g. several tens, can be combined. The characteristics that render the present method useful for the analysis of sample pools make the method also effective for the analysis of heterozygous samples (i.e., an equimolar mix of two alleles).

Mass Spectrometric Methods

Mass-spectrometric methods useful in the practice of the present invention include ionization techniques such as matrix assisted laser desorption ionization (MALDI) and electrospray (ES). These ion sources can be matched with various separation/detection formats such as time-of-flight (TOF; using linear or reflectron configurations), single or multiple quadrupole, Fourier transform ion cyclotron resonance (FTICR), ion trap, or combinations of these as is known in the art of mass spectrometry. [Limbach P., *Mass Spectrom. Rev.* 15: 297–336 (1996); Murray K., J Mass Spectrom., 31: 1203–1215 (1996)].

Because the present methods generally require the analysis of complex oligonucleotide fragment mixtures, the MALDI approach, mostly resulting in singly charged molecules, is preferred over ES where significant multiple charging will further increase the number of spectral peaks. For the desorption/ionization process, numerous matrix/laser combinations can be employed.

Sequence Determination of Simple Versus Complex Variations

In another embodiment, the methods of the present invention are directed to the diagnostic sequencing of one or more target nucleic acids that, in comparison with a related reference nucleic acid, incorporates a sequence variation other than a single nucleotide substitution. Such a sequence variation can involve the deletion or insertion of one or more nucleotides as well as the substitution of multiple nucleotides.

Similar to single nucleotide substitutions, the insertion or deletion of a single nucleotide represents a simple sequence variation whose analysis using methods of the present invention is straightforward. Both of these types of sequence variations are associated with a characteristic set of (maximum nine) changes in the four complementary mononucleotide-specific fragmentation patterns. It will be understood that the methods of the present invention, similar to other sequencing methods, may not unambiguously locate the point of insertion or deletion when it concerns one nucleotide in a stretch of identical nucleotides. This, however, may be taken into consideration when performing a computer assisted analysis of whether the observed spectra relate in a unique way to a specific sequence variant in accordance with the practice of the present invention.

Analysis of a microsatellite DNA [also referred to as VNTR (variable number tandem repeat) or SSR (simple sequence repeat)] represents a special case whose analysis is readily achieved using the methods of the present invention. Although multiple nucleotides are involved with VNTRs or SSRs, the interpretation of the spectral changes on the basis of the known reference sequence is rather simple and the polymorphism (an altered number of repeat units) may readily be characterized.

The methods of the present invention may also be used to analyze more complex sequence variations such as those where multiple nucleotides are affected either through insertion, deletion, substitution or a combination thereof. The analysis of a number of double and triple mutants is described below in Example 3d. Multiple substitutions within a target sequence are also expected to be accompanied by a characteristic number of spectral changes. This number depends on whether the substitutions are adjoining or separated, as well as on the intervening sequence in case the mutations are separated. Single nucleotide substitutions, isolated by a sequence that contains at least one A, G, C, and T, are each associated with 10 spectral differences as outlined above. In general, the analysis of complex sequence variants will require (elaborate) computational approaches. One possible algorithm involves the comparison of the experimentally observed spectra with those generated on the basis of all possible sequences in the short region to which the sequence variation is confined. Such an algorithm will identify the sequence variant or, in case of ambiguities, the different matching sequences. This procedure illustrates that the present methods may be applied to the de novo sequencing of short regions of a target sequence. It will be recognized that, in practice, the experimental observations will not only set the boundaries but will also define the length of the variant region such that the algorithm need not consider insertions or deletions. Additional experimentally derived information, such as the absence of a particular nucleotide, can further limit the sequence space the algorithm has to explore. In particular applications, the complex sequence variants may be previously known and may thus be part of the set of reference sequences. In such cases, the experimentally observed spectra may be directly correlated to those predicted for the reference sequences. There would however still be a need to compute whether such correlation is unique. The advantage of previous knowledge is that the experimental approach can be adapted such that the output information indeed relates uniquely to the potentially occurring complex sequence variations.

Computer Algorithm

The present invention, in part, rests on the insight that computational analysis of the spectra obtained in a set of complementary cleavage reactions, and comparison of these data with the computationally predicted spectral changes from the known reference sequence, as illustrated herein, is an important step in the unambiguous determination of the presence, the nature and the location of sequence variations. More specifically, the computational approaches to simulate the experiment illustrated herein are necessary to determine whether a unique relation exists between the spectra obtained and a particular sequence variation. Accordingly, one aspect of the present invention contemplates a method which utilizes a computer algorithm or method capable of computing the spectral differences resulting from one or more nucleotide differences between the target nucleic acid and the reference nucleic acid, the method and algorithm comprising subjecting the reference nucleic acid and sequence variants thereof (i.e., target nucleic acid having nucleotide differences) to the different base specific cleavages to generate oligonucleotide fragments, computing the mass of each oligonucleotide fragment, generating the mass spectra of the oligonucleotide fragments from the reference nucleic acid and the sequence variants thereof for each of the base specific cleavage reactions, and matching these computationally derived mass spectra with the spectra obtained experimentally in the different base specific cleavage reactions.

In one preferred embodiment the computer algorithm is designed to systematically compute the spectra of all possible simple nucleotide variations of the reference nucleic acid, including but not limited to all possible single nucleotide substitutions, deletions and insertions. Since most of the genetic diversity found in living organisms involves single nucleotide variations, most of the experimentally observed sequence variations can be identified with the methods and algorithms of the present invention, meaning that one or more matches may be found between the observed spectra and the computationally derived mass spectra. In case a unique match is found, the sequence variation in the target nucleic acid is unique. When more than one match is found between spectra, the sequence variation cannot be established unambiguously.

It will be obvious to the person skilled in the art that different approaches may be used for performing the computational analysis, such as, but not limited to, performing the computational analysis on the complete reference sequence, or performing a serial computational analysis on segments of the reference sequence using, for example, a sliding window. The latter approach will enable the identification of different sequence variants occurring in different parts of the reference sequence.

In another embodiment, the methods and computer algorithms of the present invention are designed to explore all possible nucleotide sequences in a limited segment of the reference sequence. Such methods and algorithms may be used when the preceding approach fails to give a match, demonstrating that the sequence variation does not correspond to a simple nucleotide variation in the reference nucleic acid. This may be the case when more than one nucleotide change occurs within a short region, such that one or more cleavage products contain multiple nucleotide alterations. The region corresponding to these cleavage products can then be explored further by computing the spectra for all possible sequence permutations and determining the matching sequence. It is anticipated that given sufficient computing power, such methods and algorithms may be used for de novo sequencing using mass spectral data generated according to the present invention.

Applications of the Present Methods

The methods of the present invention are particularly well suited for rapidly and accurately re-sequencing nucleic acids from a variety of biological sources including, but not limited to, plants, animals, fungi, bacteria and viruses. Re-sequencing implies the detection and mapping of both previously known as well as unknown sequence variations (e.g. mutations and polymorphisms) relative to a related reference sequence. One of the most notable distinctions with respect to conventional gel-electrophoretic analysis of fragment ladders, is that generally each particular sequence (variation) results in a distinct and characteristic set of (mass) peaks. This feature makes the present methods effective for the reliable scoring of heterozygous samples, the simultaneous sequencing of multiple target regions from a single biological sample (i.e., multiplexing), as well as the simultaneous analysis of the analogous regions from different samples (i.e., pooling). The use of pools of individual samples should permit the cost-effective identification of previously unknown sequence variations in a population. This aspect of the invention properties makes the present methods valuable for clinical and public health studies. Very often such studies rely on samples (e.g., saliva, blood, swabs, paraffin-embedded tissue, biopsy material) that are cellularly and genetically heterogeneous and, consequently, require assays that can detect mutations at a low ratio of mutant over wild-type allele.

An additional advantage of the present methodology is that it can be tuned (by reducing the number of complementary cleavage reactions) such that the diagnostic sequencing is limited to particular positions in a target nucleic acid, a feature useful for the unambiguous scoring of previously identified mutations or polymorphisms. The processes described herein can be used, for example, to diagnose any of the more than 3000 genetic diseases currently known (e.g., hemophilias, thalassemias, Duchenne Muscular Dystrophy, Huntington's Disease, Alzheimer's Disease and Cystic Fibrosis) or genetic defects yet to be identified. In addition, certain DNA sequences may predispose an individual to any of a number of diseases or conditions such as diabetes, artherosclerosis, obesity, various autoimmune diseases and cancer (e.g., colorectal, breast, ovarian, lung). Depending on the biological sample, the diagnosis for a genetic disease or genetic predisposition can be performed either pre- or post-natally using the methods of the present invention. Re-sequencing of nucleic acids derived from infectious organisms using the methods of the present invention may reveal the basis of pathogenicity and may also be useful to identify the variation(s) that cause drug-resistance. For example, mutations in the protease/reverse transcriptase region of the human immunodeficiency virus (HIV) have been implicated in the decreased sensitivity towards the antiviral activity of protease and reverse transcriptase (RT) inhibitors. The re-sequencing of the nucleic acid encoding these viral domains is therefore of special interest to monitor disease progression (see Example 1). Similarly, sequencing, according to the present invention, may be useful to determine the antibiotic-resistance phenotype of certain bacteria [e.g. *Mycobacterium tuberculosis*; Head S. et al., *Mol. Cell. Probes* 13: 81–87 (1999); Troesch A. et al, *J. Clin. Microbiol.* 37: 49–55 (1999)].

In other embodiments, the present methods are directed to the identification and classification of target nucleic acids. Analyses according to the present invention characterize nucleic acids at a level essentially equal to sequence determination. Therefore, interrogated unknown sequences may be unambiguously identified by comparison of the obtained mass spectra with those known or predicted for a plurality of reference sequences. In this exercise, novel sequences that have no matching reference database sequence may also be found. The use of the methods for expression profiling (i.e., the analysis of cDNA libraries) as well as whole-genome sequencing is exemplified in Example 6 and 7, respectively. Other applications include the determination of identity or heredity (e.g., paternity or maternity).

Kits for Practicing the Invention

Kits for diagnostic sequencing of one or more target nucleic acids in a sample are also provided. In preferred embodiments, such kits comprise one or more reference nucleic acids, various reagents for sequence specific cleavage protocols, and computer algorithm(s). Such kits may optionally also contain nucleic acid amplification reagents. Additionally, the kits may contain reagents for the preparation of modified nucleic acids, including but not limited to modified nucleotide substrates. The kits may also contain buffers providing conditions suitable for certain enzymatic or chemical reactions. In addition, the kits may contain reagents, such as solid supports, for purposes of isolating certain nucleic acids and preparing nucleic fragments for mass spectrometric analysis.

The foregoing aspects of the invention are illustrative and should not be construed to limit the invention as set out in the appended claims. Variations in some aspects as well as alternative procedures will be readily recognized by one of ordinary skill in the art.

Example 1 describes modeling the diagnostic sequence analysis of a 1200 base-pair region of HIV-1 using methods of the present invention.

Example 2 describes methods for base-specific cleavage by modifying the nucleic acid template to be cleaved.

Example 3 illustrates the diagnostic sequencing of the RNase-T 1 coding region according to the methods of the present invention.

Example 4 illustrates the analysis of a 1000 base-pair nucleic acid.

Example 5 illustrates the use of the present invention for genotyping, including multiplex genotyping.

Example 6 illustrates the use of the present invention for transcription profiling.

Example 7 illustrates the use of the present invention for whole genome resequencing.

EXAMPLE 1

Modeling the Diagnostic Sequence Analysis of a 1200 Base-pair Region of HIV-1

The methods of the present invention have been utilized on a 1200 base-pair sequence derived from human immunodeficiency virus type 1 (HIV-1; HXB2 isolate; Genbank accession number K03455; position 2161 to 3360). This sequence was used as a model in computer simulations to examine the overall performance of the method, as well as the occurrence of ambiguities. The selected region encompasses the entire protease gene and the first ~270 codons of reverse transcriptase [compare with Hertogs K. et al., *Antimicrob. Agents Chemother.* 42: 269–276 (1998)]. The genotyping/re-sequencing of this domain of clinical isolates of HIV is of special interest in order to monitor the emergence of drug resistance-associated mutations. Single as well as multiple changes have been implicated in the decreased sensitivity towards the antiviral activity of protease and RT inhibitors [Hertogs K. et al., *Antimicrob. Agents Chemother.* 42: 269–276 (1998); Schinazi R. et al., *Int. Antivir. News* 4: 95–107 (1996) and references cited therein].

The principal objective of the computer simulation was to examine the performance of the re-sequencing method for detecting and mapping SNPs. To this end we have performed computational simulation analyses in which we have systematically mutated each nucleotide one by one in the 1200 base-pair sequence. For each mutation we have calculated the molecular masses of the cleavage products that would be generated from a given segment of the sequence in the different four RNase digestion reactions, namely upon RNase-T1 and RNase-U2 cleavage of the (+) and (−) strands. The comparison of these masses with those of the reference cleavage products from the original sequence identifies the masses of the diagnostic fragments associated with each mutational change, i.e., fragments that either appear or disappear as a result of the mutation. The underlying assumption in this analysis was that in order to be measurable, the fragment must have a molecular mass different from those of the other cleavage products generated in the same reaction. Furthermore, we have assumed that the resolution of the mass spec analysis is limited to mass differences larger than either 5 Da or 0.1%. In other words fragments whose mass difference with other fragments in the same digest is smaller than 5 Da or 0.1% were not scored in the analysis. The quantitative aspects of a mass spectrum (i.e. peak heights) were not considered in the present simulation study. For each mutational change we have computed the number of fragments that are diagnostic for the presence of the mutation. Mutational changes were scored as detectable when there was at least one diagnostic fragment (showing a spectral change). In addition, we have examined whether the mutational changes can also be mapped unambiguously. To this end we have compared the sets of diagnostic fragments associated with each mutation. Mutations that yield unique sets of fragments can be mapped unambiguously, while mutations that give the same sets cannot be distinguished from one another.

Figure 2:
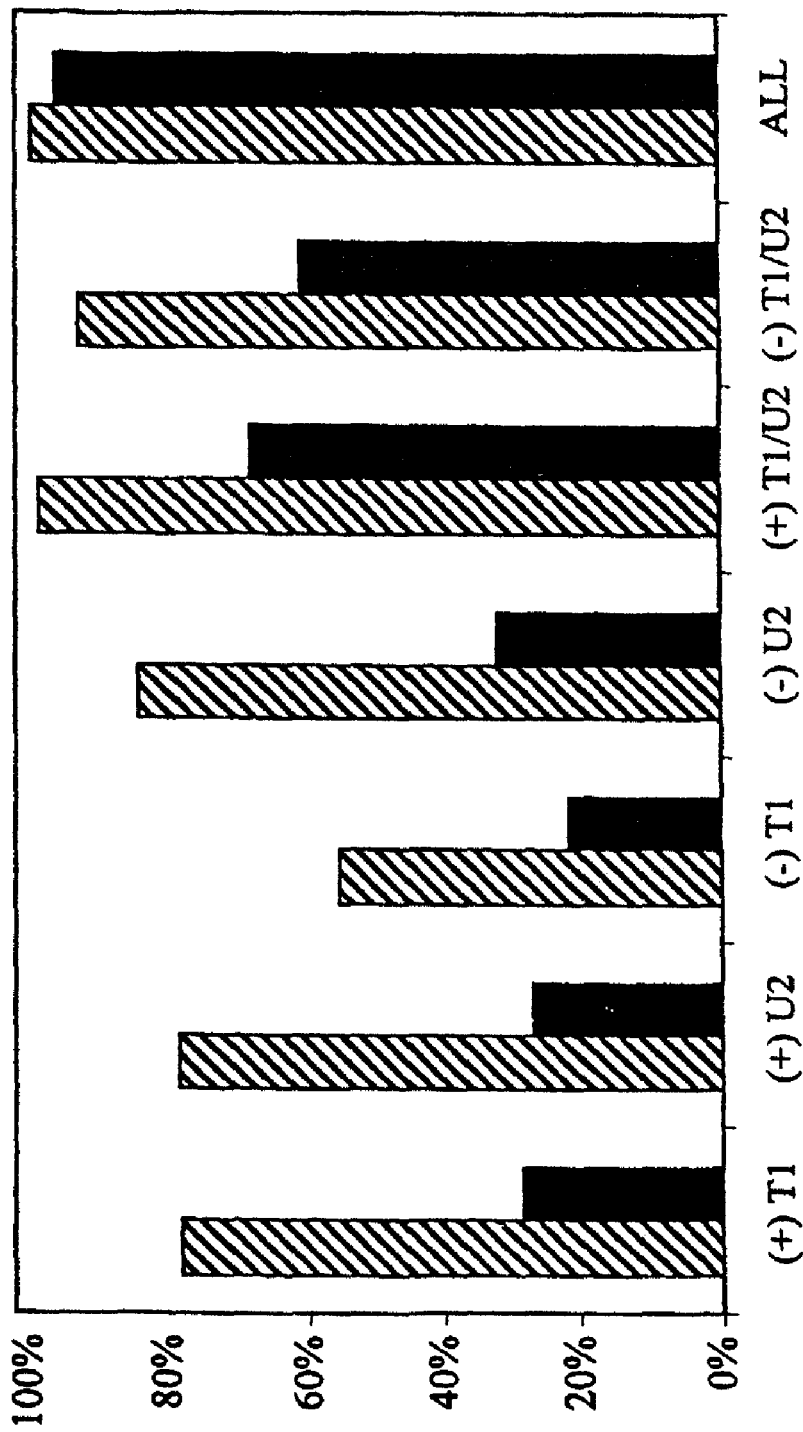
FIG. 2 summarizes the results of the mutational simulation analysis of a 200-base-pair segment of the HIV protease gene and shows the percentages of the mutational changes that can be detected (hatched bars) and mapped (filled bars). The results were computed for single RNase digests of the (+) and (−) strands with respectively RNase-T1 (T1) and RNase-U2 (U2), separately or combined (T1/U2). All refers to the analysis with the four different reactions.

In a first simulation analysis we have computed the fraction of SNPs that may be detected and mapped using respectively 1, 2 and 4 RNase digestion reactions. To this end we have performed a systematic single nucleotide substitution simulation on a 200-base-pair segment of the HIV sequence. For each of the four different RNase digestion reactions [RNase-T1 and RNase-U2 cleavage of the (+) and (−) strands] we have calculated the number of detectable diagnostic fragments and have analyzed whether these fragments are unique for each mutation. The results summarized in FIG. 2 show that in each of the single RNase digest reactions a large fraction (55% to 85%) of the mutations are detected. In contrast, only a small fraction (20% to 30%) of these mutational variations can be mapped unambiguously. The principal reason is that many different mutational changes result in the same mass differences. The fraction of mutations that can be mapped increases to around 60% to 70% when the data of two RNase digest reactions are combined. The further combination of the data from the four different cleavage reactions allows 96% of the mutational changes to be positioned unambiguously and illustrates the advantages of the methods of the present invention. Close inspection of the sequence ambiguities reveals that about half of these involve C to U (or conversely A to G) transitions. Because the difference in molecular mass between C and U residues is only 1 Da, the mass difference in the cleavage products of the strand carrying the pyrimidine base is too small to be detectable. Consequently one might expect that these mutational changes may become detectable when using $m^5U$ instead of U. Computational simulations using $m^5U$ on the same 200 base-pair sequence shows that the fraction of mutations that can be mapped unambiguously increases to 98%. Consequently all further simulations are based on the use of the analog $m^5U$. These results demonstrate that the four mononucleotide-specific RNase digests are both necessary and sufficient for re-sequencing of most sequences with a high degree of accuracy.

Figure 3:
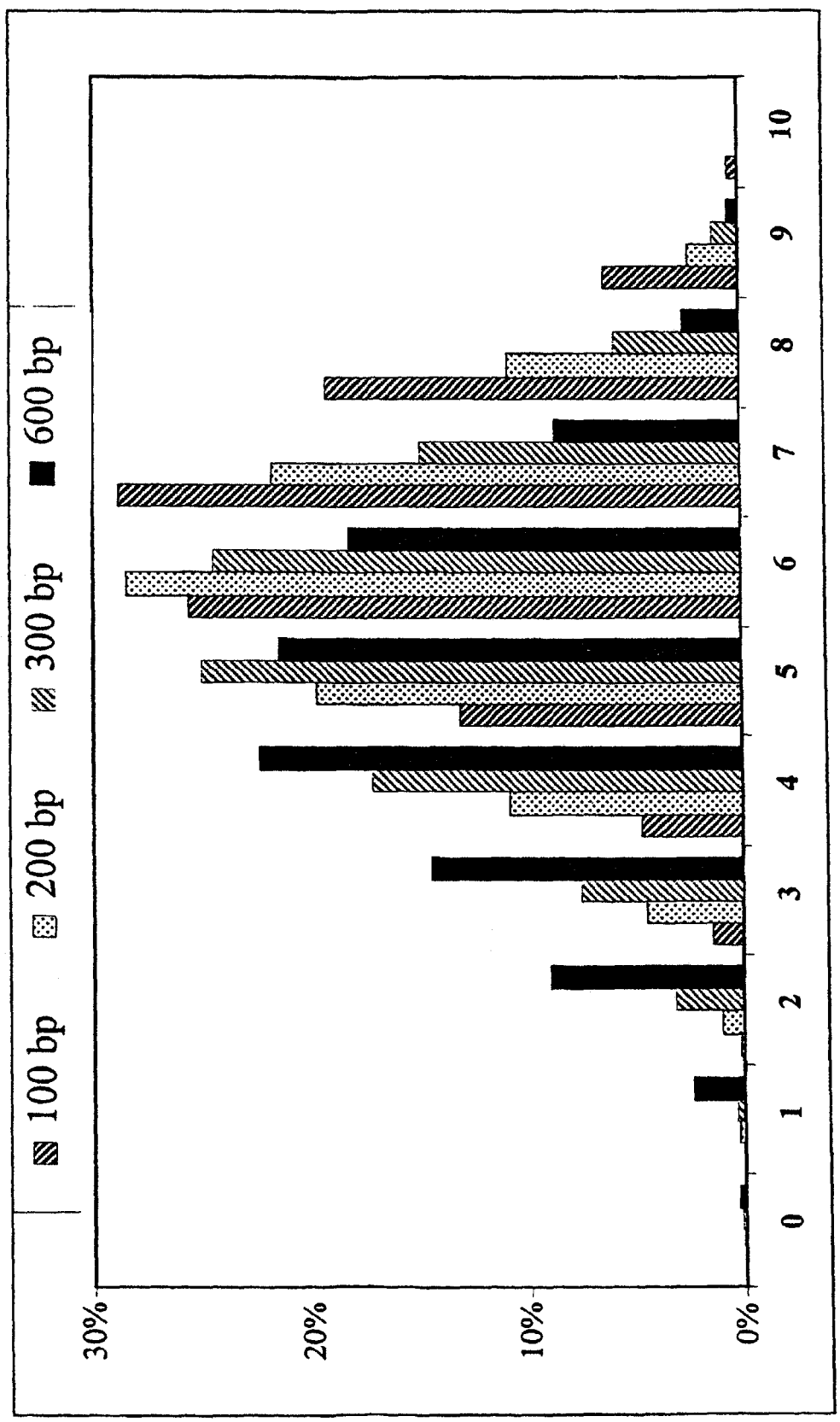
FIG. 3 shows the distributions of the number of diagnostic fragments obtained for the mutational simulation analysis of 1.200 base-pair sequence of HIV when using different length segments of respectively 100, 200, 300, and 600 base-pairs.

It will be obvious that the quality of the sequences obtained with the methods of the invention will be strongly influenced by the size of the sequence segments that are examined. Indeed, the larger the size of the segment, the larger the statistical chance that certain relevant diagnostic fragments may coincide with other cleavage products generated in the same reaction. We have therefore performed a systematic single nucleotide substitution simulation analysis on the 1,200 base-pair HIV sequence using different size segments, namely 100, 200, 300 and 600 base-pairs. In each simulation a total of 3,600 single mutational substitutions was analyzed. For each of the four different RNase digest reactions both the number and the patterns of the measurable diagnostic fragments were computed using the detection limits described above. FIG. 3 shows the distribution of the number of diagnostic fragments obtained with the 3,600 mutational changes in the four different analyses. The results clearly indicate that a larger percentage of the single nucleotide substitutions is associated with fewer diagnostic spectral changes when using larger segments of DNA.

In each simulation we determined both the number of detectable SNPs as well as the fraction of SNPs that can be mapped unambiguously. The results of the computational simulations summarized in FIG. 4 show that almost all the mutational changes are detected in the four different analyses. Of the 3,600 SNPs, the number that escaped detection were respectively 0, 1, 3 and 9 using 100 base-pair, 200 base-pair, 300 base-pair and 600 base-pair segments, respectively. In contrast, the fraction of mutational variations that can be mapped unambiguously decreases much more when using longer segments. While only 1% of the SNPs are ambiguous when analyzing 100 base-pair segments, that fraction increases to almost 10% with 600 base-pair segments. Close inspection of the ambiguities shows that the majority of these involve nearby (often adjacent) pairs of identical bases where the analysis can determine the nature of the mutation but fails to identify which of the bases is changed.

In conclusion, the results of the simulations show that the methods of the invention are effective for re-sequencing and that even large segments may be used when only a limited number of positions need to be analyzed. Also, it appears that in most cases a computer-aided simulation study will be essential in the experimental design as well as the data interpretation when using the methods of the present invention. Most importantly, the simulations will indicate whether spectral changes are unambiguously linked to particular sequence variations.

EXAMPLE 2

Base-Specific Cleavage by Modification of the Template

The present example illustrates that the specificity of cleavage by a nucleolytic reagent may be further confined through the modification of the target template such that particular phosphodiester bonds resist cleavage. More particularly, it is demonstrated that RNase-A, which normally cleaves at the 3'-side of both C- and U-residues, becomes mononucleotide-specific when the target incorporates the 2'-deoxy analog of one of these nucleotides. A region of the plasmid vector pGEM3-Zf(+) (Promega, Madison, Wis.), encompassing the multi-cloning site as well as the phage T7 promoter sequences, was used as a model (see FIG. 5).

The first step towards the sequence analysis according to the present invention involved the amplification of the 158 base-pair test sequence. The reaction was carried out in a total volume of 50 µl using 12.5 pmol each of the forward and reverse primer, 200 µM of each dNTP, 0.25 µl Taq DNA polymerase (5U/µl; Promega, Madison, Wis.), 1.5 mM $MgCl_2$ and a buffer supplied with the enzyme. After an initial incubation at 94° C. for 2 min, 40 cycles of the following temperature program were performed 94° C. for 30 sec, 50° C. for 30 sec, and 72° C. for sec. The sample was kept an additional 15 min at 72° C. and then chilled. The PCR reaction product was purified (High Pure PCR Product Purification Kit; Roche Diagnostics Belgium, Brussels, Belgium) and subsequently used for transcription of one specific strand. A mutant T7 RNA polymerase (T7 R&DNA™ polymerase; Epicentre, Madison, Wis.) with the ability to incorporate both dNTPs and rNTPs was used in the transcription reactions. In addition to a transcription with the regular ribonucleotide substrates, one reaction was performed where CTP was replaced by dCTP, while in two more separate transcriptions either dUTP or dTTP replaced UTP. The transcription reactions were run in a 50 µl volume containing: 40 mM Tris-Ac (pH 8.0), 40 mM KAc, 8 mM spermidine, 5 mM dithiothreitol, 15 mM $MgCl_2$, 1 mM of each rNTP, 5 mM of dNTP (in these cases the appropriate NTP was excluded), 40 nM DNA template (2 pmol), and 250 units T7 R&DNA™ polymerase. Incubation was performed at 37° C. for 2 hours. After transcription, the full-length T7 in vitro transcripts (118 nucleotides) were purified by allowing them to anneal to the 5'-biotinylated form of the complementary reverse PCR primer (FIG. 5) followed by capture of the biotinylated annealing products onto streptavidin-coated magnetic beads. To this end, 50 pmol biotinylated reverse primer was added to the transcription reactions. The mixtures were first incubated 5 min at 70° C. and, subsequently, 30 min at room temperature. Then, a slight excess of Sera-Mag™ streptavidin magnetic microparticles [Seradyn Inc, Indianapolis, Ind.; resuspended in 50 µl of 2M NaCl, 20 mM Tris-HCl (pH 8.0), 2 mM EDTA] was added and the resultant mixture incubated at room temperature for 30 min with agitation. A magnetic particle collector (MPC; Dynal, Oslo, Norway) was used to collect the beads, remove the supernatant and, subsequently, to wash the beads three times with 100 µl 100 mM $(NH_4)_3$-citrate. The beads were finally resuspended in 3 µl 25 mM $(NH_4)_3$-citrate containing 0.5 µg bovine pancreas RNase-A (50U/mg; Roche Diagnostics Belgium, Brussels, Belgium) and incubated at room temperature for about 30 min to digest the transcripts to completion. 1 µl of this RNase reaction was removed and added to 5 µl matrix solution. This 1:1 acetonitrile:$H_2O$ matrix solution is saturated with 3-hydroxypicolinic acid (~100 mg/ml), and further contains 25 mM $(NH_4)_3$-citrate, (occasionally) 2 pmol/µl of an oligonucleotide serving as an internal standard, and cation-exchange beads in $(NH_4)^+$-form (Dowex 50W-X2; Sigma, Saint-Louis, Mo.) to minimize the presence of sodium and potassium adducts. After incubating the mixture at room temperature for 15 min, 1 µl was put on the sample plate and allowed to dry. Mass spectra were collected using a Reflex III mass spectrometer (Bruker Daltonik GmbH, Bremen, Germany).

Figure 6A:
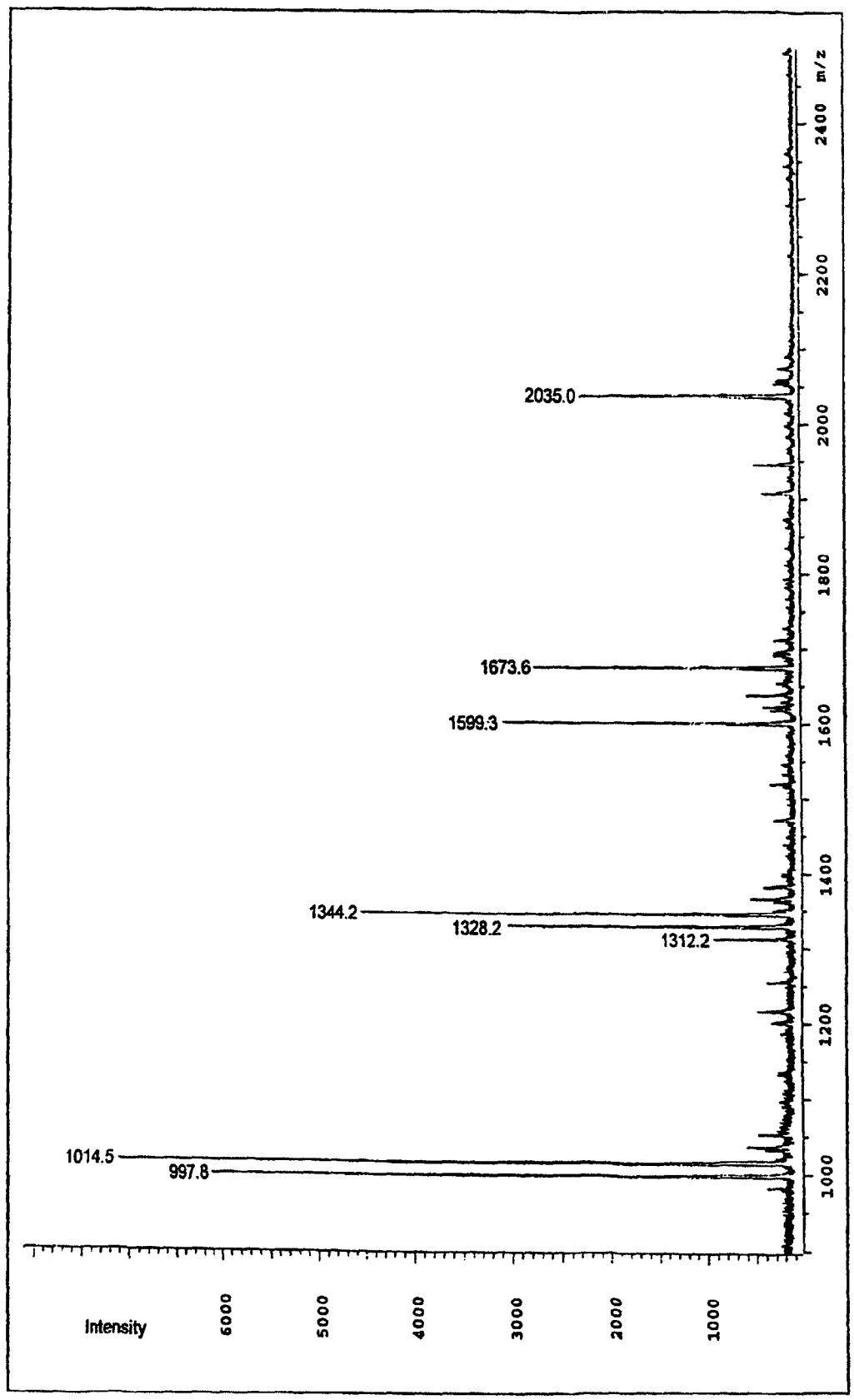
FIG. 6 is a graphical representation of the MALDI-TOF mass spectra of the RNase-A cleavage reactions of pGEM3-Zf(+) derived transcripts. The following transcripts were digested: (A) a regular transcript synthesized with rNTPs, (B) a transcript in which UMP residues are replaced by dTMP, (C) a transcript where UMP is replaced by dUMP, and (D) one that incorporates dCMP instead of CMP. Observed masses are indicated above the peaks that match with predicted digestion products (see Table II).
Figure 6B:
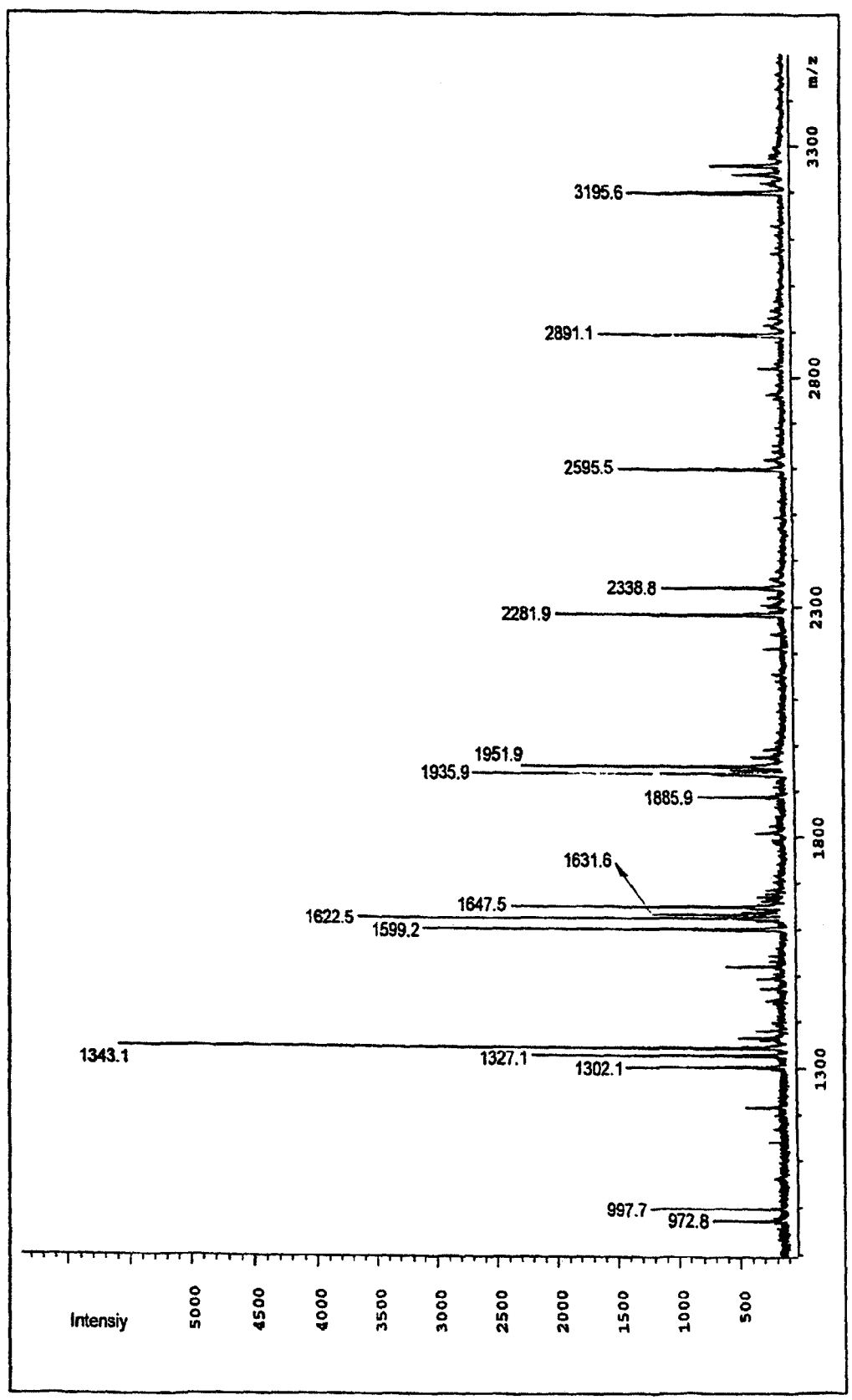
Figure 6C:
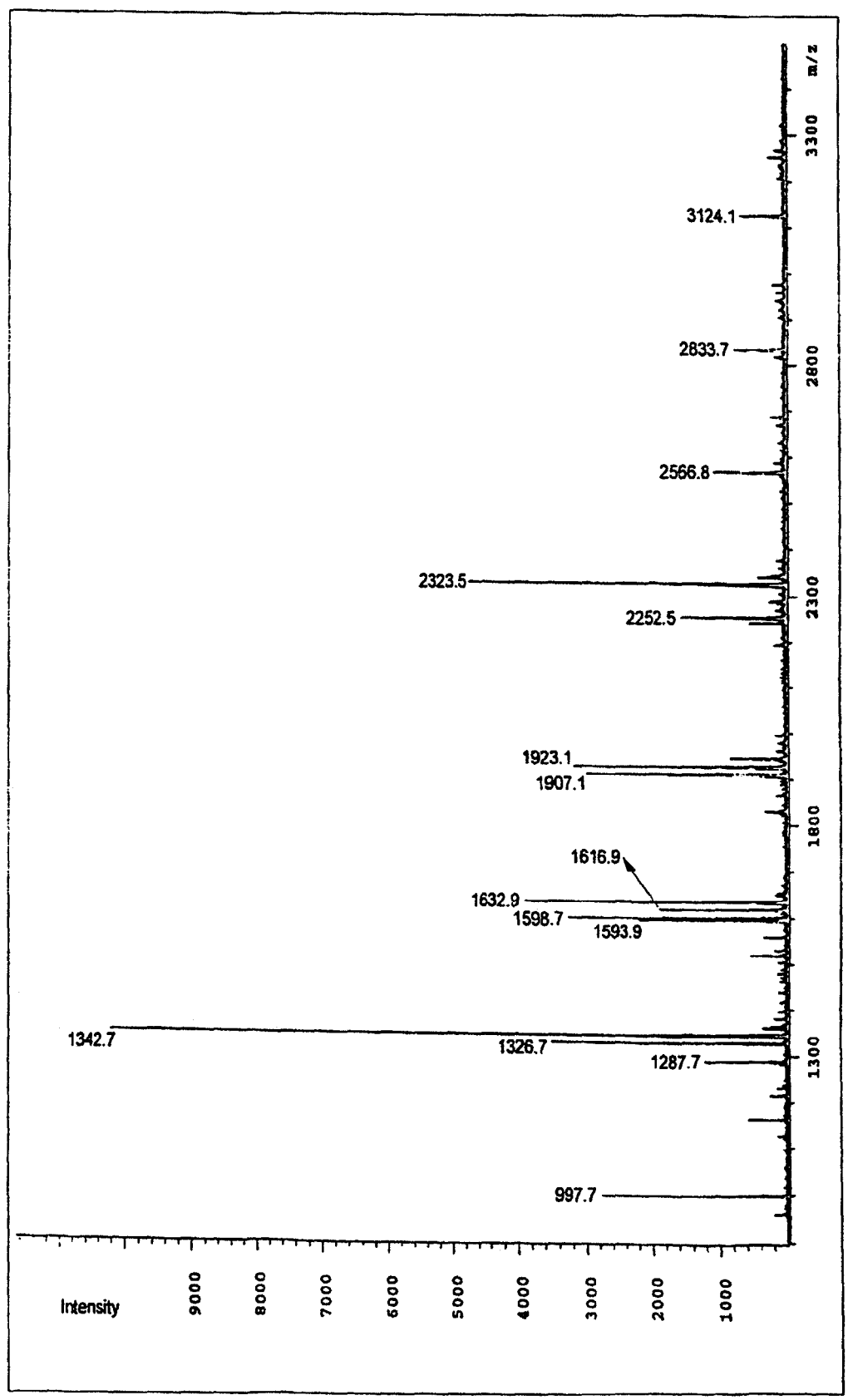
Figure 6D:
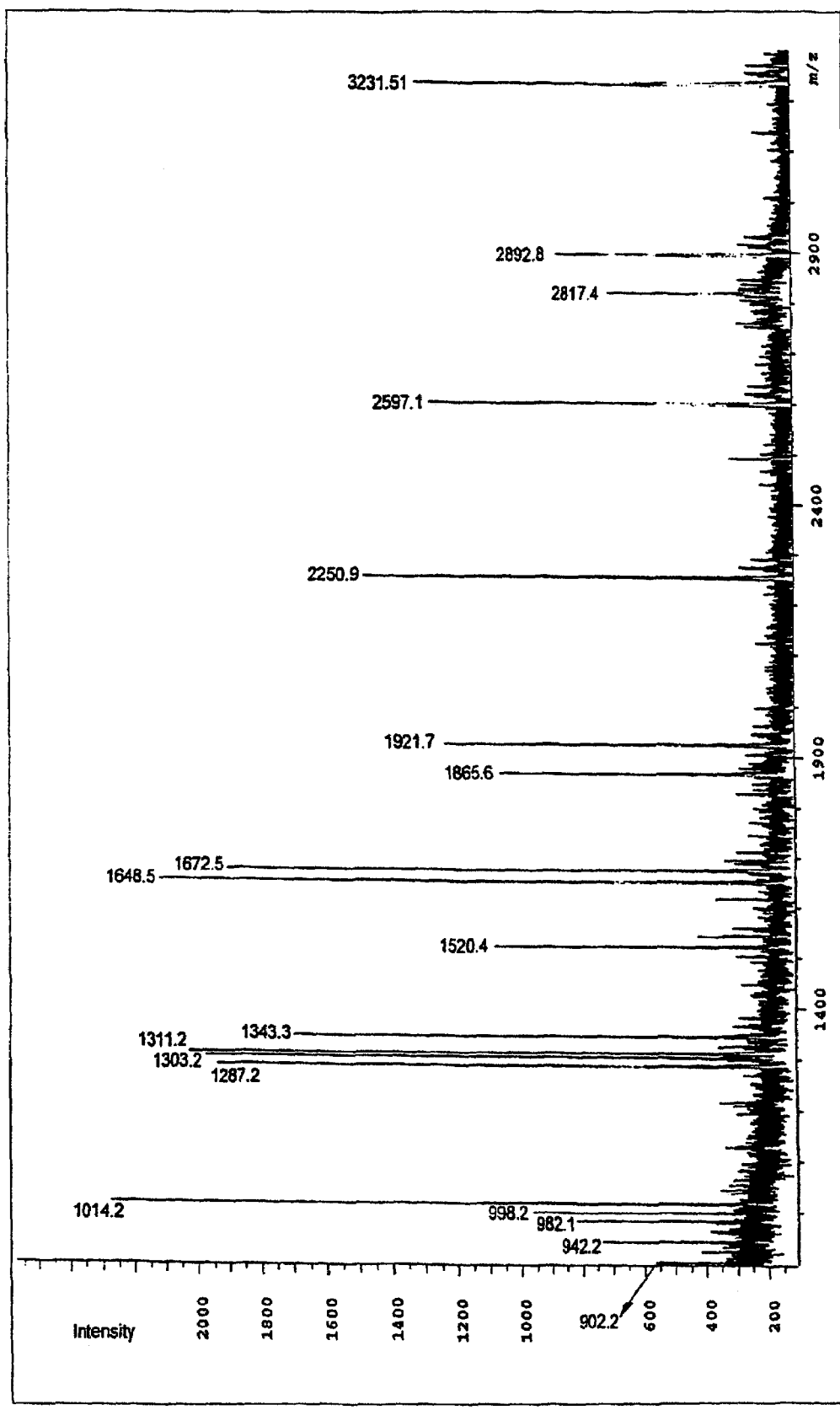

The RNase-A cleavage products predicted for each of the four transcripts are shown in Table II. Note that the mass calculation of the predicted fragments assumes a 3'-phosphate group and not the 2',3'-cyclic phosphate intermediate of the cleavage reaction. Overall, the experimentally obtained spectra (FIG. 6) are in excellent agreement with the predictions. The absence of some of the smallest 3-mers (FIGS. 6A and 6C) may be related to the mass-gate that was applied to eliminate the non-informative mono- and di-nucleotide digestion products. The predicted 3'-proximal fragment TGTTTC (1830, 1 Da) is only poorly ascertained in FIG. 6C, i.e., the spectrum deriving from the dU-transcript. This result, along with other observations, suggests that fragments with a relatively high dU-content are detected with a significantly lower sensitivity using the present MS methodology. The 2817 Da peak in FIG. 6D corresponds to the double protonated form of the added oligonucleotide. Some of the expected fragments cannot be resolved because they have an identical composition. Also, the digestion products of the regular transcript that differ by one Da only (e.g. the difference between CMP and UMP; Table II) cannot be seen as distinct peaks in FIG. 6A. In total, the data convincingly demonstrate that RNase-A behaves as a C-specific RNase when dTTP or dUTP is substituted for UTP, and as a U-specific reagent when dC rather than C is incorporated into the substrate transcripts. This high level of nucleobase specificity is achieved even under the over-digestion conditions used in the present Example.

The protocol described in the present Example is illustrative and certain modifications and variations will occur to the skilled artisan. The immobilization of the transcripts represents an easy means to prepare the material for MS analysis, e.g., removal of all other reaction components and exchange of $Na^+$ and $K^+$ counter-ions for $(NH4)^+$ (note that the subsequent RNase digestion does not require any reagents that are 'incompatible' with MS). While other methods, such as chromatography, may be used to prepare the transcripts or the derived digestion products for MS analysis, the present method is favorable in that it is readily amenable to automation and high-throughput analysis. In repeat experiments, yielding essentially the same results as described herein, the transcripts were digested in water and ~15 nanoliter of these digests was directly applied onto a Spectrochip™ (Sequenom Inc., San Diego, Calif.) for analysis by MALDI-TOF-MS.

EXAMPLE 3

Diagnostic Sequencing of the RNase-T1 Coding Region

The present example illustrates the application of the methods of the invention to the re-sequencing of a portion of the RNase-T1 coding region. We selected the RNase-T 1 coding region because of the availability of a collection of site-directed mutants [Steyaert J., *Eur. J. Biochem.* 247: 1–11 (1997)] which had previously been sequenced using the classical dideoxy chain termination method. The wild-type and mutant sequences, used in the present example, are shown in FIG. 7.

a. Analysis of the Wild-Type RNase-T1 Sequence

The experiments were performed essentially as described in Example 2. First, the selected wild-type RNase-T1 target sequences were amplified by PCR with the following primers:

5'-CCGGATATAAACTTCACGAAGACGG (forward) (SEQ ID NO: 16)
5'-GATAGGCCATTCGTAGTAGGGAGAGC (reverse) (SEQ ID NO: 17)

The resultant amplicon was subsequently re-amplified using either a forward or a reverse primer that incorporates the T7 promoter site as a 5' non-annealing extension (see FIG. 7A):
5'-TAATACGACTCACTATAGGGCGACT-
TCACGAAGACGG (forward) (SEQ ID NO: 18)
5'-TAATACGACTCACTATAGGGCGAATTCG-
TAGTAGGGAGAGC (reverse) (SEQ ID NO: 19)

Subsequently, each of the resultant promoter-appended amplicons was used as template in two separate transcription reactions. The T7 R&DNA polymerase (Epicentre, Madison, Wis.) was used to prepare transcripts that incorporate dCMP or dUMP instead of respectively CMP and UMP (referred to as the dC- and dU-transcripts). The transcription reactions were carried out as described in Example 2, except that each rNTP was present at 2 mM and incubation was performed overnight at 37° C. The four full-length T7-transcripts were purified by annealing with a biotinylated oligonucleotide that matches with the transcript 3'-end (i.e. the biotinylated form of either the forward or the reverse PCR primer used in the first amplification step) and subsequent capture onto streptavidin microparticles. After extensive washing with $(NH_4)_3$-citrate, the transcripts were eluted. The beads were resuspended in 3 µl of water and kept at 90° C. for 2 min, immediately followed by collection of the beads with the magnet and transfer of the supernatant to a fresh tube. Then, the obtained amplified target nucleic acids were digested to completion by the addition of 1 µl of 100 mM $(NH_4)_3$-citrate containing RNase-A. Finally, the reaction products were analyzed by MALDI-TOF-MS.

Figure 8A:
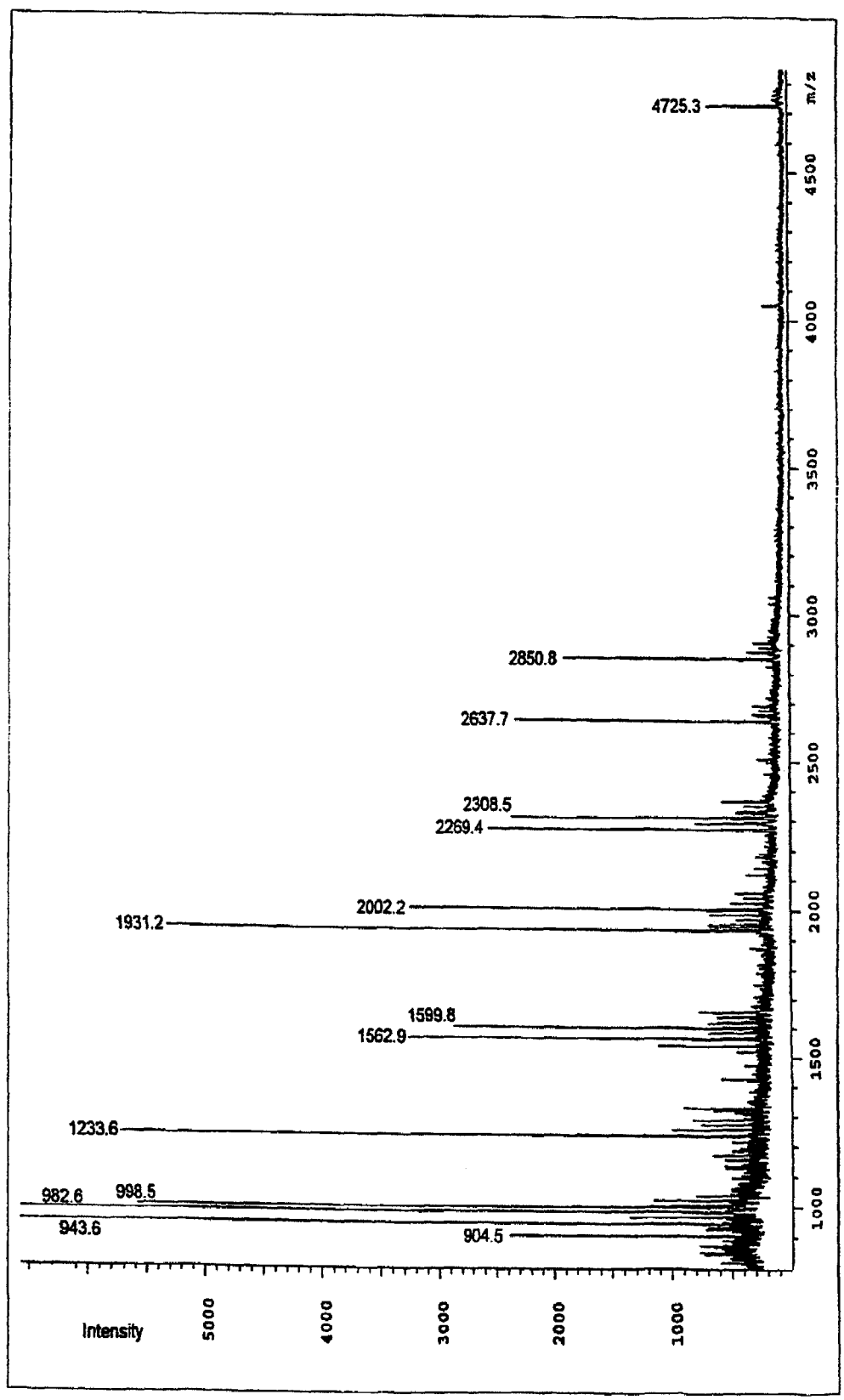
FIG. 8 is a graphical representation of the MALDI-TOF mass spectra obtained for RNase-T1 analysis. Four transcripts were digested with RNase-A: (A) dU-incorporating transcript of the (+) strand, (B) dC-transcript of the (+) strand, (C) dU-transcript of the (−) strand, (D) dC-transcript of the (−) strand. The observed masses of predicted peaks are indicated. Presumed double protonated peaks are labeled $M^{2+}$ with the mass of the parental [M+H]+peak indicated between parentheses (FIG. 8B). One of the peaks in FIG. 8D (1207.1+G) is best explained by assuming the addition of an extra G-residue at the transcript 3'-end.
FIG. 8C only shows the 900–4800 Da mass range; the digestion product of 11124 Da was not detected.
Figure 8B:
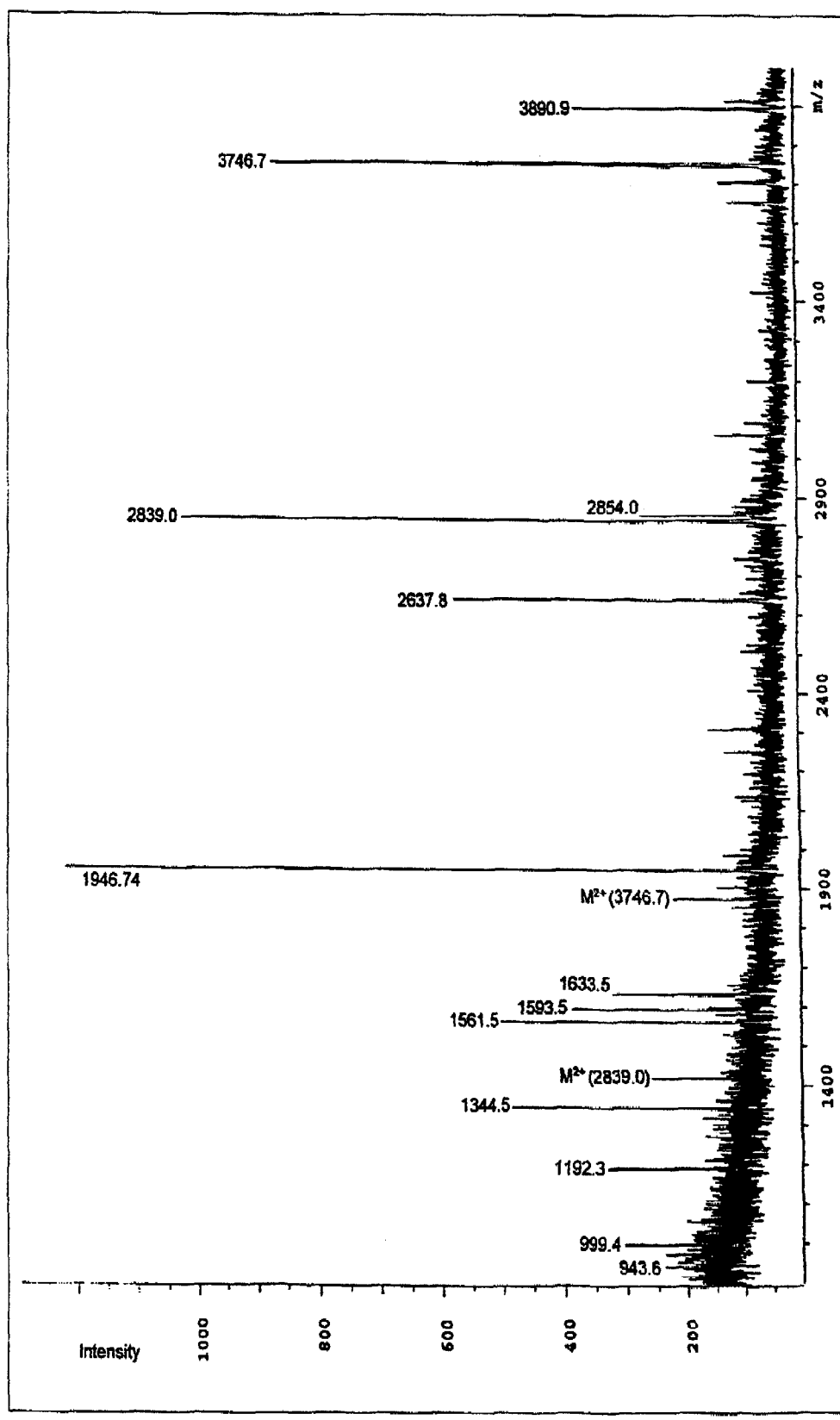
Figure 8C:
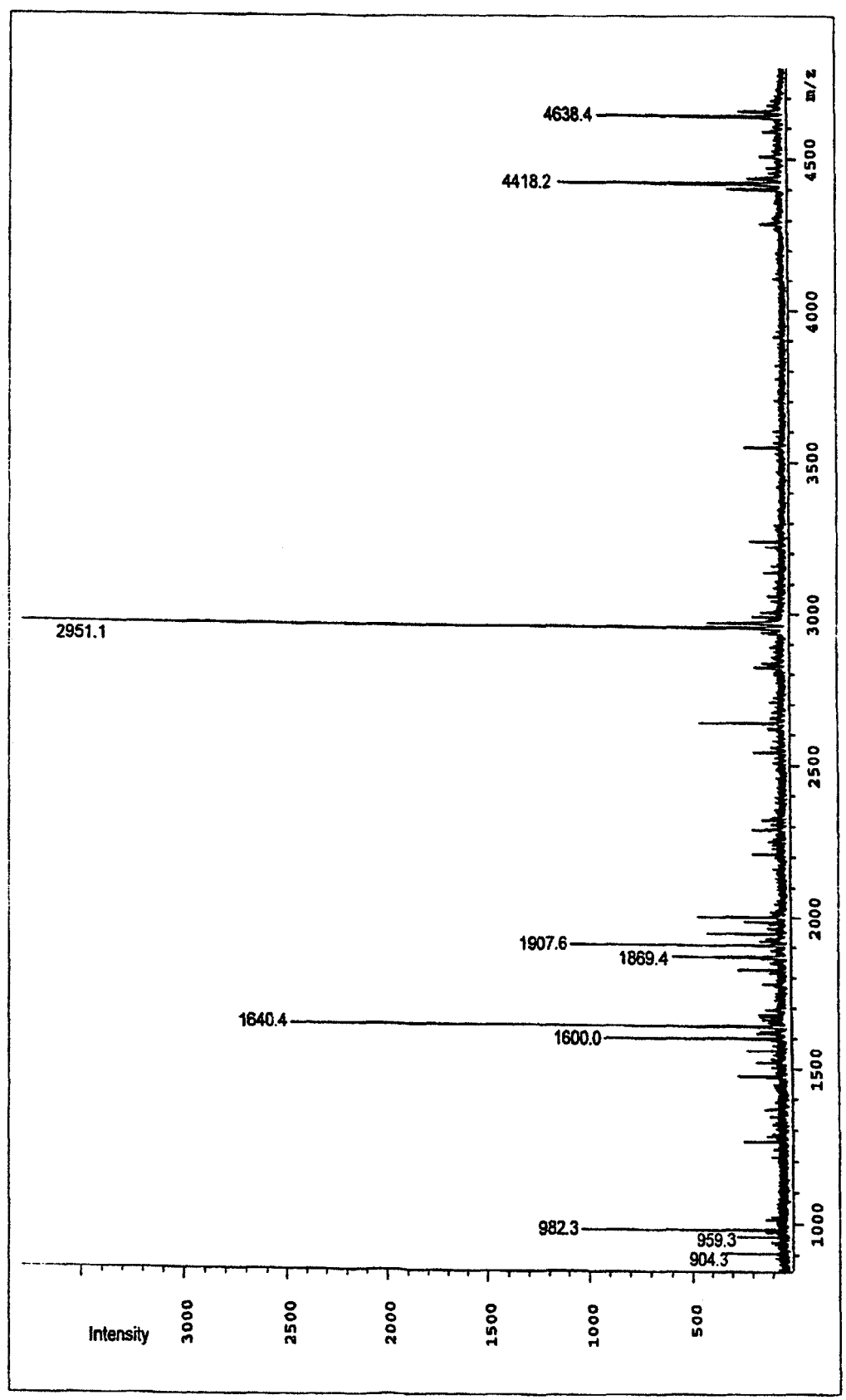
Figure 8D:
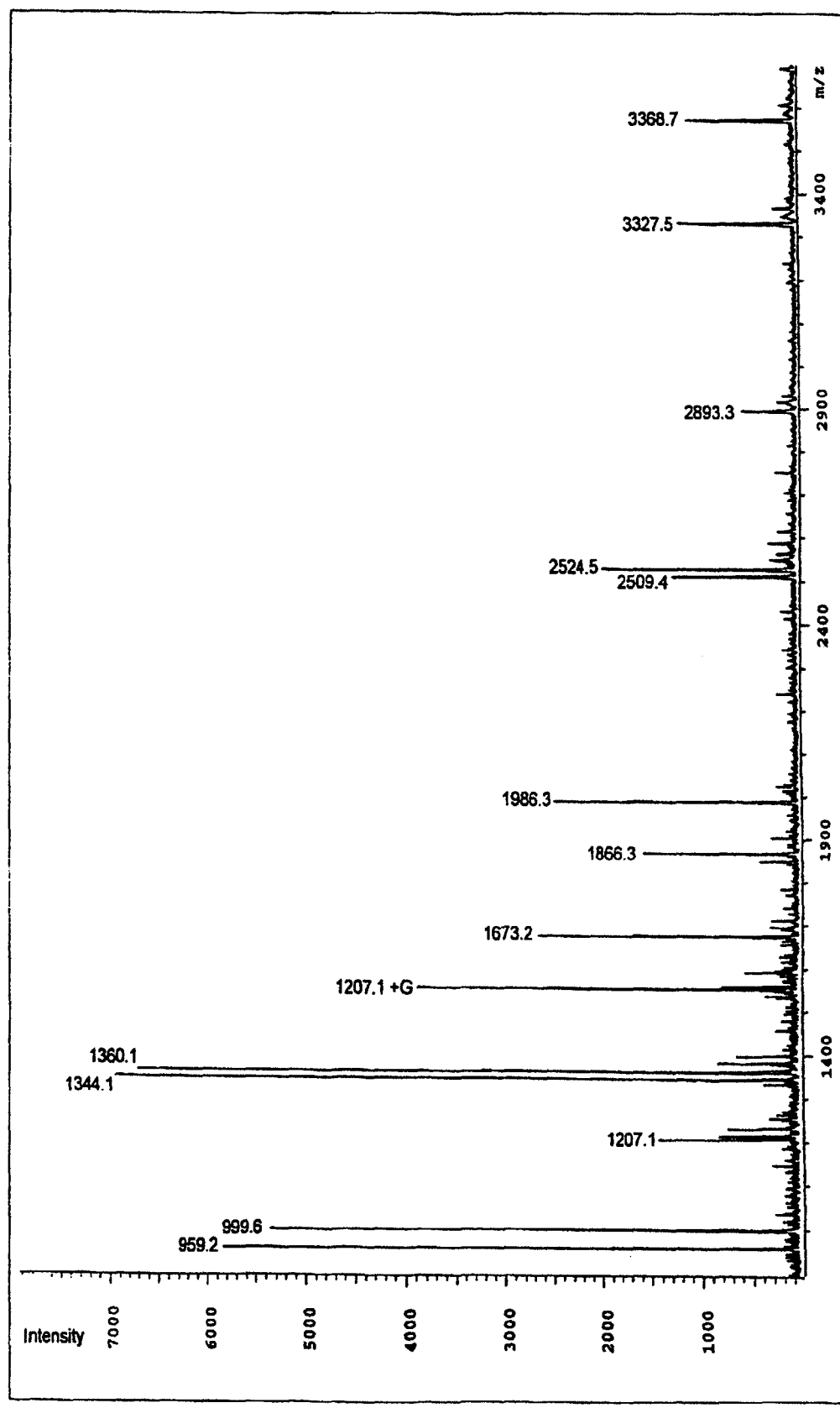

A graphical representation of the spectra is shown in FIGS. 8A–D. The predicted degradation products are listed in Table III. As with the pGEM3-Zf(+) transcripts the obtained spectra are in good agreement with the predictions. A few peaks that are most likely the result of double protonation were also observed (see FIG. 8B). The T-reaction on the (–) strand suggests the occurrence of transcripts with an extra non-template encoded nucleotide at the 3'-end [Milligan J. et al., *Nucleic Acids Res.* 15: 8783–8798 (1987)]. Indeed, in addition to the expected 3'-terminal fragment, a prominent peak is observed that coincides with the same fragment containing an extra G-residue (FIG. 8D and Table III). The absence of the expected 3'-terminal fragment from the C-reaction on the (+) strand (1153 Da; FIG. 8A) may be explained by this same phenomenon. In this case, cleavage of the 3'-extended transcript would occur and result in the 3'-phosphorylated (rather than the 3'-OH) form of the predicted fragment, a product which would coincide with another fragment of the same digestion (1233.7 Da; Table III).

b. Analysis of Selected RNase-T1 Single Point Mutations

Four single nucleotide substitutions were chosen (mutant #1, #2, #3, and #4 in FIG. 7B). Each of the mutant sequences was analyzed as described for the wild-type RNase-T1 coding region (Example 3a). The results are summarized in Table IV. Table IV shows, for each mutation, which 5 fragments of the wild-type RNase-T 1 reference sequence are affected by the mutation as well as the 5 fragments that are mutation-specific. It also shows which changes are missing, and consequently on how many, out of the ten theoretical data points, the mutation identification is actually based. Spectral changes are missing because they involve fragments that are too small (<3-mer) or not unique. Also, a few fragments were not experimentally observed, e.g., one 3-mer as well as the largest fragments with a mass of ≧9,8 Kda. Of particular interest are the results concerning mutation #2. These results indeed best illustrate the present invention. In this particular case, all four mono-nucleotide specific cleavage reactions result in the detection of a mutation, i.e. one will notice that the sequence differs from the wild-type RNase-T1 coding region. However none of these reactions, when taken alone, leads to the unambiguous mapping of the mutation. The C-reaction on the (+) strand results in a new fragment of 1947 Da. Not only the single nucleotide mutation #2 can explain the creation of such a 6-mer [composition=$A_3G(dU)C$]. For example, this is also the case for a double mutation that converts the sequence CTACTAC into CAAGTAC (see FIG. 7); the TAC peak will not be lost because of the presence of a third such 3-mer. The T-reaction on the (+) strand results in a spectrum where the mass of one fragment has increased by 56 Da when compared to the reference spectrum. This suggests the replacement of a dC by a G. Because the cleavage product contains three dC residues, it is not possible to position the substitution. The C-reaction on the (–) strand is at first sight the most informative; a large reference fragment is affected by the cleavage. The sequence of the fragment (GTAG$_1$TT—TG$_2$GATC)(SEQ ID NO: 20) is however such that both the G$_1$->C and the G$_2$->C mutation can explain the observed products of 9814 Da and 1289 Da [composition=GA(dU)C]. Finally, the T-reaction on the (−) strand is the least informative and the appearance of a peak of 944 Da [A(dC)U] can be explained in many different ways. An A(dC)U-fragment is, for example, generated by substitution of the T$_1$-residue for a C in the sequence stretch TAT$_1$TT (see FIG. 7). In conclusion, mutation #2 exemplifies that in some cases the nature and position of a sequence variation may only be determined by a combination of at least two different complementary cleavage reactions.

c. Analysis of a Mixture of Wild-Type and Mutant RNase-T1 Sequences

The analyses shown in Table IV can be used to simulate experiments where equimolar mixtures of the wild-type RNase-T1 sequence and one of the single nucleotide substitutions are examined. In such cases, which mimic heterozygotic genotypes, the spectra contain a number of novel fragments in addition to all those derived from the (wild-type) reference sequence. The characterization and location of the mutation/polymorphism is therefore necessarily based on the novel fragments only. Unambiguity requires that the novel fragments are sufficient to uniquely define the mutation. Those of skill in the art will realize that zygosity determination is straightforward using the present methods because each allele is associated with a distinct set of peaks.

We performed a number of experiments where on particular single nucleotide mutant (e.g., mutant #3; FIG. 7B) was mixed with wild-type RNase-T1 such that the mutant allele was present at the following fractions: 1:2. 1:5, 1:10, 1:20, 1:50, 1:100, 1:200, 1:500 and 1:1000. the experiment mimics the analyses of pools of samples characterized by different allele frequencies. First, equivalent quantities of the wild-type and mutant target sequences were synthesized by PCR amplification using conditions where the primers are limiting and completely consumed. After mixing the two amplicons in the desired ratios, the material was re-amplified. Then, transcripts of the (−) strand were prepared and digested as described above, except that transcriptions were performed using all four nucleotide triphosphate substrates in the ribo-form (rNTPs) and that cleavage was carried out with RNase-T1 instead of RNase-A. Each of the digestion reactions was measured 5 times. Cleavage with the RNase-T1 enzyme generates a polymorphic 15-mer fragment which reads: AAAUCAAAACCUUCG(SEQ ID NO: 21), where the underlined residue is changed to A by mutation #3 (refer to FIGS. 7A and 7B). The mass of the wild-type and the mutant fragment is 4807,91 Da and 4830,95 Da, respectively; the mutation causes a shift of 23 Da. We found that there was an excellent linear correlation between the allele frequencies and the relative peak heights ($R^2$=0,97) and that the peak associated with the mutant allele could still be identified with confidence when it represented 5–10% of the material. It should be noted that in other experiments the minimum ratio of mutant over wild-type allele that can be detected might be significantly lower. Indeed, in the present example, the reliable detection of the 'mutant peak' was somewhat encumbered by the occurrence of an extra peak as evidenced by the control spectrum recorded for the wild-type target nucleic acid. This extra peak may possibly be attributed to a low level of Na$^+$-adduct of the wild-type fragment (22 Da mass shift). In all, the latter data indicate that homologous target nucleic acids can be pooled and analyzed simultaneously; in addition to revealing certain sequence variations, the methods of the present invention may permit the allele frequencies to be estimated among the pool of biological samples. While diagnostic sequence determination as disclosed herein relies primarily on the appearances and disappearances of peaks as well as peak shifts, the present example indicates that certain quantitative aspects of a spectrum (e.g., peak height and peak area) can be included in the sequence analysis and yield complementary valuable information.

d. Analysis of RNase-T1 Multiple Mutants

The methods of the present invention are not limited to the analysis of single nucleotide substitutions. Complex variations can also be sequenced. Table IV lists the spectral changes that are predicted to be associated with a number of RNase-T1 multiple mutants, more particularly double and triple mutants (mutant #5, #6, #7, and #8 in FIG. 7B). As described above, multiple mutants are associated with a characteristic number of spectral changes. In the case of multiple substitutions, with no deletions or insertions involved, the number of affected reference fragments is always identical to the number of novel fragments. For double mutants the number of spectral changes ranges from 12, in case the mutations are adjoining (mutant #5), to a maximum of 20, in case the mutations are separated by a sequence that contains at least one A, G, C, and T. In the latter case, the double mutant is to be treated as two concurrent but independent single nucleotide substitutions. Triple mutants are associated with a minimum of 14 spectral changes (mutant #7). As with single nucleotide substitutions, not all the theoretical spectral changes can or may be observed and part of the information will be lost. In the vast majority of the cases however a systematic computational analysis, based on the obtained spectra and the reference nucleic acid sequence(s), can unambiguously identify and locate the sequence variations.

EXAMPLE 4

Mass Spectrometric Analysis of a ~1000 Base-Pair Region

The methods of the invention are designed to overcome the limitation of the short read lengths encountered with current MS-based sequencing methodologies that involve the analysis of fragment-ladders. One can envision that, depending on the application, target regions of several hundred or even a few 1000 base-pairs can be analyzed. The present example demonstrates that a large number of oligo-nucleotide fragments can be analyzed simultaneously by the methods of the present invention and that, consequently, the detection platform does not impose a limit on the methodology.

Figure 9A:
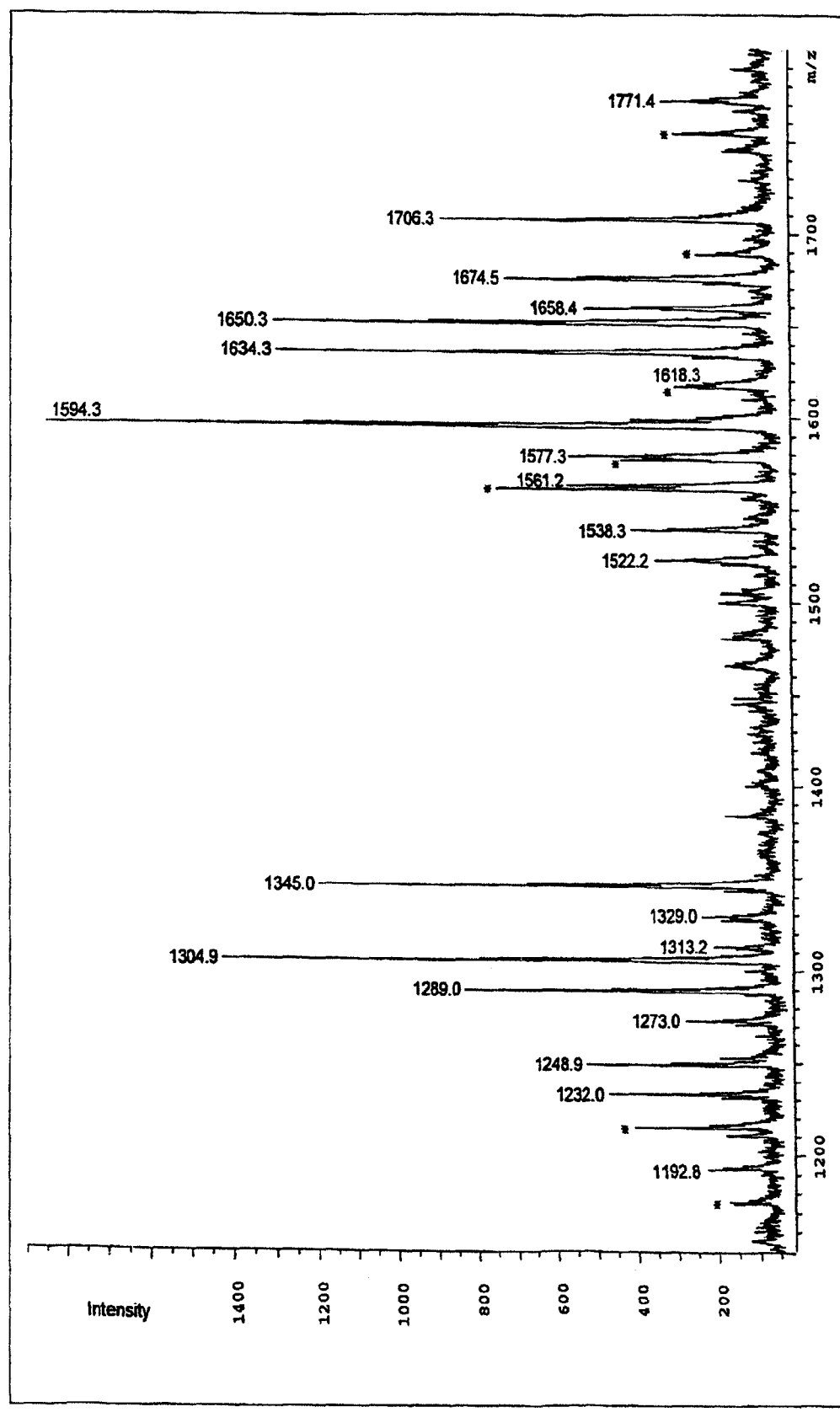
FIG. 9 (panels A, B, and C) is a graphical representation of the MALDI-TOF mass spectra of the RNase-A cleavage reaction of a pGEM3-Zf(+) derived T7-transcript of 972 nucleotides long. The transcript incorporates dCMP instead of CMP residues. The observed masses of the predicted peaks is indicated. An asterisk indicates 2',3'-cyclic phosphate reaction intermediates (see Table V).
Figure 9B:
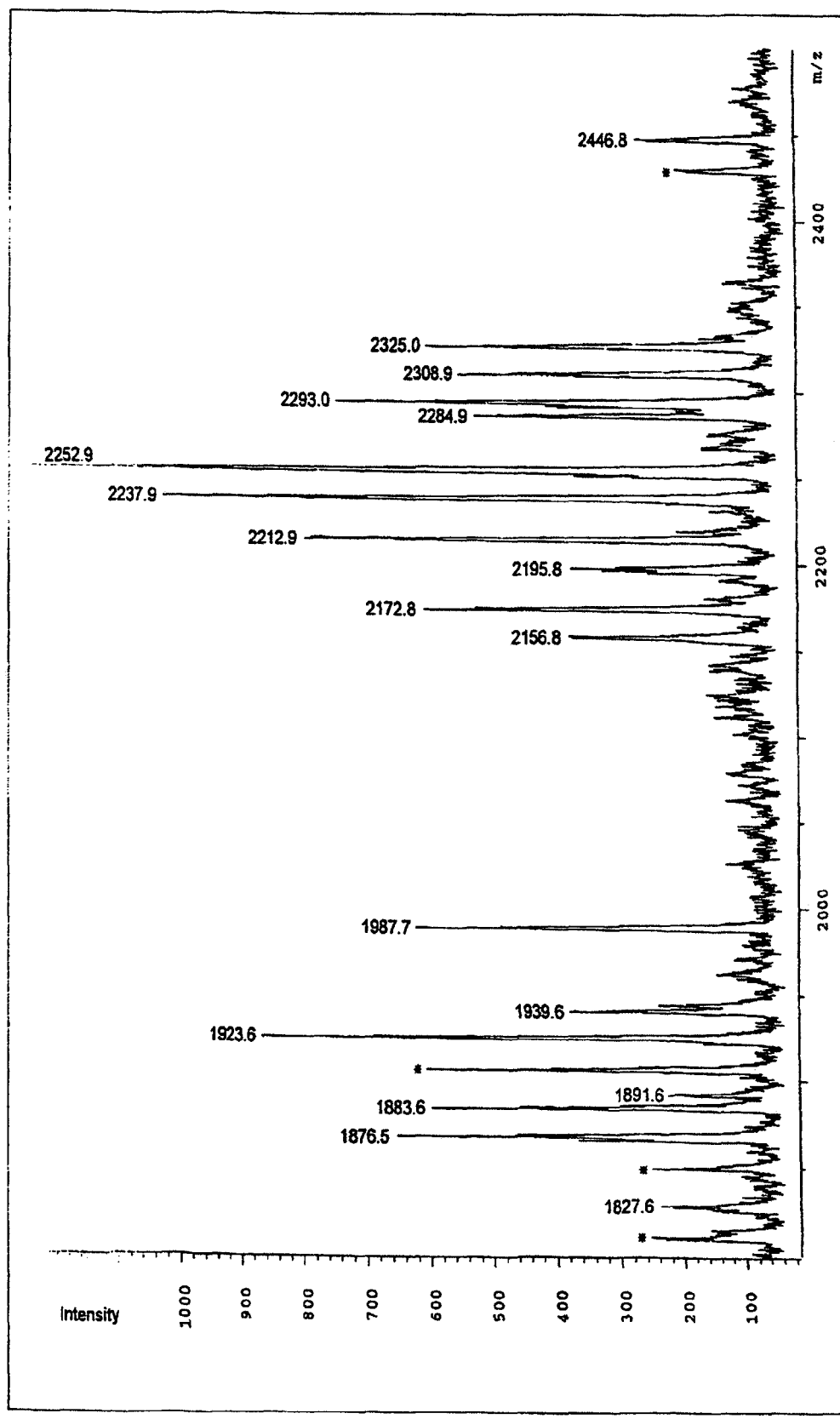
Figure 9C:
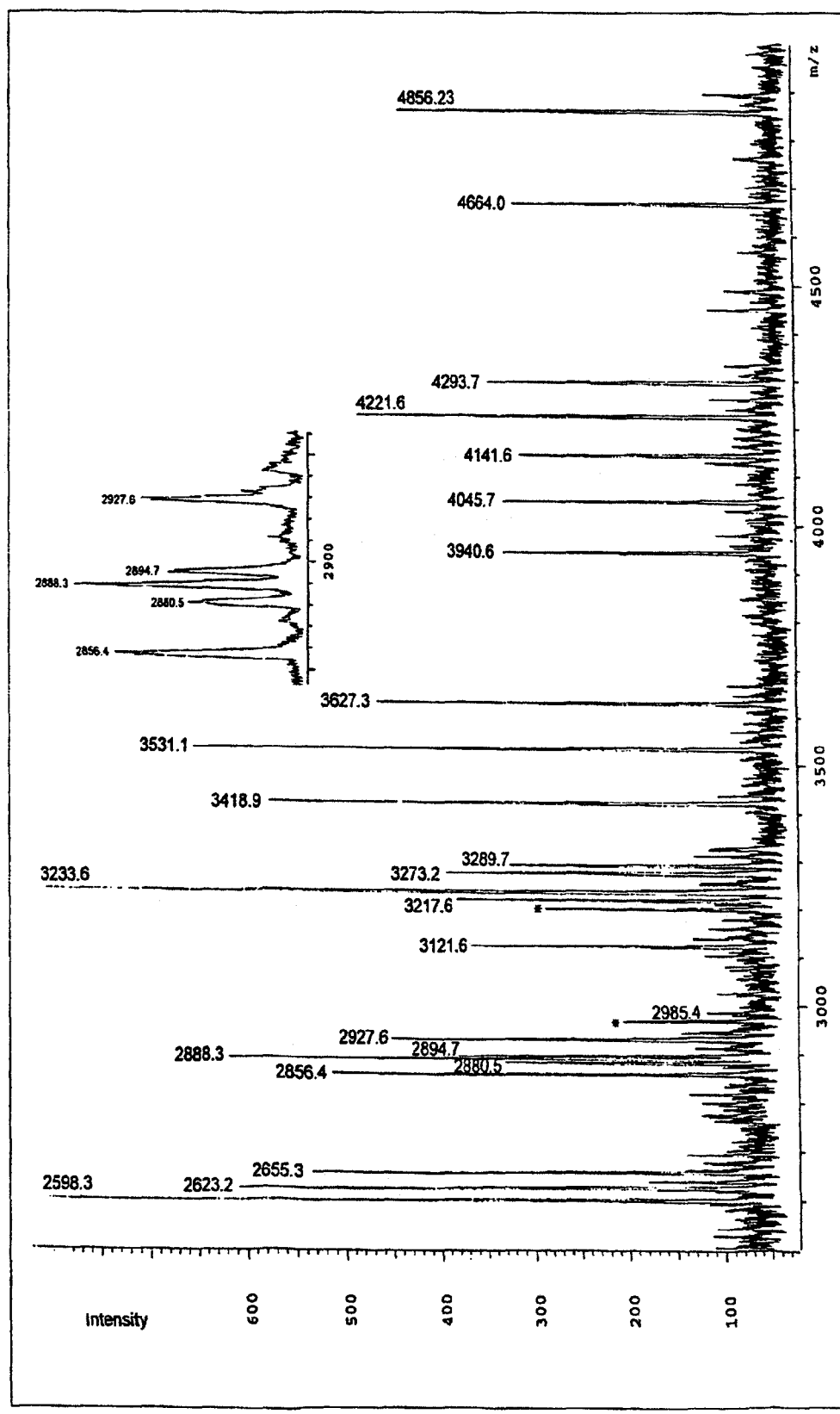

Following the scheme presented in Example 2, a 1012 base-pair region of the plasmid vector pGEM3-Zf(+) (Promega, Madison, Wis.) was amplified and the resultant amplicon, subsequently, used for preparation of a 972 nucleotides long in vitro T7 transcript (see FIG. 5). The transcript incorporated dCMP instead of CMP such that a U-specific cleavage could be performed by RNase-A. The cleavage products predicted for this transcript, are listed in Table V. FIG. 9 shows the most relevant parts of the experimentally obtained spectrum. The primary conclusion from the experimental data is that complex mono-nucleotide specific digestion reactions, consisting of >200 cleavage products, can be analyzed by mass spectrometry. The vast majority of the about 67 predicted distinct peaks are readily identified. Only a few of the 4-mer fragments are not or barely detectable. It also appears that in the present experiment the assignment of some peaks requires the assumption that (at least a portion of) certain digestion products contains a 2',3'-cyclic phosphate instead of a 3'-phosphate group. Such peaks differ from the parent peaks by −18 Da. It is well known that cyclic phosphates result from the transesterification cleavage reaction and that these intermediates get hydrolyzed in a slower second reaction step.

EXAMPLE 5

Genotyping

The methods of the present invention are also useful for the diagnostic sequencing of multiple non-contiguous regions of a sample nucleic acid. This renders the present methods useful for the genome-wide discovery as well as the routine scoring of polymorphisms (e.g. SNPs) and mutations at multiple loci in genomic DNA. Such multiplex genotyping is conceptually no different than re-sequencing; both require that alterations are characterized and positioned unequivocally. Similar to experiments involving a single target sequence described above, a computer simulation can be performed to find out which ones of the observed spectral changes is uniquely linked to particular genomic alterations. Since multiplex genotyping only requires the identification/diagnosing of a number of variant positions, it will be recognized by those of skill in the art that (i) the complexity (i.e. the combined length) of the multiple target sequences may be significantly greater than in the case of full re-sequencing, and (ii) a single specific cleavage reaction may often suffice for both allele and zygosity identification. Applications which involve the use of two sequence-specific cleavages that each positively identify one of the two alternative forms of a series of bi-allelic SNPs are also possible using the methods of the present invention. For example, many C to T transitions, the most common type of point mutations and polymorphisms in human, may be easily scored by a combination of C- and T(U)-specific reactions. It is worth mentioning that heterozygous samples analyzed using gel-electrophoretic sequencing are often difficult to identify with confidence. With the methods described herein, the detection of heterozygosity is unambiguous because of the presence of both the wild-type and the mutation specific set of mass spectral peaks.

Multiplex genotyping will generally involve the co-amplification of genomic regions. In the case of previously known SNP genetic markers, co-amplification of selected loci can be achieved by using dedicated primer pairs [Wang et al., *Science* 250: 1077–1081 (1998)]. Alternatively, a more generic approach can be adopted for both the discovery and the subsequent routine scoring of a set of SNPs where the preparation of target sequences comprises the concomitant amplification of multiple short restriction fragments derived from the sample nucleic acid. This 'random sampling' method may be particularly useful with organisms that have a high polymorphism content (e.g., more than 1 SNP in 100 base-pairs). This co-amplification can be achieved by ligating to the ends of the restriction fragments adaptor sequences that incorporate the target sites for a single PCR primer pair. In this approach, the average size of the amplicons must be small such that the majority incorporates ≧1 SNP while, additionally, the total number of the amplicons must be sufficiently small so that their combined length is amenable to analysis by the present methods. These requisites can be met by the appropriate choice of restriction enzymes and the use of methods that permit the selective amplification of discrete subsets of restriction fragments [Vos P. et al., *Nucleic Acids Res.* 23: 4407–4414 (1995); Zabeau M. and Vos P., EP 0534858 (1993); Kikuya Kato, *Nucleic Acids Res.* 23: 3685–3690 (1995)] and as described herein. For example, a first restriction enzyme that cleaves rarely in the genome under study can be combined with a second reagent that generates fragments with an average size of about 100 base-pairs (e.g., a combination of two enzymes with tetra-nucleotide recognition sites). The number of fragments edged by the two different restriction sites should preferably be less than 100,000; a suitable subset of these can readily be amplified by the use of selective primers [Vos P. et al., *Nucleic Acids Res.* 23:4407–4414 (1995)]. In addition, a PCR protocol, characterized by a highly shortened elongation time, can be used such that the amplification of short fragments is strongly favored thereby further reducing the number and the average size of the amplicons. During the selective co-amplification of genomic fragments or in a subsequent PCR step, a first primer can be used that attaches a full promoter sequence (e.g., one deriving from bacteriophage T7, T3 or SP6; supra) to the amplicons. The second strand may be synthesized by extension of a primer that contains a ribonucleotide residue at, for example, the penultimate position. Following PCR amplification, the primer sequences can be removed from this second strand by RNase digestion, and the resultant truncated strand transcribed with the aid of the first primer. This procedure minimizes the common sequences that are connected to the target restriction fragments.

EXAMPLE 6 cDNA Library Analyses—Transcription Profiling

Diagnostic sequencing will, generally, be performed on a defined nucleic acid, i.e. one will know to what reference sequence the target nucleic acid corresponds. However, the re-sequencing methods according to the present invention can also be used to identify or classify certain sequences. In such experiments, the interrogated nucleic acid (e.g. a random clone of DNA) will typically correspond to an unknown portion of a (much) larger sample sequence or represent one out of a plurality of nucleic acids present in a biological sample, or a combination of both. The mass spectra derived from the unknown nucleic acid are compared to those known or predicted for the related reference sequence(s), or portions thereof. Note that, in this type of experiments, some of the interrogated target sequences need not necessarily have their counterparts in the reference sequences, and vice versa. It will be realized that sequence identification according to the present methods may, at the same time, reveal possible sequence variations. Interrogated sequences may thus be classified as identical to one of the database sequences, as a variant of such as a reference sequence or as novel in case no matching sequence is found.

It should be recognized that analyses that involve at least the four complementary mono-nucleotide specific cleavage reactions identify unknown sequences with a resolution essentially equal to sequence determination. At the same time, the MS-based methods described herein allow fast data acquisition and are amenable to high-throughput. Therefore, the present methods are useful to identify and catalogue nucleic acids at an unprecedented scale and speed. One application consists of the analysis of cDNA libraries for the purpose of: (i) the assembly of unigene libraries (i.e. the identification/removal of replicate clones), (ii) the identification of novel genes or novel variants of previously identified genes, and (iii) transcription profiling. The speed and throughput of the present method should permit the processing of more clones and, hence, a more in depth analysis of a cDNA library.

A variety of methods are known in the art for transcription profiling, i.e. the analysis of the transcription in both qualitative and quantitative terms. In one method, the expressed-sequence-tag (EST) approach, the mRNA population is assessed by partial sequencing of randomly selected cDNA clones. Global changes in gene-expression patterns are deduced from the EST ratios among two compared cDNA libraries [Lee N. et al., *Proc. Natl. Acad. Sci. USA* 92: 8303–8307 (1995)]. The methods described herein may be used to catalogue expressed genes with a similar level of resolution but considerably higher speed and throughput. First, a library of unidirectionally cloned cDNAs is constructed in a vector that permits transcription of the inserted sequences. Preferably, the 3'-end of the cDNAs is located adjacent to the promoter. Template for transcription can be prepared by amplification of the promoter-cDNA cassette using a pair of vector-specific primers. Alternatively, vector DNA is prepared and cleaved at a restriction site within the vector close to the 5'-end of the inserted cDNA (e.g. ~25 base-pairs). Preferably, the restriction site at which the templates are cleaved should have a low occurrence frequency within the cDNAs under study. Run-off transcripts, synthesized from PCR product or digested vector, are characterized by a common 3'-end, consisting of vector sequences, which allows the isolation of full-length transcripts as described in Example 2. An alternative strategy involves treatment of the vector DNAs with a restriction reagent such that not only all templates are digested at the cDNA 5'-end but that a vast majority is also cleaved within the cDNA at some distance from the 3'-end (e.g. a few hundred base-pairs). The restriction reagent may be a single enzyme or a combination of two or more restriction enzymes. Ligation of an adaptor to the digestion product(s) [see Vos P. et al., *Nucleic Acids Res.* 23: 4407–4414 (1995)] can be considered so as to obtain full-length transcripts with a common 3'-end enabling their isolation as described in Example 2. However, transcripts that incorporate a biotin group at the 5'-end may also be prepared [Hahner S. et al., *Nucleic Acids Res.*, 25: 1957–1964 (1997)], providing an alternative means for their immobilization. Digestion within the cDNAs is an attractive option in that different partial cDNAs deriving from the same transcript are made congruent by this procedure and thereby facile to identify. The full-length run-off transcripts are finally subjected to complementary sequence-specific cleavage reactions, and the resultant digestion products analyzed by MS as disclosed herein.

Those of skill in the art will recognize the advantages of the transcript profiling method outlined above. Comparable to the EST approach, cDNAs are identified at the sequence-level, i.e. the ultimate level of resolution. Thus, while the method involves fragmentation of the interrogated nucleic acid, its level of resolution far exceeds that attained by fingerprinting techniques [Prashar Y. and Weissman S., *Proc. Natl. Acad. Sci. USA* 93: 659–663 (1996); Bachem C. et al., *The Plant Journal* 9: 745–753 (1996); Ivanova N. and Belyavsky A., *Nucleic Acids Res.* 23: 2954–2958 (1995); Liang P. and Pardee A., *Science* 257: 967–971 (1992)]. In contrast to hybridization-based approaches [Schena M. et al., *Science* 270: 467–470 (1995); Wodicka L. et al., *Nature Biotechnology* 15: 1359–1367 (1997)] the method can identify both known and previously unknown sequences. Also, it should prove faster then methods requiring gel-electrophoretic fractionation.

EXAMPLE 7

Whole-Genome Re-Sequencing

In the past couple of years the technology for sequencing entire genomes, especially those of microorganisms, has come to maturity. More than 50 microbial genomes are scheduled to be completed by the year 2000, and the benefits emerging from this vast body of knowledge are rapidly becoming clear [Clayton R. et al., *Curr. Opinion Microbiol.* 1: 562–566 (1998)]. It seems clear that sequencing entire microbial genomes is becoming routine and that microbial genetics is entering the era of 'comparative genomics'. Knowledge of the complete genome sequence is the ultimate tool in phylogenetic analyses, allows gene/functional diversity studies, and fundamentally changes the manner in which research is conducted in an organism. At the present time, a substantial portion of each new genome sequence has no database match. One may expect to see a greater proportion of orthologous genes in the future, when the microbial species diversity is better represented. At that point, when most of the sequences generated will be similar to already known sequences, global genome analyses could be performed rapidly, accurately, and cost-effectively using a re-sequencing strategy as described herein rather than by de novo sequencing methods. Similar evolutions may be anticipated outside the bacterial genetics field where genome projects for many (model) organisms are ongoing or have already been finished (e.g., *Drosophila melanogaster, Caenorhabditis elegans*, human, mouse, *Arabidopsis thaliana*, and rice).

The methods of the present invention may be readily adapted to the re-sequencing of entire (bacterial) genomes or megabase nucleic acid regions. This may be accomplished with the use of a shotgun approach that involves the sequence analysis of unselected subclones that harbor random fragments according to the methods of the present invention. The assembly of all the independent, random sequences is fundamentally different from that in a de novo sequencing project [Fleischmann R et al., *Science* 269: 496–512 (1995)] because of the availability of a reference sequence that serves as a scaffold. The assembly into a single complete sequence comes down to matching each set of experimentally obtained spectra with a portion of the reference sequence. The computational approaches required to accomplish this are similar to those that are needed for the analysis of cDNA libraries, outlined in Example 6. In both cases one does not know in advance the reference sequence, if at all existing, for a given interrogated target region. It should be noted, however, that the present shotgun approach might be even more demanding in terms of computational power because of the undefined ends of the segments. At the same time, the algorithms must be capable of mapping the variations that occur between the target and the reference sequence. It is expected that a shotgun approach with its built-in redundancy (i.e., most sequences will be covered several-fold) should prove useful for the comprehensive comparison of a pair of related genomes. An alternative for the shotgun approach strategy consists of the analysis of clones from one or more libraries of restriction enzyme fragments or the analysis of defined amplicons generated with locus specific primer pairs.

While the present invention has been described in terms of the preferred embodiments, it is understood that variations and modifications will occur to those skilled in the art. Therefore, it is intended that the appended claims cover all such equivalent variations which come within the scope of the invention as claimed. All of the references cited herein are expressly incorporated by reference.

TABLE I

Detection of the twelve possible point mutations that can occur in DNA by the methods of the present invention. Each substitution is associated with the loss (− sign) and gain (+ sign) of a cleavage site. In addition, each mutation affects the mass of two digestion products as indicated. Mass differences shown in bold face result from the incorporation of $m^5U$ in both transcripts (see text for details).

| Mutation | | RNase T1 | | RNase U2 | |
|---|---|---|---|---|---|
| (+) strand | (−) strand | (+) transcript | (−) transcript | (+) transcript | (−) transcript |
| transitions | | | | | |
| A->G | T->C | + | −1 Da −15 Da | − | −1 Da −15 Da |
| G->A | C->T | − | +1 Da +15 Da | + | +1 Da +15 Da |
| T->C | A->G | −1 Da −15 Da | + | −1 Da −15 Da | − |
| C->T | G->A | +1 Da +15 Da | − | +1 Da +15 Da | + |
| transversions | | | | | |
| A->C | T->G | −24 Da | + | − | +39 Da +25 Da |
| C->A | G->T | +24 Da | − | + | −39 Da −25 Da |
| T->G | A->C | + | −24 Da | +39 Da +25 Da | − |
| G->T | C->A | − | +24 Da | −39 Da −25 Da | + |
| T->A | A->T | +23 Da +9 Da | −23 Da −9 Da | + | − |
| A->T | T->A | −23 Da −9 Da | +23 Da +9 Da | − | + |
| C->G | G->C | + | − | +40 Da | −40 Da |
| G->C | C->G | − | + | −40 Da | +40 Da |

TABLE II

RNAse-A digestion products predicted for four different pGEM3-Zf(+) derived transcripts. The ≧3-mer fragments are ranked according to their molecular masses. The regular transcript was prepared with rNTP substrates. Transcripts that incorporate dTMP, dUMP, or dCMP are denoted as dT-, dU-, or dC-transcript. Fragments containing a 5'-triphosphate (5'ppp-) are indicated.

| regular transcript | | dT-transcript | | dU-transcript | | dC-transcript | |
|---|---|---|---|---|---|---|---|
| Fragments | expected mass (M+) | fragments | expected mass (M+) | fragments | expected mass (M+) | fragments | expected mass (M+) |
| CAT | 959.6 | TGC | 973.6 | TGC | 959.6 | CCT | 903.5 |
| AAT | 983.6 | GAC | 998.6 | GAC | 998.6 | CAT | 943.6 |
| AGC | 998.6 | ATGC | 1302.8 | ATGC | 1288.8 | CAT | 943.6 |
| AGC | 998.6 | AAGC | 1327.8 | AAGC | 1327.8 | AAT | 983.6 |
| GAC | 998.6 | GAGC | 1343.8 | GAGC | 1343.8 | AGT | 999.6 |
| AGT | 999.6 | AGGC | 1343.8 | AGGC | 1343.8 | GGT | 1015.6 |
| GGC | 1014.6 | 5'ppp-GGGC | 1599.7 | TTGGC | 1594.9 | AGCT | 1288.8 |
| GGT | 1015.6 | TTGGC | 1623.0 | 5'ppp-GGGC | 1599.7 | AGCT | 1288.8 |
| GGT | 1015.6 | ATAGC | 1632.0 | ATAGC | 1618.0 | CGGT | 1304.8 |
| AAAT | 1312.8 | GGTAC | 1648.0 | GGTAC | 1634.0 | AAAT | 1312.8 |
| AAGC | 1327.8 | TGTTTC | 1886.2 | TGTTTC | 1830.1 | GAGT | 1344.8 |
| GAAT | 1328.8 | GAATTC | 1936.2 | GAATTC | 1908.1 | CACCT | 1521.9 |
| GAGC | 1343.8 | GTAATC | 1936.2 | GTAATC | 1908.1 | GGCGT | 1650.0 |
| AGGC | 1343.8 | ATGGTC | 1952.2 | ATGGTC | 1924.1 | AGAGT | 1674.0 |
| GAGT | 1344.8 | TAGAGTC | 2281.4 | TAGAGTC | 2253.4 | CGACCT | 1867.1 |
| 5'ppp-GGGC | 1599.7 | GGGGATC | 2338.4 | GGGGATC | 2324.4 | CGAGCT | 1923.2 |
| AGAGT | 1674.0 | TAAATAGC | 2594.6 | TAAATAGC | 2566.6 | GCAAGCT | 2252.4 |
| GGGGAT | 2035.2 | TATAGTGTC | 2889.8 | TATAGTGTC | 2833.7 | GCAGGCAT | 2597.6 |
| | | TTGAGTATTC (SEQ ID NO: 22) | 3194.0 | TTGAGTATTC (SEQ ID NO: 22) | 3123.9 | 5'ppp-GGGCGAAT | 2893.5 |
| | | | | | | ACCCGGGAT (SEQ ID NO: 23) | 3232.0 |

TABLE III

RNase-A digestion products predicted for the dU- and dC-transcripts of the (+) and (−) strands of the RNase-T1 coding region. Only the ≧3-mers are shown. Cleavage of the dU-transcript is C-specific. Likewise, the T-reaction is performed on the dC-transcript. Two fragments, shown in italics, assume the occurrence of 3'-extended transcripts (refer to Example 3).

| | $[M + H]^+$ |
|---|---|
| (+) strand/C-reaction | |
| TTC | 904.5 |
| TAC | 943.6 |
| TAC | 943.6 |
| TAC | 943.6 |
| AAC | 982.6 |
| AAC | 982.6 |
| GAC | 998.6 |
| TATC-OH3' | 1153.7 |
| *TATC-p3'* | *1233.7* |
| TTAC | 1233.7 |
| AATTC | 1562.9 |
| 5'ppp-GGGC | 1599.7 |
| AAATAC | 1931.2 |
| GAAGAC | 2002.2 |
| TGTGAGC | 2269.4 |
| GAATGGC | 2308.4 |
| GGTGAAAC | 2637.6 |
| TGTTGGATC | 2849.7 |
| GAAGGTTTTGATTTC (SEQ ID NO: 24) | 4723.8 |
| (+) strand/T-reaction | |
| ACT | 943.6 |
| GAT | 999.6 |
| CCCT | 1192.7 |
| GGAT | 1344.8 |
| CCAAT | 1562.0 |
| GGCCT | 1594.0 |
| GAGCT | 1634.0 |
| GAAACT | 1947.2 |
| ACGAAT | 1947.2 |
| ACGAAGGT | 2637.6 |
| ACAACAACT | 2838.8 |
| 5'ppp-GGGCGACT | 2853.5 |
| ACCCACACAAAT (SEQ ID NO: 25) | 3746.4 |
| CACGAAGACGGT (SEQ ID NO: 26) | 3890.4 |
| (−) strand/C-reaction | |
| TTC | 904.5 |
| TTC | 904.5 |
| GTC | 959.6 |
| AAC | 982.6 |
| 5'ppp-GGGC | 1599.7 |
| AAAAC | 1641.0 |
| AGTTTC | 1869.1 |
| GAATTC | 1908.1 |
| AGAGAAATC | 2950.8 |
| GTGAAGTTTATATC (SEQ ID NO: 27) | 4417.7 |
| GTAGTAGGGAGAGC (SEQ ID NO: 28) | 4637.8 |
| GTAGTTGTTGTATTTGTGTGGGTAAGAATTGGATC (SEQ ID NO: 20) | 11123.7 |
| (−) strand/T-reaction | |
| CGT | 959.6 |
| CGT | 959.6 |
| CGT | 959.6 |
| AGT | 999.6 |
| AGT | 999.6 |
| CCGG-OH3' | 1207.8 |
| *CCGGG-OH3'* | *1553.0* |
| GGAT | 1344.8 |
| GGGT | 1360.8 |
| GAAGT | 1674.0 |
| CACCGT | 1867.1 |
| AAGAAT | 1987.2 |
| CAAAACCT | 2509.6 |
| CCAACAGT | 2525.6 |
| 5'ppp-GGGCGAAT | 2893.5 |
| AGGGAGAGCT (SEQ ID NO: 29) | 3328.0 |
| CACAGAGAAAT (SEQ ID NO: 30) | 3569.2 |

TABLE IV

Spectral changes associated with single and multiple mutations in the RNase-T1 coding region.

| | | AFFECTED REFERENCE FRAGMENTS | | NOVEL FRAGM. | |
|---|---|---|---|---|---|
| REACTION | SEQUENCE | $[M + H]^+$ | Comments | $[M + H]^+$ | Comments |
| mutation #1 [A −> T on (+) strand/T −> A on (−) strand] | | | | | |
| (+)/C | TT<u>A</u>C | 1233.7 | not unique | 1194.7 | |
| (+)/T | <u>A</u>CCCACACAAAT (SEQ ID NO: 25) | 3746.4 | | 325.2 | <3-mer |
| | | | | 3417.1 | |
| (−)/C | GTAGTTGTTGTATTTGTGTGGG<u>T</u>AAGAATTGGATC (SEQ ID NO: 20) | 11123.7 | not observed | 11162.7 | not observed |
| (−)/T | GGG<u>T</u> | 1360.8 | | 3352.1 | |
| | AAGAAT | 1987.2 | | | |

TABLE IV-continued

Spectral changes associated with single and multiple mutations in the RNase-T1 coding region.

| REACTION | SEQUENCE | AFFECTED REFERENCE FRAGMENTS [M + H]+ Comments | NOVEL FRAGM. [M + H]+ Comments |
|---|---|---|---|
| | mutation #2 [C -> G on (+) strand/G -> C on (-) strand] | | |
| (+)/C | AAC | 982.6 not unique | 1,947.2 |
| | TAC | 943.6 not unique | |
| (+)/T | ACAACAACT | 2,838.8 | 2,894.8 |
| (-)/C | GTAGTTGTTGTATTTGTGTGGGTAAGAATTGGATC | 11,123.7 not observed | 1,288.8 |
| | (SEQ ID NO: 20) | | 9,813.9 not observed |
| (-)/T | AGT | 999.6 not unique | 943.6 |
| | mutation #3 [A -> T on (+) strand/T -> A on (-) strand] | | |
| (+)/C | GAAGGTTTTGATTTC | 4723.8 | 4684.8 |
| | (SEQ ID NO: 24) | | |
| (+)/T | ACGAAGGT | 2637.6 | 1618.0 |
| | | | 1015.6 |
| (-)/C | TTC | 904.5 not unique | 943.6 not observed |
| (-)/T | CAAAACCT | 2509.6 | 2838.8 |
| | T | 325.2 <3-mer | |
| | mutation #4 [A -> T on (+) strand/T -> A on (-) strand] | | |
| (+)/C | GAAGGTTTTGATTTC | 4723.8 | 4684.8 |
| | (SEQ ID NO: 24) | | |
| (+)/T | ACGAAGGT | 2637.6 | 1288.8 |
| | | | 1344.8 not unique |
| (-)/C | TTC | 904.5 not unique | 943.6 |
| (-)/T | T | 325.2 <3-mer | 1288.8 |
| | CGT | 959.6 not unique | |
| | mutation #5 [AC -> CG on (+) strand/GT -> CG on (-) strand] | | |
| (+)/C | AAC | 982.6 not unique | 653.4 <3-mer |
| | TAC | 943.6 not unique | 1,288.8 |
| (+)/T | ACAACAACT | 2,838.8 | 2,854.8 not resolved |
| (-)/C | GTAGTTGTTGTATTTGTGTGGGTAAGAATTGGATC | 11,123.7 | 1,288.8 |
| | (SEQ ID NO: 20) | | 9,868.9 |
| (-)/T | AGT | 999.6 not unique | 1,288.8 |
| | T | 325.2 <3-mer | |
| | mutation #6 [AAA -> CAG on (+) strand/TTT -> CTG on (-) strand] | | |
| (+)/C | AAATAC | 1931.2 | 324.2 <3-mer |
| | | | 1618.0 |
| (+)/T | ACCCACACAAAT | 3746.4 | 3722.3 |
| (-)/C | GTAGTTGTTGTATTTGTGTGGGTAAGAATTGGATC | 11123.7 | 4104.4 |
| | (SEQ ID NO: 20) | | 7108.3 |
| (-)/T | AT | 654.4 <3-mer | 943.6 |
| | T | 325.2 <3-mer | |
| | T | 325.2 <3-mer | 1015.6 |
| | GT | 670.4 <3-mer | |
| | mutation #7 [AAT -> GCG on (+) strand/ATT -> CGC on (-) strand] | | |
| (+)/C | AATTC | 1562.9 | 669.4 <3-mer |
| | | | 959.6 |
| (+)/T | CCAAT | 1562.0 | 1883.1 |
| | T | 325.2 <3-mer | |
| (-)/C | GTAGTTGTTGTATTTGTGTGGGTAAGAATTGGATC | 11123.7 | 8904.3 |
| | (SEQ ID NO: 20) | | 669.4 <3-mer |
| | | | 1634.0 |
| (-)/T | AAGAAT | 1987.2 | 3601.2 |
| | T | 325.2 <3-mer | |
| | GGAT | 1344.8 | |
| | mutation #8 [AAC, AAC, TAC -> AAG, AAT, TTC on (+) strand/GTA, GTT, GTT -> GAA, ATT, CTT on (-) strand] | | |
| (+)/C | AAC | 982.6 | 2856.7 |
| | AAC | 982.6 | |
| | TAC | 943.6 not unique | |
| (+)/T | ACAACAACT | 2838.8 | 2605.6 |
| | | | 325.2 <3-mer |
| | ACGAAGGT | 2637.6 | 325.2 <3-mer |
| | | | 2308.4 |

TABLE IV-continued

Spectral changes associated with single and multiple mutations in the RNase-T1 coding region.

| REACTION | SEQUENCE | AFFECTED REFERENCE FRAGMENTS [M + H]+ | Comments | NOVEL FRAGM. [M + H]+ | Comments |
|---|---|---|---|---|---|
| (−)/C | GTAGTTGTTGTATTTGTGTGGGTAAGAATTGGATC (SEQ ID NO: 20) | 11123.7 | | 2237.4 8888.3 | |
| (−)/T | CGT | 959.6 | not unique | 1947.2 | |
| | AGT | 999.6 | not unique | | |
| | GT | 670.4 | <3-mer | 614.4 | <3-mer |

TABLE V

U-specific cleavage of a 972 nucleotides long T7 transcript. The predicted digestion products, 222 in total, are grouped according to their composition. An asterisk indicates those peaks for which a companion cyclic phosphate reaction intermediate is observed (FIG. 9). The largest fragment is absent from the obtained spectrum; a few other cleavage products appear as minor peaks and are labeled 'weak'.

| Composition | M + H | Length | Number | Remarks |
|---|---|---|---|---|
| T | 325,2 | 1 | 47 | |
| CT | 614,4 | 2 | 11 | |
| AT | 654,4 | 2 | 14 | |
| GT | 670,4 | 2 | 15 | |
| $C_2T$ | 903,5 | 3 | 4 | |
| ACT | 943,6 | 3 | 3 | |
| CGT | 959,6 | 3 | 7 | |
| $A_2T$ | 983,6 | 3 | 5 | |
| AGT | 999,6 | 3 | 1 | |
| $G_2T$ | 1015,6 | 3 | 4 | |
| $C_3T$ | 1192,7 | 4 | 2 | * |
| $AC_2T$ | 1232,7 | 4 | 5 | * |
| $C_2GT$ | 1248,7 | 4 | 4 | |
| $A_2CT$ | 1272,8 | 4 | 3 | |
| ACGT | 1288,8 | 4 | 6 | |
| $CG_2T$ | 1304,8 | 4 | 5 | |
| $A_3T$ | 1312,8 | 4 | 1 | weak |
| $A_2GT$ | 1328,8 | 4 | 1 | weak |
| $AG_2T$ | 1344,8 | 4 | 5 | |
| $AC_3T$ | 1521,9 | 5 | 1 | |
| $C_3GT$ | 1537,9 | 5 | 2 | |
| $A_2C_2T$ | 1562,0 | 5 | 2 | |
| $AC_2GT$ | 1578,0 | 5 | 2 | * |
| $C_2G_2T$ | 1594,0 | 5 | 7 | * |
| $A_2CGT$ | 1618,0 | 5 | 1 | weak |
| $ACG_2T$ | 1634,0 | 5 | 3 | * |
| $CG_3T$ | 1650,0 | 5 | 3 | |
| $A_3GT$ | 1658,0 | 5 | 2 | |
| $A_2G_2T$ | 1674,0 | 5 | 2 | |
| $G_4T$ | 1706,0 | 5 | 1 | * |
| $C_5T$ | 1771,1 | 6 | 1 | * |
| $C_4GT$ | 1827,1 | 6 | 1 | * |
| $AC_3GT$ | 1867,1 | 6 | 2 | * |
| $C_3G_2T$ | 1883,1 | 6 | 2 | |
| $A_3C_2T$ | 1891,2 | 6 | 1 | |
| $AC_2G_2T$ | 1923,2 | 6 | 2 | * |
| $C_2G_3T$ | 1939,2 | 6 | 1 | |
| $A_4GT$ | 1987,2 | 6 | 1 | |
| $AC_4GT$ | 2156,3 | 7 | 1 | |
| $C_4G_2T$ | 2172,3 | 7 | 1 | |
| $A_2C_3GT$ | 2196,3 | 7 | 1 | |
| $AC_3G_2T$ | 2212,3 | 7 | 2 | |
| $A_3C_2GT$ | 2236,4 | 7 | 1 | |
| $A_2C_2G_2T$ | 2252,4 | 7 | 2 | |
| $C_2G_4T$ | 2284,4 | 7 | 1 | |
| $A_3CG_2T$ | 2292,4 | 7 | 1 | |
| $A_2CG_3T$ | 2308,4 | 7 | 2 | |
| $ACG_4T$ | 2324,4 | 7 | 1 | |
| $AC_5GT$ | 2445,5 | 8 | 1 | * |
| $A_2C_2G_3T$ | 2597,6 | 8 | 1 | |
| $A_4CG_2T$ | 2621,6 | 8 | 1 | |
| $A_2CG_4T$ | 2653,6 | 8 | 1 | |
| $A_4C_3GT$ | 2854,8 | 9 | 1 | |
| $A_6C_2T$ | 2878,8 | 9 | 1 | |
| $A_2C_3G_3T$ | 2886,8 | 9 | 1 | |
| $A_2CG_4T$ (5'ppp-) | 2893,6 | 8 | 1 | |
| $A_3C_2G_3T$ | 2926,8 | 9 | 1 | |
| $C_8GT$ | 2983,9 | 10 | 1 | weak* |
| $A_2C_5G_2T$ | 3119,9 | 10 | 1 | |
| $A_3C_3G_3T$ | 3216,0 | 10 | 1 | * |
| $A_2C_3G_4T$ | 3232,0 | 10 | 1 | |
| $A_3C_2G_4T$ | 3272,0 | 10 | 1 | |
| $A_2C_2G_5T$ | 3288,0 | 10 | 1 | |
| $A_5C_5T$ | 3417,1 | 11 | 1 | |
| $A_5C_3G_2T$ | 3529,2 | 11 | 1 | |
| $A_6CG_3T$ | 3625,2 | 11 | 1 | |
| $AC_3G_7T$ | 3938,4 | 12 | 1 | |
| $A_2C_7G_3T$ | 4043,5 | 13 | 1 | |
| $A_3C_5G_3T$ | 4139,6 | 12 | 1 | |
| $A_5C_3G_4T$ | 4219,6 | 13 | 1 | |
| $A_4C_2G_6T$ | 4291,6 | 13 | 1 | |
| $A_3C_8G_3T$ | 4661,9 | 15 | 1 | |
| $A_5C_4G_5T$ | 4854,0 | 15 | 1 | |
| $A_6C_3G_4T$ | 5536,4 | 17 | 1 | |
| $A_6C_6G_6T$ | 6106,8 | 19 | 1 | |
| $A_4C_7G_{13}T$ | 8154,0 | 25 | 1 | |
| $A_{13}C_8G_{10}T$ | 10370,5 | 32 | 1 | not observed |

Σ = 222

We claim:

1. A method for sequencing one or more target nucleic acids present in one or more biological samples, said method comprising the steps of:

(a) deriving from one or more biological samples the one or more target nucleic acids;

(b) subjecting the one or more target nucleic acids obtained from step (a) to two or more separate base-specific, sequence-specific or site-specific complementary cleavage reactions, wherein each cleavage reaction generates a non-ordered set of fragments;

(c) analyzing the sets of non-ordered fragments obtained from step (b) by mass spectrometry; and, (d) performing a systematic computational analysis on the mass spectra obtained from step (c) and sequencing said target nucleic acid;

wherein said complementary cleavage reactions refer to comprise target nucleic acid digestions characterized by varying specificity and/or to digestion of alternative forms of the target sequence.

2. The method according to claim 1 wherein the one or more biological samples are derived from an organism selected from the group consisting of eukaryotes, prokaryotes, and viruses.

3. The method according to claim 1 wherein the one or more target nucleic acids are selected from the group consisting of single stranded DNA, double stranded DNA, cDNA, single stranded RNA, double stranded RNA, DNA/RNA hybrid, and DNA/RNA mosaic nucleic acid.

4. The method according to claim 1 wherein one or more target nucleic acids are derived by one or more consecutive amplification procedures selected from the group consisting of in vivo cloning, polymerase chain reaction (PCR), reverse transcription followed by the polymerase chain reaction (RT-PCR), strand displacement amplification (SDA), and transcription based processes.

5. The method according to claim 4 wherein the one or more amplified target nucleic acids are transcripts generated from a single stranded or a double stranded target nucleic acid by a process comprising the steps of:
   (a) operatively linking a transcription control sequence to the one or more target nucleic acids; and
   (b) transcribing one or both strands of the one or more target nucleic acid of step a) using one or more RNA polymerases that recognize the transcription control sequence on the one or more target nucleic acids.

6. The method according to claim 5 wherein said transcriptional control sequences is operatively linked to one or more target nucleic acids by PCR amplification using a primer that incorporates the transcriptional control sequence as a 5'-extensions.

7. The method according to claim 5 wherein the transcription control sequence is selected from the group consisting of a eukaryotic transcription control sequence, a prokaryotic transcription control sequence, and a viral transcription control sequence.

8. The method according to claim 7 wherein the prokaryotic transcription control sequence is selected from the group consisting of T3, T7, and SP6 promoters.

9. The method according to claim 8 wherein the RNA polymerases which utilize the T3, T7, or SP6 promoters are either wild type or mutant RNA polymerases, the mutant polymerases being capable of incorporating into the transcript non-canonical substrates with a 2'-deoxy, 2'-O-methyl, 2'-fluoro or 2'-amino substituent.

10. The method according to claim 9 wherein the mutant RNA polymerase is either T7 mutant polymerase or SP6 mutant polymerase.

11. The method according to claim 1 wherein the derived target nucleic acid incorporates one or more nucleosides that are modified on the base, the sugar, and/or the phosphate moiety, wherein the modifications alter the specificity of cleavage by the one or more cleavage reagents and/or the mass and/or the length of the cleavage products.

12. The method according to claim 11 wherein the modification is introduced through the enzymatic incorporation of a modified deoxynucleoside triphosphate, a modified ribonucleoside triphosphate, and/or a modified dideoxynucleoside triphosphate; or wherein the modification is introduced chemically, or wherein the modification is introduced through a combination of both methods.

13. The method according to claim 11 wherein the modification consists of a 2'-deoxy, 2'-O-methyl, 2'-fluoro or 2'-amino substituent on the nucleotide triphosphates.

14. The method according to claim 11 wherein the modification consists of phosphorothioate internucleoside linkages or phosphorothioate internucleoside linkages further reacted with an alkylating reagent.

15. The method according to claim 11 wherein the modification consists of a methyl group on C5 of the uridine-5'-monophosphate subunits.

16. The method according to claim 11 wherein the modification consists of nucleotides that incorporate alternative isotopes.

17. The method according to claim 1 wherein the one or more target nucleic acids of step (a) are purified prior to cleavage.

18. The method according to claim 17 wherein said purification is achieved through immobilization or by chromatography.

19. The method according to claim 1 wherein the complementary cleavage reactions are selected from the group consisting of enzymatic cleavage, chemical cleavage, and physical cleavage.

20. The method according to claim 19 wherein the complementary cleavage reactions are characterized by a relaxed mono-nucleotide, mono-nucleotide, relaxed di-nucleotide, or di-nucleotide specificity.

21. The method according to claim 19 wherein the one or more target nucleic acids are subjected to chemical digestion reaction consisting of treatment with alkali or with reagents used in the Maxam & Gilbert sequencing method.

22. The method according to claim 19 wherein the one or more target nucleic acids are subjected to enzymatic cleavage reaction using one or more enzymes selected from the group consisting of endonucleases and exonucleases.

23. The method according to claim 22 wherein the one or more target nucleic acids are subjected to enzymatic cleavage reaction using one or more endonucleases, selected from the group consisting of restriction enzymes, RNA endonucleases, DNA endonucleases and non-specific phosphodiesterases.

24. The method according to claim 23 wherein the one or more endonucleases are one or more selective or non-selective RNA endonucleases, selected from the group consisting of the G-specific T1 ribonuclease, the A-specific U2 ribonuclease, the A/U specific phyM ribonuclease, the U/C specific ribonuclease A, the C-specific chicken liver ribonuclease (RNaseCL3) and cusativin, non-specific RNase-I, and pyrimidine-adenosine preferring RNases isolated from *E. coli, Enterobacter* sp., or *Saccharomyces cerevisiae*.

25. The method according to claim 1 wherein the one or more target nucleic acids are phosphorothioate-modified single stranded DNA or RNA, and wherein the cleavage reactions are performed with the nuclease P1.

26. The method according to claim 1 wherein the one or more target nucleic acids are mosaic RNA/DNA nucleic acids or modified mosaic RNA/DNA nucleic acids, prepared with mutant polymerases, and wherein the cleavage reagents are RNA endonucleases, DNA endonucleases or alkali.

27. The method according to claim 1 wherein the one or more target nucleic acids are transcripts, modified transcripts, mosaic RNA/DNA transcripts or modified mosaic RNA/DNA transcripts, prepared with wild type or mutant RNA polymerases, and wherein the cleavage reagents are one or more selective or non-selective RNA endonucleases or alkali.

28. The method according to claim 1 the one or more target nucleic acids are mosaic RNA/DNA transcripts that incorporate either dCMP, dUMP or dTMP, prepared with mutant T7 or SP6 polymerase, and wherein the cleavage reagent is a pyrimidine-specific RNase.

29. The method according to claim 1 further comprising ion-exchange chromatographic purification of the set of non-ordered fragments of step (b).

30. The method according to claim 1 wherein the set of non-ordered fragments of step (b) is spotted onto a solid support.

31. The method according to claim 30 wherein said solid support is chosen from a group consisting of solid surfaces, plates and chips.

32. The method according to claim 1 wherein the mass spectrometric analysis of the nucleic acid fragments is performed using a mass spectrometric method selected from the group consisting of Matrix-Assisted Laser Desorption/Ionization-Time-of-flight (MALDI-TOF), Electrospray-Ionization (ESI), and Fourier Transform-Ion Cyclotron Resonance (FT-ICR).

33. The method according to claim 1, wherein said method is used for re-sequencing of one or more target nucleic acids for which a reference nucleic acid sequence is known; said method comprising an additional step wherein the one or more mass spectra of the non-ordered fragments obtained in step c) are compared with the known or predicted mass spectra for a reference nucleic acid sequence, and deducing therefrom, by systematic computational analysis, all or part of the nucleotide sequence of the one or more target nucleic acids, and comparing the deduced nucleic acid sequence with the reference nucleic acid to determine whether the one or more target nucleic acids have the same sequence or a different sequence from the reference nucleic acid.

34. The method according to claim 33 wherein the nucleic acid sequence difference that is determined is a deletion, substitution, insertion or combinations thereof.

35. The method according to claim 34 wherein the nucleic acid sequence difference is a Single Nucleic Polymorphism (SNP).

36. The method according to claim 33 wherein said method identifies known as well as unknown nucleotide sequence variations of said one or more target nucleic acids present in said one or more biological samples.

37. The method according to claim 36 wherein determination of said known or unknown nucleotide sequence variations allows the identification of the various allelic sequences of a certain region/gene, the scoring of disease-associated mutations, the detection of somatic variations, or studies in the field of molecular evolution.

38. The method according to claim 1 wherein the spectra obtained for one or more target nucleic acids are compared with the mass spectra predicted for a plurality of reference nucleic acids thereby identifying/detecting one or more target nucleic acids in one or more biological samples.

39. The method according to claim 38 wherein said method produces an expression profile of one or more biological samples.

40. A method according to claim 1 for sequencing of one or more target nucleic acids of unknown sequence present in one or more biological samples, said method comprising the steps of:
(a) deriving from one or more biological samples one or more target nucleic acids in a single stranded form;
(b) subjecting the one or more target nucleic acids obtained from step (a) to a set of four separate base-specific complementary cleavage reactions, wherein each cleavage reaction generates a non-ordered set of fragments;
(c) analyzing the sets of non-ordered fragments obtained from step (b) by mass spectrometry;
(d) performing a systematic computational analysis on the mass spectra obtained from step (c) to assemble the sequence of said target nucleic acid; and,
(e) optionally, if the sequence is not uniquely defined after step (d), repeating steps (a) through (d), thereby generating modified forms of said target nucleic acid and/or different portions of said target nucleic acid, and performing supplementary mono-and/or di-nucleotide specific cleavage reactions rendering supplementary sets of non-ordered fragments until the combined data converge into a unique sequence solution,
wherein said complementary cleavage reactions refer to target nucleic acid digestions characterized by varying specificity and/or to digestion of alternative forms of the target sequence.

41. The method according to claim 36 wherein said method provides genome wide genotyping of one or more biological samples.

42. The method of claim 28, wherein the pyrimidine-specific RNase is RNase A.

43. The method of claim 1 or 33, wherein said method comprises four RNase-specific cleavage reactions.

44. The method of claim 43, wherein said four RNase-specific cleavage reactions comprise RNase T1 and RNase U2 cleavage of the + and − strands of said target nucleic acid.

45. The method of claim 43, wherein said four RNase-specific cleavage reactions comprise RNase A or RNase A and RNase T1 cleavage of the + and − strands of said target nucleic acid.

46. A kit for sequence analysis mass spectrometry re-sequencing according to a method of claim 33 of one or more target nucleic acids for which a reference nucleic acid sequence is known in one or more biological samples using mass spectrometry, the kit comprising:
(a) one or more nucleotide triphosphates;
(b) one or more polymerases;
(c) one or more nucleic acid cleaving agents; and;
(d) one or more sets of reference nucleic acids for which the nucleic acid sequence is known;
(e) reagents to purify the target nucleic acid;
(f) ion exchange beads in order to purify the non ordered set of fragments;
(g) a solid support suitable for use in mass spectrometry analysis whereon the non ordered set of fragments may be spotted; and,
(h) a computer software for comparing the mass spectra of the one or more target nucleic acid with the mass spectra of the reference nucleic acid and deducing therefrom the nucleic acid sequence of the target nucleic acid.

47. The kit of claim 46 wherein said cleaving agent is an endonuclease selected from the group consisting of U/C specific RNase A, G-specific T1 ribonuclease, A-specific U2 ribonuclease, A/U specific phyM ribonuclease, C-specific chicken liver ribonuclease (RNaseCL3) and cusativin.

48. The kit of claim 46, wherein said kit comprises:
(a) four nucleotide triphosphates;
(b) a T7 or SP6 polymerase;
(c) a RNase T1 and RNase U2;
(d) one or more sets of reference nucleic acids for which the nucleic acid sequence is known;
(e) reagents to purify the target nucleic acid;
(f) ion exchange beads in order to purify the non-ordered set of fragments;
(g) a solid support suitable for use in mass spectrometry analysis whereon the non-ordered set of fragments may be spotted; and
(h) a computer software for comparing the mass spectra of the one or more target nucleic acid with the mass spectra of the reference nucleic acid and deducing therefrom the nucleic acid sequence of the target nucleic acid.

49. A kit for sequence analysis mass spectrometry sequencing according to a method of claim 1 of one or more unknown target nucleic acids in one or more biological sample using mass spectroscopy, the kit comprising:
- (a) one or more nucleotide triphosphates;
- (b) one or more polymerases; and,
- (c) one or more nucleic acid cleaving agents;
- (d) optionally, reagents to purify the target nucleic acid;
- (e) ion exchange beads in order to purify the non ordered set of fragments;
- (f) a solid support suitable for use in mass spectrometry analysis whereon the non ordered set of fragments may be spotted; and,
- (g) computer software for analysing the mass spectra of the sequence of said target nucleic acid resulting in one or more unique sequences.

50. The kit of claim 49 wherein said cleaving agent is an endonuclease selected from the group consisting of U/C specific RNase A, G-specific T1 ribonuclease, A-specific U2 ribonuclease, A/U specific phyM ribonuclease, C-specific chicken liver ribonuclease (RNaseCL3) and cusativin.

51. The kit of claim 46 or 49, wherein said one or more polymerases are SP6 and T7 RNA polymerase and said cleaving agent is an endonuclease selected from the group consisting of U/C specific RNase A, G-specific T1 ribonuclease, A-specific U2 ribonuclease, A/U specific phyM ribonuclease, C-specific chicken liver ribonuclease (RNaseCL3) and cusativin.

52. The kit of claim 49, wherein said kit comprises:
- (a) four nucleotide triphosphates;
- (b) a T7 or SP6 polymerase;
- (c) a RNase T1 and RNase U2;
- (d) reagents to purify the target nucleic acid;
- (e) ion exchange beads in order to purify the non-ordered set of fragments;
- (f) a solid support suitable for use in mass spectrometry analysis whereon the non-ordered set of fragments may be spotted; and,
- (g) a computer software for analysing the mass spectra of the sequence of said target nucleic acid resulting in one or more unique sequences.

53. The kit of claim 48 or 52, wherein said T7 or SP6 polymerase is a mutant polymerase that incorporates non-canonical substrates with a 2'-deoxy, 2'-O-methyl, 2'-fluoro or 2'-amino substituent into the transcript.

54. A kit for mass spectrometry sequencing according to a method of claim 1 or claim 33 of one or more target nucleic acids in one or more biological samples using mass spectrometry, the kit comprising:
- (a) one or more ribonucleotide triphosphates and one or more deoxyribonucleotide triphosphates;
- (b) one or more polymerases;
- (c) one or more RNAses;
- (d) a solid support suitable for use in mass spectrometry analysis whereon the non-ordered set of fragments may be spotted and (e) a computer software for analysing the mass spectra of the sequence of said target nucleic acid resulting in one or more unique sequences.

* * * * *